(12) United States Patent
Hibi et al.

(10) Patent No.: US 7,323,569 B2
(45) Date of Patent: Jan. 29, 2008

(54) 7-PHENYLPYRAZOLOPYRIDINE COMPOUNDS

(75) Inventors: Shigeki Hibi, Tsukuba (JP); Yorihisa Hoshino, Tsukuba (JP); Koichi Kikuchi, Tsuchiura (JP); Kogyoku Shin, Tsukuba (JP); Yoshinori Takahashi, Tsukuba (JP); Masae Fujisawa, Toride (JP); Hisashi Shibata, Ushiku (JP); Mitsuhiro Ino, Ushiku (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 10/524,662

(22) PCT Filed: Oct. 22, 2003

(86) PCT No.: PCT/JP03/13490

§ 371 (c)(1),
(2), (4) Date: Dec. 13, 2005

(87) PCT Pub. No.: WO2004/037822

PCT Pub. Date: May 6, 2004

(65) Prior Publication Data

US 2006/0235011 A1    Oct. 19, 2006

Related U.S. Application Data

(60) Provisional application No. 60/421,071, filed on Oct. 25, 2002.

(30) Foreign Application Priority Data

Oct. 22, 2002    (JP)    ............... 2002-306695

(51) Int. Cl.
| | | |
|---|---|---|
| C07D 471/02 | (2006.01) | |
| C07D 491/02 | (2006.01) | |
| C07D 498/02 | (2006.01) | |
| C07D 513/02 | (2006.01) | |
| C07D 515/02 | (2006.01) | |

(52) U.S. Cl. .................................... 546/121
(58) Field of Classification Search ............. 548/361.5, 548/362.1; 514/418; 546/121
See application file for complete search history.

(56) References Cited

U.S. PATENT DOCUMENTS

| | | |
|---|---|---|
| 4,925,849 A | 5/1990 | Shiokawa et al. |
| 4,990,516 A | 2/1991 | Ohashi et al. |
| 5,338,743 A | 8/1994 | Shiokawa et al. |
| 5,445,943 A | 8/1995 | Hoenes |
| 5,457,200 A | 10/1995 | Zimmermann et al. |
| 5,565,468 A | 10/1996 | Larsen et al. |
| 5,691,347 A | 11/1997 | Corbier et al. |
| 7,091,215 B2 * | 8/2006 | Hibi et al. .................. 514/300 |
| 7,151,109 B2 * | 12/2006 | Fu .............................. 514/300 |
| 7,176,216 B2 | 2/2007 | Hibi et al. |

FOREIGN PATENT DOCUMENTS

| | | |
|---|---|---|
| EP | 0 433 853 A1 | 6/1991 |
| EP | 0 433 854 A2 | 6/1991 |
| EP | 0 611 766 A1 | 8/1994 |
| EP | 0 659 747 A1 | 6/1995 |
| EP | 0812831 A1 | 12/1997 |
| JP | 2001-89368 A | 4/2001 |
| WO | WO-94/13643 A1 | 6/1994 |
| WO | WO-94/13644 A1 | 6/1994 |
| WO | WO-94/13661 A1 | 6/1994 |
| WO | WO-94/13676 A1 | 6/1994 |

(Continued)

OTHER PUBLICATIONS

Hiroi et al., Molecular Psychiatry, "Expression of corticotropin releasing hormone receptors type I and type II mRNA in suicide victims and controls", 2001, vol. 6, pp. 540-546.*
Sauvage et al., Neuroscience, "Detection of corticotropin-releasing hormone receptor 1 immunoreactivity in cholinergic, dopaminergic and noradrenergic neurons of the murine nasal forebrain and brainstem nuclei-potential implication for arousal and attention", vol. 104, pp. 643-652.*
Vale et al., Science, vol. 213, pp. 1394-1397, (1981).
Rivier et al., Proc. Natl. Acad. Sci, vol. 80, pp. 4851-4855, (1983).
Shibahara et al., EMBO Journal, vol. 2, No. 5, pp. 775-779, (1983).
Dieterich et al., Exp. Clin. Endocrinol. Diabetes, vol. 105, pp. 65-82, (1997).

(Continued)

Primary Examiner—Margaret D. Seaman
Assistant Examiner—Niloofar Rahmani
(74) Attorney, Agent, or Firm—Birch, Stewart, Kolasch & Birch, LLP

(57) ABSTRACT

A compound represented by the formula:

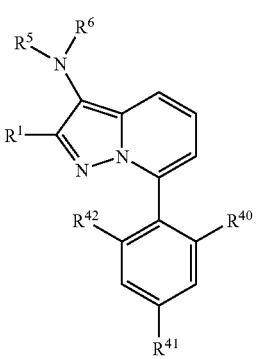

(I)

[wherein $R^1$ is methoxy, methylthio, ethyl, etc.; $R^5$ and $R^6$ are each independently cyclopropylmethyl, (4-tetrahydropyranyl)methyl, etc.; and two of $R^{40}$, $R^{41}$ and $R^{42}$ are $C_{1-6}$ alkoxy while the remaining one is methoxymethyl, etc.], a salt thereof, or a hydrate of the foregoing. This compound has excellent antagonism against corticotropin-releasing factor receptor.

12 Claims, No Drawings

FOREIGN PATENT DOCUMENTS

| WO | WO-94/13677 A1 | 6/1994 |
| --- | --- | --- |
| WO | WO-95/10506 A1 | 4/1995 |
| WO | WO-95/34563 A1 | 12/1995 |
| WO | WO-97/29109 A1 | 8/1997 |
| WO | WO-97/29110 A1 | 8/1997 |
| WO | WO-98/08847 A1 | 3/1998 |
| WO | WO-98/35967 A2 | 8/1998 |
| WO | WO-99/01454 A1 | 1/1999 |
| WO | WO-99/10350 A1 | 3/1999 |
| WO | WO-00/01697 A1 | 1/2000 |
| WO | WO-00/39127 A1 | 7/2000 |
| WO | WO-00/59907 A2 | 10/2000 |
| WO | WO-00/59908 A2 | 10/2000 |
| WO | WO-01/35917 A1 | 5/2001 |
| WO | WO-01/44248 A1 | 6/2001 |
| WO | WO-02/06286 A2 | 1/2002 |
| WO | WO-02/058704 A1 | 8/2002 |
| WO | WO-02/18320 A1 | 9/2002 |
| WO | WO-02/088121 A1 | 11/2002 |
| WO | WO-03/072536 A1 | 9/2003 |
| WO | WO-03/078435 A1 | 9/2003 |

OTHER PUBLICATIONS

Vale et al., Recent Progress in Hormone Research, vol. 39, pp. 245-270, (1983).
Dunn et al., Brain Research Reviews, vol. 15, pp. 71-100, (1990).
Owens et al., Pharmacol. Reviews, vol. 43, No. 4, pp. 425-473, (1991).
Arborelius et al., J. of Endocrinology, vol. 160, pp. 1-12, (1999).
Kalin et al., Brain Research, vol. 509, pp. 80-84, (1990).
Tazi et al., Regulatory Peptides, vol. 18, pp. 37-42, (1987).
Stenzel-Poore et al., J. of Neuroscience, vol. 14, No. 5, pp. 2579-2584, (1994).
Baldwin et al., Psychopharmacology, vol. 103, pp. 227-232, (1991).
Sirinathsinghji et al., Nature, vol. 305, pp. 232-235, (1983).
Sherman et al., Pharm. Bio. & Behavior, vol. 26, pp. 699-703, (1987).
Chalmers et al.; TIPS, vol. 17, pp. 166-172, (1996).
Ehlers et al., Brain Research, vol. 278, pp. 332-336, (1983).
Banki et al., Am. J. Psychiatry, vol. 144, No. 7, pp. 873-877, (1987).
Whitehouse et al., Neurology, vol. 37, pp. 905-909, (1987).
De Souza et al., Brain Research, vol. 437, pp. 355-359, (1987).
Stenzel-Poore et al., Endocrinology, vol. 130, No. 6, pp. 3378-3386, (1992).
Krahn et al., Brain Research Bulletin, vol. 17, pp. 285-289, (1986).
Taché et al., Annals of the New York Academy of Sciences, vol. 697, pp. 233-243, (1993).
Barquist et al., American Physiological Society, pp. G616-G620, (1992).
Gunion et al., American Physiological Society, pp. G152-G157, (1990).
Bakke et al., Life Sciences, vol. 45, pp. 907-916, (1989).
Lenz et al., Gastroenterology, vol. 95, pp. 1510-1517, (1988).
Ford et al., Gastroenterology, vol. 109, pp. 1772-1780, (1995).
Lembo et al., Neurogastroenterol. Mot., vol. 8, pp. 9-18, (1996).
Fukudo et al., Gut, vol. 42, pp. 845-849, (1998).
Morimoto et al., J. of Physiology, vol. 460, pp. 221-229, (1993).
Theoharides et al., Endocrinology, vol. 139, No. 1, pp. 403-413, (1998).
Scopa et al., Am. J. of Pathology, vol. 145, No. 5, pp. 1159-1167, (1994).
Poliak et al., Journal of Immunology, vol. 158, pp. 5751-5756, (1997).
Murakami et al., Endocrine Journal, vol. 44, No. 4, pp. 627-629, (1997).
Singh et al., Journal of Neuroimmunology, vol. 23, pp. 257-262, (1989).
Singh et al., Neuroscience Letters, vol. 120, pp. 151-154, (1990).
Jain et al., Endocrinology, vol. 128, No. 3, pp. 1329-1336, (1991).
Böhmer et al., European Journal of Pharmacology, vol. 182, pp. 405-411, (1990).
Nink et al., Acta Endocrinologica, vol. 127, pp. 200-204, (1992).
Rivier et al., Science, vol. 224, pp. 889-891, (1984).
Menzaghi et al., J. of Pharm. & Exp. Therapeautics, vol. 269, No. 2, pp. 564-572, (1994).
Sasaki et al., J. of Clin. End. And Metab., vol. 65, No. 1, pp. 176-182, (1987).
Sasaki et al., J. of Clin. End. And Metab., vol. 67, No. 4, pp. 768-773, (1988).
Garrick et al., Reg. Peptides, vol. 21, pp. 173-181, (1988).
Petrusz et al., Peptides, vol. 5, Sup. 1, pp. 71-78, (1984).
Chalmers et al., J. of Neuro., vol. 15, No. 10, pp. 6340-6350, (1995).
Liaw et al., Endocrinology, vol. 137, No. 1, pp. 72-77, (1996).
Valdenaire et al., BBA, vol. 1352, pp. 129-132, (1997).
Vale et al., Recent Prog. Horm. Res., vol. 39, pp. 245-270, (1983).
Raadsheer et al., Am. J. Psychiatry, vol. 152, No. 9, pp. 1372-1376, (1995).
Nemeroff et al., Arch. Gen. Psychiatry, vol. 45, pp. 577-579, (1988).
Gold et al., N. Engl. J. Med., vol. 314, No. 21, pp. 1329-1335, (1986).
Altemus et al., Arch. Gen. Psychiatry, vol. 51, pp. 794-803, (1994).
Bremner et al., Am. J. Psychiatry, vol. 154, No. 5, pp. 624-629, (1997).
Chappell et al., Biol. Psychiatry, vol. 39, pp. 776-783, (1996).
Roy-Byrne et al., Am J. Psychiatry, vol. 143, No. 7, pp. 896-899, (1986).
Monnikes et al., Brain Research, vol. 574, pp. 70-76, (1992).
Butler et al., J. of Neuroscience, vol. 10, No. 1, pp. 176-183, (1990).
Owens et al., J. of Pharm. And Exp. Ther., vol. 258, No. 1, pp. 349-356, (1991).
Lyons et al., Brain Research, vol. 545, pp. 339-342, (1991).
Strijbos et al., Brain Research, vol. 656, pp. 405-408, (1994).
Behan et al., Nature, vol. 378, pp. 284-287, (1995).
Diamant et al., Neuroendocrinology, vol. 57, pp. 1071-1081, (1993).
Hotta et al., J. Clin. Endocrinology, vol. 62, No. 2, pp. 319-324, (1986).
Levine et al., Neuropharmacology, vol. 22, No. 3A, pp. 337-339, (1983).
Arase et al., Physiology & Behavior, vol. 45, pp. 565-570, (1989).
Plotsky et al., Endocrinology, vol. 130, No. 4, pp. 1931-1941, (1992).
Nicholson et al., Regulatory Peptides, vol. 18, pp. 173-188, (1987).
Tache et al., Am. J. Physiol., vol. 253, pp. G241-G245, (1987).
Karlais et al., Science, vol. 254, pp. 421-423, (1991).
Crofford et al., J. Clin. Invest., vol. 90, pp. 2555-2564, (1992).
Crofford et al., J. of Immun., vol. 151, No. 3, pp. 1587-1596, (1993).
Singh et al., J. Pharmacol. Exp. Ther., vol. 288, No. 3, pp. 1349-1356, (1999).
Whitten et al., J. Med. Chem. 1996, 39, 4354-4357.
Chen et al., J. Med. Chem. 1996, 39, 4358-4360.

* cited by examiner

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic PCR primer hCYP3A4_F3

<400> SEQUENCE: 1
tagctgagga tgaagaatgg                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic PCR primer hCYP3A4_R3

<400> SEQUENCE: 2
gtggattgtt gagagagtcg                                                    20

<210> SEQ ID NO 3
<211> LENGTH: 19
<212> TYPE: DNA
<213> ORGANISM: Artificial Sequence
<220> FEATURE:
<223> OTHER INFORMATION: Synthetic PCR primer hGAPDH_F

<400> SEQUENCE: 3
gaaggtgaag gtcggagtc                                                     19

<210> SEQ ID NO 4
<211> LENGTH: 20
<212> TYPE: DNA
<213> ORGANISM: Artificial Sequence
<220> FEATURE:
<223> OTHER INFORMATION: Synthetic PCR primer hGAPDH_R

<400> SEQUENCE: 4
gaagatggtg atgggatttc                                                    20
```

7-PHENYLPYRAZOLOPYRIDINE COMPOUNDS

This National Phase PCT application claims priority under 35 U.S.C. 119(e) on U.S. Provisional Application No(s). 60/421,071 filed on Oct. 25, 2002 and under 35 U.S.C. 119(a) on Patent Application No(s). 2002-306695 filed in Japan on Oct. 25, 2002, all of which are hereby incorporated by reference.

TECHNICAL FIELD

The present invention relates to novel compounds having Corticotropin-Releasing Factor receptor antagonistic activity, salts thereof and hydrates of the foregoing, to processes for producing the same and to uses of the same as medicine.

BACKGROUND ART

Corticotropin-Releasing Factor (hereinafter abbreviated as "CRF") is a neuropeptide consisting of 41 amino acids which was first isolated from ovine hypothalamus [Science, 213, 1394 (1981)], after which its presence was also confirmed in rat [Proc. Natl. Acad. Sci. USA, 80, 4851 (1983)] and in human [EMBO J. 5, 775 (1983)]. CRF is most abundant in the pituitary gland and hypothalamus, and is also widely distributed throughout cerebral cortex, cerebellum and other areas of the brain. Its presence has also been confirmed in peripheral tissue such as the placenta, adrenal gland, lung, liver, pancreas and gastrointestinal tract [Exp. Clin. Endcrinol. Diabetes, 105, 65 (1997)]. Two subtype CRF receptor has been described, CRF1 and CRF2, and CRF1 receptor is reported to be widely distributed in cerebral cortex, cerebellum, olfactory bulb, pituitary gland, amygdaloidal nucleus and elsewhere. Recently, 2 subtypes of the CRF2 receptor have been confirmed, CRF2α and CRF2β, of which it has been discovered that CRF2α receptors are abundantly distributed in the hypothalamus, septal nucleus and choroid plexus, while CRF2β receptors are primarily distributed in peripheral tissue such as the skeletal muscle, or in the cerebral blood vessels of the central nervous system [Exp. Clin. Endocrinol. Diabetes, 105, 65 (1997)]. The fact that each of these receptors has a different distribution profile suggests that their roles are also different. CRF is produced and secreted in the hypothalamus and promotes stress-induced release of adrenocorticotropic hormone (ACTH) [Recent Prog. Horm. Res., 39, 245 (1983)]. In addition to its endocrine role, CRF also functions as a neurotransmitter or neuromodulator in the brain, integrating electrophysiological, autonomic and behavioral changes in response to stress [Brain Res. Rev., 15, 71 (1990); Pharmacol. Rev., 43, 425 (1991)].

CRF has been implicated in a variety of disease to date, as indicated by the following publications.

It was reported that elevated concentrations of CRF in the cerebrospinal fluid of patients with major depression compared with healthy individuals; CRF-mRNA levels in the hypothalamus of depressive patients are higher than that of healthy individuals; CRF receptors in cerebral cortex are reduced in suicide victims; plasma ACTH increase is diminished with administration of CRF to depressive patients [Journal of Endocrinology, 160, 1 (1999)]; CRF levels in the cerebrospinal fluid of some anxiety patients with obsessive-compulsive disorder, posttraumatic stress disorder or Tourette's syndrome are higher than in that of healthy individuals [Journal of Endocrinology, 160, 1 (1999)]; plasma ACTH increase is diminished with administration of CRF to panic disorder patients [Exp. Clin. Endcrinol. Diabetes, 105, 65 (1997)]; anxiety behavior has been observed in experimental animals by intracerebral administration of CRF. In addition, anxiety behavior is observed more frequently in CRF overexpressing mice than in normal mice [Journal of Endocrinology, 160, 1 (1999)], and CRF levels in the locus coeruleus are reduced by administration of anxiolytics [Exp. Clin. Endcrinol. Diabetes, 105, 65 (1997)]. Also, α-helical CRF(9-41), a peptide CRF antagonist, exhibits an antianxiety action in animal models [Brain Res., 509, 80 (1990); Regulatory Peptides, 18, 37 (1987); J. Neurosci., 14(5), 2579 (1994)]; and abnormal behavior withdrawal from alcohol or addictive drugs such as cocaine are inhibited by α-helical CRF(9-41), a peptide CRF antagonist [Psychopharmacology, 103, 227 (1991)].

CRF inhibits sexual behavior in rat [Nature, 305, 232 (1983)]; CRF reduces sleep in rat and is thus implicated the involvement in sleep disorder [Pharmacol. Biochem. Behav., 26, 699 (1987)]; α-helical CRF(9-41), a peptide CRF antagonist, suppresses brain damage or electroencephalogram disturbances due to brain ischemia or NMDA receptor activation [TIPS, 17, 166 (1996)]; CRF elicits electroencephalogram and induces convulsions [Brain Res., 278, 332 (1983)]; cerebrospinal CRF levels are elevated in schizophrenic patients compared with healthy individuals [Am. J. Psychiatry, 144(7), 873 (1987)]; CRF content in cerebral cortex is reduced in Alzheimer's disease patients, Parkinson's disease patients and progressive supranuclear palsy patients [Neurology, 37, 905 (1987)]; and CRF is reduced in the ganglia in Huntington's disease [Neurology, 37, 905 (1987); Brain Res., 437, 355 (1987)]. In addition, CRF administration has been found to enhance learning and memory in rat [Exp. Clin. Endcrinol. Diabetes, 105, 65 (1997)].

CRF content in cerebrospinal fluid are reduced in amyotrophic lateral sclerosis patients. Oversecretion of ACTH and adrenocorticosteroids are exhibited in mice overexpressing CRF, these mice display abnormalities similar to Cushing's syndrome, including muscular atrophy, alopecia and infertility [Endocrinology, 130(6), 3378 (1992)]; cerebrospinal CRF is elevated in anorexia nervosa patients compared with healthy individuals, and plasma ACTH increase is low with administration of CRF to anorexia nervosa patients; and CRF suppress feeding in experimental animals [TIPS, 17, 166 (1996)]. Moreover, α-helical CRF (9-41), a peptide CRF antagonist, improves stress-induced hypophagia in animal models [Brain Res. Bull., 17(3), 285 (1986)]; CRF has suppressed body weight gain in hereditary obese animals; a link has been suggested between low CRF levels and obesity syndrome; and the anorexic action and the body weight loss action of serotonin reuptake inhibitors has been possibly mediated by CRF release [TIPS, 17, 166 (1996)].

CRF acts centrally or peripherally to weaken gastric contraction and reduce gastric emptying [Annals of the New York Academy of Sciences, 697, 233 (1993)]. Furthermore, reduced gastric function induced by abdominal surgery is recovered by α-helical CRF(9-41), a peptide CRF antagonist [Am. J. Physiol., 262, G616 (1992)]; and CRF promotes secretion of bicarbonate ion in the stomach, thereby lowering gastric acid secretion and suppressing cold restraint stress ulcers [Am. J. Physiol., 258, G152 (1990)]. Also, administration of CRF increases ulcers in non-restraint stress animals [Life Sci., 45, 907 (1989)]; and CRF suppresses small intestinal transit and promotes large intestinal transit, and defecation is induced. In addition, α-helical CRF(9-41), a peptide CRF antagonist, has a inhibiting action against restraint stress-induced gastric acid secretion, reduced gastric emptying, reduced small intestinal transit and promoted large intestinal transit [Gastroenterology, 95, 1510 (1988)]; psychological stress in healthy individuals increases anxiety or sensations of gas and abdominal pain during colonic distension and CRF lowers the discomfort threshold [Gastroenterol., 109, 1772 (1995); Neurogastroenterol. Mot., 8, 9 (1996)]; and irritable bowel syndrome patients experience excessive acceleration of colonic motility with CRF administration compared to healthy individuals [Gut, 42, 845 (1998)].

Administration of CRF increases blood pressure, heart rate and body temperature, while α-helical CRF(9-41), a peptide CRF antagonist, suppresses stress-induced increases in blood pressure, heart rate and body temperature [J. Physiol., 460, 221 (1993)]. CRF production is increased locally in inflammation sites in experimental animals and in the synovial fluid of rheumatic arthritis patients [TIPS, 17, 166 (1996)]; CRF provokes degranulation of mast cells and promotes vascular permeability [Endocrinology, 139(1), 403 (1998)]; CRF is detected in autoimmune thyroiditis patients [Am. J. Pathol., 145, 1159 (1994)]; administration of CRF to experimental autoimmune encephalomyelitis rats has notably suppressed progression of symptoms such as paralysis [J. Immunol., 158, 5751 (1997)]; and urocortin (a CRF analogue) has increased growth hormone secretion in a pituitary adenoma culture system from an acromegalia patient [Endocri. J, 44, 627 (1997)]. Furthermore, CRF simulates secretion of cytokines such as interleukin-1 and interleukin-2 by leukocytes [J. Neuroimmunol., 23, 256 (1989); Neurosci. Lett., 120, 151 (1990)]; and CRF administration and stress both suppress T lymphocyte proliferation and natural killer cell activity. α-helical CRF(9-41), a peptide CRF antagonist, improves the reduced function of these immune cells caused by CRF administration or stress [Endocrinology, 128(3), 1329 (1991)], and breathing is notably increased by administration of CRF [Eur. J. Pharmacol., 182, 405 (1990)]. Finally, aggravated breathing and insomnia have been observed as a result of CRF administration to elderly patients under chronic artificial respiration [Acta Endocrinol. Copenh., 127, 200 (1992)].

The research cited above suggests that CRF antagonists may be expected to exhibit excellent effects for treatment or prevention of depression and depressive symptoms such as major depression, single-episode depression, recurrent depression, depression-induced child abuse and postpartum depression, mania, anxiety, generalized anxiety disorder, panic disorder, phobia, obsessive-compulsive disorder, post-traumatic stress disorder, Tourette's syndrome, autism, affective disorder, dysthymia, bipolar disorder, cyclothymic personality, schizophrenia, Alzheimer's disease, senile dementia of Alzheimer's type, neurodegenerative disease such as Parkinson's disease and Huntington's disease, multi-infarct dementia, senile dementia, anorexia nervosa, hyperphagia and other eating disorders, obesity, diabetes, alcohol dependence, pharmacophilia for drugs such as cocaine, heroin or benzodiazepines, drug or alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neuroses such as cardiac neurosis, gastric neurosis and bladder neurosis, peptic ulcer, irritable bowel syndrome, ulcerative colitis, Crohn's disease, diarrhea, constipation, postoperative ileus, stress-associated gastrointestinal disorders and nervous vomiting, hypertension, cardiovascular disorders such as angina pectoris nervosa, tachycardia, congestive heart failure, hyperventilation syndrome, bronchial asthma, apneusis, sudden infant death syndrome, inflammatory disorders (e.g., rheumatic arthritis, osteoarthritis, lumbago, etc.), pain, allergosis (e.g., atopic dermatitis, eczema, hives, psoriasis, etc.), impotence (erectile dysfunction), menopausal disorder, fertilization disorder, infertility, cancer, HIV infection-related immune dysfunction, stress-induced immune dysfunction, hemorrhagic stress, Cushing's syndrome, thyroid function disorder, encephalomyelitis, acromegaly, incontinence, osteoporosis, and the like. As examples of CRF antagonists there have been reported peptide CRF receptor antagonists with modifications or deletions of portions of the amino acid sequence of human or other mammalian CRF, and such antagonists have shown ACTH release-inhibiting action or anxiolytic action [Science, 224, 889(1984); J. Pharmacol. Exp. Ther., 269, 564 (1994); Brain Res. Rev., 15, 71 (1990)]. However, peptide derivatives have low utility value as drugs from the standpoint of pharmacokinetics including their in vivo chemical stability, oral absorption, bioavailability and intracerebral transport.

The following nonpeptide CRF antagonists have been reported.

[1] Pyrazolotriazine compounds (WO0059907), pyrazolopyrimidine compounds (WO0059908), imidazo[1,2-a]pyrazine compounds (WO0206286, WO0262800) and imidazo[1,2-a]pyridine compounds (WO9835967, WO02062800); and

[2] Benzimidazole compounds (EP0812831), imidazopyrimidine compounds and imidazopyridine compounds (EP0994877), imidazo[4,5-c]pyrazole compounds (WO9910350), benzimidazole compounds, imidazo-pyridine compounds, imidazo-pyridazine compounds and imidazo-triazine compounds (WO0001697), 1H-imidazo[4,5-d]pyridazin-7-one compounds and 3H-imidazo[4,5-c]pyridin-4-one compounds (WO0039127), imidazopyrimidine compounds and imidazopyridine compounds (WO0144248) and imidazole compounds (WO02058704).

However, none of these are compounds having a substituted amino group bonded at the 3-position and a substituted phenyl group bonded at the 7-position of pyrazolo[1,5-a]pyridine, and no compounds are known which exhibit CRF antagonism and have pyrazolo[1,5-a]pyridine as the skeleton, with a substituted amino group bonded at the 3-position and a substituted phenyl group bonded at the 7-position.

The following compounds which have pyrazolo[1,5-a]pyridine structure have also been reported: U.S. Pat. No. 5,457,200, U.S. Pat. No. 4,925,849, U.S. Pat. No. 5,565,468 and U.S. Pat. No. 5,691,347.

However, none of the compounds described in these publications are mentioned as exhibiting CRF receptor antagonism, antidepressive action or antianxiety action. (For example, the compounds described in U.S. Pat. No. 5,457,200 are mentioned only in terms of their use for colorimetry. The compounds described in U.S. Pat. No. 4,925,849 are mentioned only in terms of their use as diuretics and treatment agents for hypertension. The compounds described in U.S. Pat. No. 5,565,468 are mentioned only in regard to their angiotensin II antagonism and vasoconstrictive action. The compounds described in U.S. Pat. No. 5,691,347 are described in terms of their use as treatment agents for atherosclerosis and hypercholestelemia.)

Furthermore, when the structures of the compounds described in each of these publications are compared, none of the compounds are compounds having a substituted amino group bonded at the 3-position and a substituted phenyl group bonded at the 7-position of pyrazolo[1,5-a] pyridine. In other words, no compounds are known which have a substituted amino group bonded at the 3-position and a substituted phenyl group bonded at the 7-position of pyrazolo[1,5-a]pyridine, as according to the present invention, and absolutely no method is known for synthesis of such compounds.

DISCLOSURE OF INVENTION

As mentioned above, it is ardently desired to provide CRF receptor antagonists which are useful as drugs, and clinically effective agents that exhibit excellent CRF receptor antagonism and satisfy the requirements of pharmacological activity, dosage and safety as medicines have not yet been discovered. It is therefore an object of the present invention to investigate and discover such excellent CRF receptor antagonists.

As a result of much diligent examination and research in light of the circumstances described above, the present inventors have discovered novel pyrazolo[1,5-a]pyridine compounds exhibiting excellent CRF receptor antagonism.

The invention provides:

<1> a compound represented by the formula:

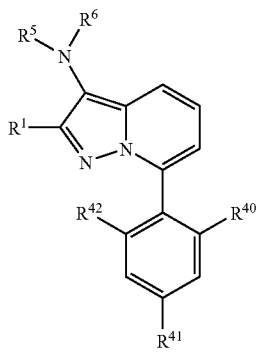

(I)

[wherein $R^1$ is a group represented by the formula $-G^{1z}-R^{1z}$ (wherein $G^{1z}$ is a single bond, oxygen or sulfur, and $R^{1z}$ is methyl or ethyl) or methoxymethyl;

$R^5$ and $R^6$ are each independently hydrogen, t-butoxycarbonyl or a group represented by the formula $-X^{6b}-X^{7b}$ (wherein $X^{6b}$ is methylene and $X^{7b}$ is $C_{1-6}$ alkyl, $C_{3-8}$ cycloalkyl, tetrahydropyran-yl or tetrahydrofuran-yl); and two of $R^{40}$, $R^{41}$ and $R^{42}$ are $C_{1-6}$ alkoxy while the remaining one is a group represented by the formula $-V^{1a}-V^{2a}$ (wherein $V^{1a}$ is a single bond, $-CO-$, $C_{1-6}$ alkylene, $C_{2-6}$ alkenylene or $C_{2-6}$ alkynylene, and $V^{2a}$ is hydrogen, hydroxyl, $C_{1-6}$ alkyl optionally substituted with 1 to 3 substituents selected from Substituent Group B below, $C_{1-6}$ alkoxy optionally substituted with 1 to 3 substituents selected from Substituent Group B below, a group represented by $-N(R^{3c})R^{3d}$ (wherein $R^{3c}$ and $R^{3d}$ are each independently hydrogen or $C_{1-6}$ alkyl optionally substituted with 1 to 3 substituents selected from Substituent Group B below), methanesulfonyloxy, p-toluenesulfonyloxy, pyrrolidinyl, piperazinyl, piperidyl, morpholinyl, $C_{3-8}$ cycloalkyl, tetrahydropyran-yl or tetrahydrofuran-yl), wherein Substituent Group B is the group consisting of fluorine atom, chlorine atom, bromine atom, cyano, $C_{1-6}$ alkoxy, pyrrolidinyl, piperazinyl, piperidyl, morpholinyl, $C_{3-8}$ cycloalkyl, tetrahydropyran-yl and tetrahydrofuran-yl], a salt thereof or a hydrate of the foregoing;

<2> a compound according to <1>, a salt thereof or a hydrate of the foregoing, wherein $R^1$ is methyl, ethyl, methoxy, methylthio or methoxymethyl;

<3> a compound according to <1>, a salt thereof or a hydrate of the foregoing, wherein $R^{40}$ and $R^{42}$ are each independently $C_{1-6}$ alkoxy, and $R^{41}$ is a group represented by the formula:

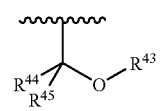

(wherein $R^{44}$ and $R^{45}$ are each independently hydrogen, methyl or ethyl; and $R^{43}$ is $C_{1-6}$ alkyl optionally substituted with 1 to 3 substituents selected from Substituent Group B below, wherein Substituent Group B is the group consisting of fluorine atom, chlorine atom, bromine atom, cyano, $C_{1-6}$ alkoxy, pyrrolidinyl, piperazinyl, piperidyl, inorpholinyl, $C_{3-8}$ cycloalkyl, tetrahydropyran-yl and tetrahydrofuran-yl);

<4> a compound represented by the formula:

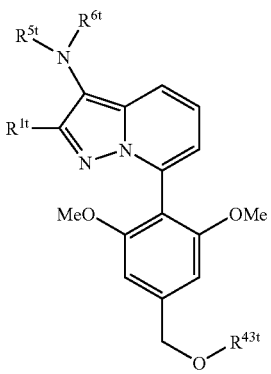

[wherein $R^{5t}$ and $R^{6t}$ are each independently cyclopropylmethyl, (4-tetrahydropyranyl)methyl, (3-tetrahydrofuranyl)methyl or (2-tetrahydrofuranyl)methyl;

$R^{1t}$ is methoxy, methylthio, methyl, ethyl or methoxymethyl; and $R^{43t}$ is $C_{1-6}$ alkyl], a salt thereof or a hydrate of the foregoing;

<5> a compound according to <4>, a salt thereof or a hydrate of the foregoing, wherein $R^{43t}$ is methyl;

<6> a compound according to <4>, a salt thereof or a hydrate of the foregoing, wherein $R^{1t}$ is methoxy, methylthio or ethyl;

<7> a compound according to <4>, a salt thereof or a hydrate of the foregoing, wherein $R^{5t}$ is cyclopropylmethyl or (4-tetrahydropyranyl)methyl;

<8> a compound according to <4>, a salt thereof or a hydrate of the foregoing, wherein $R^{5t}$ is (4-tetrahydropyranyl) methyl;

<9> a compound according to <4>, a salt thereof or a hydrate of the foregoing, wherein $R^{5t}$ is (4-tetrahydropyranyl)methyl, and $R^{6t}$ is cyclopropylmethyl;

<10> a compound according to <1>, a salt thereof or a hydrate of the foregoing, wherein the compound is N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine, N-cyclopropylmethyl-N-7-[4-(ethoxymethyl)-2,6-dimethoxyphenyl]-2-ethylpyrazolo[1,5-a]pyridin-3-yl-N-tetrahydro-2H-4-pyranylmethylamine or N-cyclopropylmethyl-N-[7-[2,6-dimethoxy-4-(methoxymethyl)phenyl]-2-(methylsulfanyl)pyrazolo[1,5-a]pyridin-3-yl]-N-tetrahydro-2H-4-pyranylmethylamine;

<11> a compound according to <1>, a salt thereof or a hydrate of the foregoing, wherein the compound is N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine;

<12> a compound (except (i) 4-(hydroxymethyl)-2,6-dimethoxyphenylboric acid and (ii) 4-(((t-butyldiphenylsilyl)oxy)methyl-2,6-dimethoxyphenylboric acid), represented by the formula:

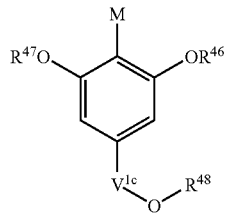

[wherein $R^{48}$ is hydrogen, $C_{1-6}$ alkyl optionally substituted with 1 to 3 substituents selected from Substituent Group B below, benzyl optionally substituted with 1 to 3 substituents selected from Substituent Group B below, 2-tetrahydropyranyl or a group represented by the formula:

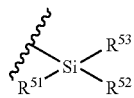

(wherein $R^{51}$, $R^{52}$ and $R^{53}$ are each independently $C_{1-6}$ alkyl or phenyl);

$R^{46}$ and $R^{47}$ are each independently $C_{1-6}$ alkyl;

$V^{1c}$ is $C_{1-6}$ alkylene;

M is a group represented by the formula:

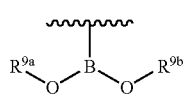

(wherein $R^{9a}$ and $R^{9b}$ are each independently hydrogen or $C_{1-6}$ alkyl, where $R^{9a}$ and $R^{9b}$ may bond together to form 1,2-ethylene, 1,3-propylene or 2,3-dimethyl-butan-2,3-diyl), or a group represented by the formula:

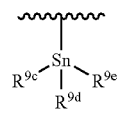

(wherein $R^{9c}$, $R^{9d}$ and $R^{9e}$ are each independently $C_{1-6}$ alkyl); and Substituent Group B is the group consisting of fluorine atom, chlorine atom, bromine atom, cyano, $C_{1-6}$ alkoxy, pyrrolidinyl, piperazinyl, piperidyl, morpholinyl, $C_{3-8}$ cycloalkyl, tetrahydropyranyl and tetrahydrofuranyl], a salt thereof or a hydrate of the foregoing;

<13> a compound according to <12>, a salt thereof or a hydrate of the foregoing, wherein $R^{46}$ and $R^{47}$ are methyl, and $V^{1c}$ is methylene;

<14> a compound according to <12>, a salt thereof or a hydrate of the foregoing, wherein $R^{46}$ and $R^{47}$ are methyl, $V^{1c}$ is methylene, and $R^{48}$ is methyl;

<15> a corticotropin-releasing factor (CRF) receptor antagonist comprising a compound according to <1> or a salt thereof;

<16> a corticotropin-releasing factor (CRF) 1 receptor antagonist comprising a compound according to <1> or a salt thereof;

<17> a therapeutic or prophylactic agent for a disease associated with corticotropin-releasing factor (CRF), comprising a compound according to <1> or a salt thereof;

<18> a therapeutic or prophylactic agent for depression, a depressive symptom, mania, anxiety, general anxiety disorder, panic disorder, phobia, obsessive-compulsive disorder, posttraumatic stress disorder, Tourette's syndrome, autism, affective disorder, dysthymia, bipolar disorder, cyclothymic personality or schizophrenia, comprising a compound according to <1> or a salt thereof;

<19> a therapeutic or prophylactic agent for peptic ulcer, irritable bowel syndrome, ulcerative colitis, Crohn's disease, diarrhea, constipation, postoperative ileus, stress-associated gastrointestinal disorder or nervous vomiting, comprising a compound according to <1> or a salt thereof;

<20> a therapeutic or prophylactic method for a disease associated with corticotropin releasing factor (CRF), comprising administration of a compound according to <1> or a salt thereof;

<21> a therapeutic or prophylactic method for depression, a depressive symptom, mania, anxiety, general anxiety disorder, panic disorder, phobia, obsessive-compulsive disorder, posttraumatic stress disorder, Tourette's syndrome, autism, affective disorder, dysthymia, bipolar disorder, cyclothymic personality or schizophrenia, comprising administration of a compound according to <1> or a salt thereof;

<22> a therapeutic or prophylactic method for peptic ulcer, irritable bowel syndrome, ulcerative colitis, Crohn's disease, diarrhea, constipation, postoperative ileus, stress-associated gastrointestinal disorder or nervous vomiting, comprising administration of a compound according to <1> or a salt thereof;

<23> use of a compound according to <1>, a salt thereof or a hydrate of the foregoing for the manufacture of a medicament; and <24> use of a compound according to <1>, a salt thereof or a hydrate of the foregoing for the manufacture of a therapeutic agent or a prophylactic agent for a disease for which inhibition of corticotropin releasing factor (CRF) receptor is effective.

BEST MODE FOR CARRYING OUT THE INVENTION

The symbols and terms used throughout the present specification will now be defined, with a more detailed description of the invention.

Several of the structural formulas given for compounds throughout the present specification will represent a specific isomer for convenience, but the invention is not limited to such specific isomers and encompasses all isomers and isomer mixtures, including geometric isomers, asymmetric carbon-derived optical isomers, stereoisomers and tautomers, implied by the structures of the compounds, of which any isomer or mixture thereof may be used. The compounds of the present invention therefore may include those having asymmetric carbons in their molecules and existing as optically active forms or racemic forms, and all such compounds are encompassed by the invention without restrictions. The compounds of the present invention may be crystalline or noncrystalline; there are also no restrictions on any crystalline polymorphism of the compounds, and any crystal forms may be used alone or in mixtures; and the compounds of the present invention also encompasses anhydrates, hydrates, and mixtures thereof. Metabolites of the compounds of the present invention, produced by degradation in vivo, are also encompassed by the claims of the invention.

The term "CRF receptor antagonist" as used throughout the present specification refers to a substance capable of inactivating CRF receptors. Such substances also include those capable of attenuating or inhibiting the physiological activity of CRF.

As diseases included among "diseases associated with CRF" or "diseases associated with CRF receptors" according to the present specification there may be mentioned depression and depressive symptoms (major depression, single-episode depression, recurrent depression, depression-induced child abuse, postpartum depression, etc.), mania, anxiety, generalized anxiety disorder, panic disorder, phobias, obsessive-compulsive disorder, posttraumatic stress disorder, Tourette's syndrome, autism, affective disorder, dysthymia, bipolar disorder, cyclothymic personality, schizophrenia, peptic ulcer, irritable bowel syndrome, ulcerative colitis, Crohn's disease, diarrhea, constipation, post-operative ileus, stress-associated gastrointestinal disorders, nervous vomiting, Alzheimer's disease, senile dementia of Alzheimer's type, neurodegenerative disease, multi-infarct dementia, senile dementia, anorexia nervosa, eating disorder, obesity, diabetes, alcohol dependence, pharmacophilia, drug withdrawal symptoms, alcohol withdrawal symptoms, sleep disorder, insomnia, migraine, stress-induced headache, muscle contraction induced headache, ischemic neuronal damage, excitotoxic neuronal damage, stroke, progressive supranuclear palsy, amyotrophic lateral sclerosis, multiple sclerosis, muscular spasm, chronic fatigue syndrome, psychosocial dwarfism, epilepsy, head trauma, spinal cord injury, cheirospasm, spasmodic torticollis, cervicobrachial syndrome, primary glaucoma, Meniere's syndrome, autonomic imbalance, alopecia, neurosis, hypertension, cardiovascular disorder, tachycardia, congestive heart failure, hyperventilation syndrome, bronchial asthma, apneusis, sudden infant death syndrome, inflammatory disorder, pain, allergosis, impotence, menopausal disorder, fertilization disorder, infertility, cancer, HIV infection-related immune dysfunction, stress-induced immune dysfunction, hemorrhagic stress, Cushing's syndrome, thyroid function disorder, encephalomyelitis, acromegaly, incontinence, osteoporosis, and the like. The compounds of the present invention are effective for treatment or prevention of the aforementioned diseases.

The term "neurodegenerative disease" as used throughout the present specification refers to either acute degenerative disease or chronic degenerative disease, and specifically it includes, for example, neuropathies such as subarachnoid hemorrhage, acute stage cerebrovascular disorder, etc. and Alzheimer's disease, Parkinson's disease, Huntington's chorea, amyotrophic lateral sclerosis, spinocerebellar degeneration, etc. The term "eating disorder" as used throughout the present specification refers to hyperphagia, cibophobia and the like. The term "cardiovascular disorder" as used throughout the present specification refers to angina pectoris nervosa and the like. The term "inflammatory disorder" as used throughout the present specification refers to, for example, rheumatic arthritis, osteoarthritis, lumbago and the like, and the term "allergosis" refers to, for example, atopic dermatitis, eczema, hives, psoriasis and the like.

Throughout the present specification, "n-" signifies "normal", "sec-" signifies "secondary" and "tert-" and "t-" both signify "tertiary".

[Definition of $R^1$]

$R^1$ is a group represented by the formula $-G^{1z}-R^{1z}$ (wherein $G^{1z}$ is a single bond, oxygen or sulfur, and $R^{1z}$ is methyl or ethyl) or methoxymethyl, with methyl, ethyl, methoxy, methylthio, ethoxy and methoxymethyl being preferred, ethyl, methoxy and methylthio being more preferred, and ethyl being even more preferred.

[Definitions of $R^5$ and $R^6$]

$R^5$ and $R^6$ are each independently hydrogen, t-butoxycarbonyl or a group represented by the formula $—X^{6b}-X^{7b}$ (wherein $X^{6b}$ is methylene; and $X^{7b}$ is $C_{1-6}$ alkyl, $C_{3-8}$ cycloalkyl, tetrahydropyran-yl or tetrahydrofuran-yl). Preferably, $R^5$ and $R^6$ are each independently n-propyl, n-butyl, (cyclobutyl)methyl, cyclopropylmethyl, (tetrahydropyranyl)methyl or (tetrahydrofuranyl)methyl. More preferably, $R^5$ and $R^6$ are each independently cyclopropylmethyl, (4-tetrahydropyranyl)methyl, (3-tetrahydrofuranyl)methyl or (2-tetrahydrofuranyl)methyl. Even more preferably, $R^5$ is cyclopropylmethyl or (4-tetrahydropyranyl)methyl, and most preferably $R^5$ is cyclopropylmethyl and $R^6$ is (4-tetrahydropyranyl)methyl.

[Definitions of $R^{40}$, $R^{41}$ and $R^{42}$]

Two of $R^{40}$, $R^{41}$ and $R^{42}$ are $C_{1-6}$ alkoxy while the remaining one is a group represented by the formula $—V^{1a}—V^{2a}$ (wherein $V^{1a}$ is a single bond, $—CO—$, $C_{1-6}$ alkylene, $C_{2-6}$ alkenylene or $C_{2-6}$ alkynylene; and $V^{2a}$ is hydrogen, hydroxyl, $C_{1-6}$ alkyl optionally having 1-3 substituents selected from Substituent Group B above, $C_{1-6}$ alkoxy optionally having 1-3 substituents selected from Substituent Group B above, a group represented by the formula $—N(R^{3c})R^{3d}$ (wherein $R^{3c}$ and $R^{3d}$ are each independently hydrogen or $C_{1-6}$ alkyl optionally having 1-3 substituents selected from Substituent Group B above), methanesulfonyloxy, p-toluenesulfonyloxy, pyrrolidinyl, piperazinyl, piperidyl, morpholinyl, $C_{3-8}$ cycloalkyl, tetrahydropyran-yl or tetrahydrofuran-yl).

Preferably, two of $R^{40}$, $R^{41}$ and $R^{42}$ are methoxy. More preferably, $R^{40}$ and $R^{42}$ are methoxy.

[Definition of $R^{43}$]

$R^{43}$ is $C_{1-6}$ alkyl optionally having 1-3 substituents selected from Substituent Group B above. Preferably, $R^{43}$ is methyl optionally having 1-3 substituents selected from Substituent Group B above or ethyl optionally having 1-3 substituents selected from Substituent Group B above, more preferably methyl optionally having 1-3 substituents selected from Substituent Group B above, and even more preferably methyl.

[Definitions of $R^{44}$ and $R^{45}$]

$R^{44}$ and $R^{45}$ are each independently hydrogen, methyl or ethyl. Preferably, $R^{44}$ and $R^{45}$ are each independently hydrogen or methyl, and even more preferably $R^{44}$ and $R^{45}$ are both hydrogen.

[Definition of $R^{1t}$]

$R^{1t}$ is methoxy, methylthio, methyl, ethyl or methoxymethyl. $R^{1t}$ is preferably methoxy, methylthio or ethyl, and more preferably ethyl.

[Definitions of $R^{46}$ and $R^{47}$]

$R^{46}$ and $R^{47}$ are each $C_{1-6}$ alkyl. Preferably, $R^{46}$ and $R^{47}$ are both methyl.

[Definition of $V^{1c}$]

$V^{1c}$ is $C_{1-6}$ alkylene. Preferably, $V^{1c}$ is methylene.

[Definition of M]

M is a group represented by the formula:

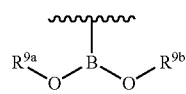

(wherein $R^{9a}$ and $R^{9b}$ are each independently hydrogen or $C_{1-6}$ alkyl, or $R^{9a}$ and $R^{9b}$ bond together to form 1,2-ethylene, 1,3-propylene or 2,3-dimethyl-butane-2,3-diyl), or a group represented by the formula:

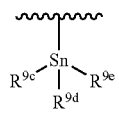

(wherein $R^{9c}$, $R^{9d}$ and $R^{9e}$ are each independently $C_{1-6}$ alkyl).

Preferably, M is a group represented by the formula:

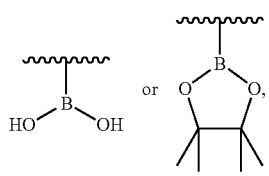

and more preferably a group represented by the formula:

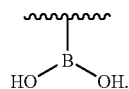

The term "pyrrolidinyl" used throughout the present specification refers to a monovalent substituent by removing a hydrogen atom from pyrrolidine, and specifically there may be mentioned 1-pyrrolidinyl, 2-pyrrolidinyl or 3-pyrrolidinyl.

The term "piperazinyl" used throughout the present specification refers to a monovalent substituent by removing a hydrogen atom from piperazine, and specifically there may be mentioned 1-piperazinyl, 2-piperazinyl, 3-piperazinyl or 4-piperazinyl.

The term "piperidyl" used throughout the present specification refers to a monovalent substituent by removing a hydrogen atom from piperidine, and specifically there may be mentioned 1-piperidyl, 2-piperidyl, 3-piperidyl or 4-piperidyl.

The term "morpholinyl" used throughout the present specification refers to a monovalent substituent by removing a hydrogen atom from morpholine, and specifically there may be mentioned 2-morpholinyl, 3-morpholinyl or 4-morpholinyl.

The term "tetrahydropyran-yl" used throughout the present specification refers to a monovalent substituent by removing a hydrogen atom from tetrahydropyran, and specifically there may be mentioned tetrahydropyran-2-yl, tetrahydropyran-3-yl or tetrahydropyran-4-yl. Preferably it is tetrahydropyran-4-yl, which is represented by the formula:

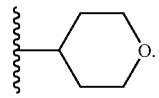

The term "tetrahydrofuran-yl" used throughout the present specification refers to a monovalent substituent by removing a hydrogen atom from tetrahydrofuran, and specifically there may be mentioned tetrahydrofuran-2-yl or tetrahydrofuran-3-yl. Preferably it is tetrahydrofuran-3-yl, which is represented by the formula:

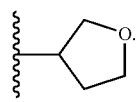

(4-Tetrahydropyranyl)methyl used throughout the present specification refers to methyl substituted with aforementioned tetrahydropyran-4-yl.

(2-Tetrahydrofuranyl)methyl used throughout the present specification refers to methyl substituted with aforementioned tetrahydrofuran-2-yl.

(3-Tetrahydrofuranyl)methyl used throughout the present specification refers to methyl substituted with aforementioned tetrahydrofuran-3-yl.

Halogen in the present specification refers to fluorine, chlorine, bromine, iodine and the like, with fluorine, chlorine or bromine being preferred.

$C_{1-6}$ alkyl in the present specification refers to linear or branched alkyl of 1 to 6 carbon, and are preferably methyl, ethyl, n-propyl, iso-propyl, n-butyl, iso-butyl, sec-butyl, tert-butyl, n-pentyl, 1,1-dimethylpropyl, 1,2-dimethylpropyl, 2,2-dimethylpropyl, 1-ethylpropyl, 2-ethylpropyl, n-hexyl, 1-methyl-2-ethylpropyl, 1-ethyl-2-methylpropyl, 1,1,2-trimethylpropyl, 1-propylpropyl, 1-methylbutyl, 2-methylbutyl, 1,1-dimethylbutyl, 1,2-dimethylbutyl, 2,2-dimethylbutyl, 1,3-dimethylbutyl, 2,3-dimethylbutyl, 2-ethylbutyl, 2-methylpentyl, 3-methylpentyl, or the like, more preferably methyl, ethyl, n-propyl, iso-propyl or tert-butyl, and even more preferably methyl, ethyl or iso-propyl.

$C_{2-6}$ alkenyl in the present specification refers to linear or branched alkenyl of 2 to 6 carbon, and preferred examples are vinyl, allyl, 1-propenyl, 2-propenyl, isopropenyl, 2-methyl-1-propenyl, 3-methyl-1-propenyl, 2-methyl-2-propenyl, 3-methyl-2-propenyl, 1-butenyl, 2-butenyl, 3-butenyl, 1-pentenyl, 1-hexenyl, 1,3-hexanedienyl and 1,6-hexanedienyl.

$C_{2-6}$ alkynyl in the present specification refers to alkynyl of 2 to 6 carbon, and preferred examples are ethynyl, 1-propynyl, 2-propynyl, 1-butynyl, 2-butynyl, 3-butynyl, 3-methyl-1-propynyl, 1-ethynyl-2propynyl, 2-methyl-3-propynyl, 1-pentynyl, 1-hexynyl, 1,3-hexanediynyl and 1,6-hexanediynyl.

The term "$C_{1-6}$ alkylene" used throughout the present specification refers to a divalent group derived by removing another hydrogen atom from the aforementioned "$C_{1-6}$ alkyl", and as specific examples there may be mentioned methylene, ethylene, methylethylene, propylene, ethylethylene, 1,1-dimethylethylene, 1,2-dimethylethylene, trimethylene, 1-methyltrimethylene, 1-ethyltrimethylene, 2-methyltrimethylene, 1,1-dimethyltrimethylene, tetramethylene, pentamethylene and hexamethylene, preferably methylene and 1,2-ethylene, and more preferably methylene.

The term "$C_{2-6}$ alkenylene" used through the present specification refers to a divalent group derived by removing another hydrogen atom from the aforementioned "$C_{2-6}$ alkenyl", and as specific examples there may be mentioned vinylene, propenylene, butenylene, pentenylene and hexenylene, preferably vinylene, propenylene, butenylene, pentenylene, even more preferably vinylene, propenylene and butenylene, and even more preferably 1,2-vinylene and 1,3-propenylene.

The term "$C_{2-6}$ alkynylene" used throughout the present specification refers to a monovalent group derived by removing another hydrogen atom from the aforementioned "$C_{2-6}$ alkynylene", and as specific examples there may be mentioned ethynylene, propynylene, butynylene, pentynylene and hexynylene, preferably ethynylene, propynylene, butynylene and pentynylene, more preferably ethynylene, propynylene and butynylene, even more preferably ethynylene and propynylene, and most preferably ethynylene.

$C_{3-8}$ cycloalkyl in the present specification refers to a cyclic aliphatic hydrocarbon group of 3 to 8 carbon, and as examples there may be mentioned cyclopropyl, cyclobutyl, cyclopentyl, cyclohexyl, cycloheptyl and cyclooctyl, preferably cyclopropyl, cyclobutyl and cyclopentyl, and more preferably cyclopropyl.

$C_{1-6}$ alkoxy in the present specification refers to oxygen bonded with the aforementioned "$C_{1-6}$ alkyl", and as examples there may be mentioned methoxy, ethoxy, n-propoxy, iso-propoxy, sec-propoxy, n-butoxy, iso-butoxy, sec-butoxy, tert-butoxy, n-pentyloxy, iso-pentyloxy, sec-pentyloxy, n-hexoxy, iso-hexoxy, 1,1-dimethylpropyloxy, 1,2-dimethylpropoxy, 2,2-dimethylpropyloxy, 2-ethylpropoxy, 1-methyl-2-ethylpropoxy, 1-ethyl-2-methylpropoxy, 1,1,2-trimethylpropoxy, 1,1-dimethylbutoxy, 1,2-dimethylbutoxy, 2,2-dimethylbutoxy, 2,3-dimethylbutyloxy, 1,3-dimethylbutyloxy, 2-ethylbutoxy, 1,3-dimethylbutoxy, 2-methylpentoxy, 3-methylpentoxy and hexyloxy, preferably methoxy, ethoxy, n-propoxy, iso-propoxy, sec-propoxy, n-butoxy, iso-butoxy, sec-butoxy and tert-butoxy, and more preferably methoxy.

The phrase "optionally substituted" used throughout the present specification means optionally substituted with 1-3 substituents selected from Substituent Group B above.

The phrase "a compound . . . , a salt thereof or a hydrate of the foregoing" used throughout the present specification refers to (i) compound (I), (ii) a salt of compound (I), (iii) a hydrate of compound (I) or (iv) a hydrate of a salt of compound (I), and it is preferably (i) compound (I) or (ii) a salt of compound (I), and more preferably a salt of compound (I).

The term "hydrate" used throughout the present specification refers to the state of a compound hydrated (solvated) with water or the state of a salt of the compound hydrated (solvated) with water. Preferably a hydrate is formed in an appropriate ratio of 0.1 to 8 molecules of water to 1 molecule of a compound or salt of the compound, and more preferably a hydrate is formed in an appropriate ratio of 0.3 to 3 molecules of water to 1 molecule of a compound.

The salts of compound (I) of the present invention are not particularly restricted so long as they are salts formed with the compounds of the invention, and for example, there may be mentioned salts with inorganic acids, salts with organic acids and salts with acidic amino acids, among which pharmacologically acceptable salts are preferred. The acids may form salts at appropriate ratios of 0.1-5 molecules to 1 molecule of the compound.

As preferred examples of salts with inorganic acids there may be mentioned salts of hydrochloric acid, hydrobromic acid, sulfuric acid, nitric acid, phosphoric acid and the like, and as preferred examples of salts with organic acids there may be mentioned salts of acetic acid, succinic acid, fumaric acid, maleic acid, tartaric acid, citric acid, lactic acid, stearic acid, benzoic acid, benzenesulfonic acid, ethanesulfonic acid, methanesulfonic acid, tosylic acid (p-toluenesulfonic acid) and the like.

As preferred examples of salts with acidic amino acids there may be mentioned salts with aspartic acid, glutamic acid and the like.

As preferred examples of salts of compound (I) of the invention there may be mentioned salts with hydrochloric acid, sulfuric acid, benzenesulfonic acid, ethanesulfonic acid, methanesulfonic acid, tosylic acid or hydrobromic acid, and as more preferred examples there may be mentioned salts with tosylic acid.

The compounds (except (i) 4-(hydroxymethyl)-2,6-dimethoxyphenylboric acid and (ii) 4-(((t-butyldiphenylsilyl)oxy)methyl)-2,6-dimethoxyphenylboric acid) represented by the following formula, salts thereof and hydrates of the foregoing are highly useful as synthesis intermediates for compound (I) according to the invention.

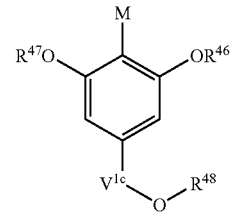

[wherein $R^{48}$ is hydrogen, $C_{1-6}$ alkyl optionally having 1-3 substituents selected from Substituent Group B below, benzyl optionally having 1-3 substituents selected from Substituent Group B below, 2-tetrahydropyranyl or a group represented by the formula:

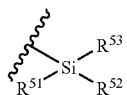

(wherein $R^{51}$, $R^{52}$ and $R^{53}$ are each independently $C_{1-6}$ alkyl or phenyl); $R^{46}$ and $R^{47}$ are each independently $C_{1-6}$ alkyl; $V^{1c}$ is $C_{1-6}$ alkylene; M is a group represented by the formula:

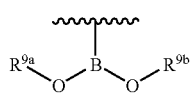

(wherein $R^{9a}$ and $R^{9b}$ are each independently hydrogen or $C_{1-6}$ alkyl, or $R^{9a}$ and $R^{9b}$ bond together to form 1,2-ethylene, 1,3-propylene or 2,3-dimethyl-butane-2,3-diyl), or a group represented by the formula:

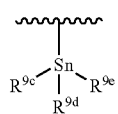

(wherein $R^{9c}$, $R^{9d}$ and $R^{9e}$ are each independently $C_{1-6}$ alkyl), wherein Substituent Group B is the group consisting of fluorine atom, chlorine atom, bromine atom, cyano, $C_{1-6}$ alkoxy, pyrrolidinyl, piperazinyl, piperidyl, morpholinyl, $C_{3-8}$ cycloalkyl, tetrahydropyran-yl and tetrahydrofuran-yl].

The following compounds, salts thereof and hydrates of the foregoing are highly useful as synthesis intermediates for compound (I) according to the invention.

[1] Compounds according to compound (I) wherein $-NR^5R^6$ is:

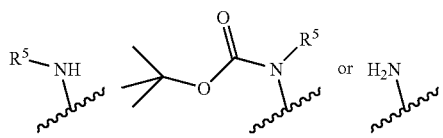

[2] Compounds according to compound (I) wherein $V^{2a}$ is a group represented by the formula:

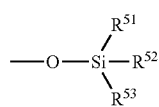

(wherein $R^{51}$, $R^{52}$ and $R^{53}$ are each independently $C_{1-6}$ alkyl or phenyl), methanesulfonyloxy or p-toluenesulfonyloxy.

Representative production schemes for the compounds represented by formula (I) above according to the invention will now be described. In the production schemes indicated below, $R^1$, $R^5$, $R^6$, $R^{9a}$, $R^{9b}$, $R^{9c}$, $R^{9d}$, $R^{9e}$, $R^{43}$, $R^{44}$, $R^{45}$, $R^{46}$, $R^{47}$, $R^{48}$ and M have the same respective definitions given above, X is halogen (e.g., fluorine, chlorine, bromine or iodine), Ar is phenyl optionally substituted with 1-3 groups represented by the formula $-V^{1a}-V^{2a}$ (where $V^{1a}$ and $V^{2a}$ have the same respective definitions given above), $R^{1c}$ and $R^{1d}$ are each $C_{1-6}$ alkyl, $C_{2-6}$ alkenyl, $C_{2-6}$ alkynyl or $C_{3-8}$ cycloalkyl (each of the foregoing groups are optionally substituted), $R^{ca}$ is optionally substituted $C_{1-6}$ alkyl or optionally substituted benzyl, X' is bromine, iodine or hydrogen, A is nitroso or nitro, a group represented by $Prot^N$ is an amino-protecting group, a group represented by $Prot^O$ is a hydroxyl-protecting group, B is Ar or X [wherein Ar and X have the same respective definitions given above], Lev is a leaving group such as X [wherein X has the same definition given above] or sulfonate (e.g., p-toluenesulfonyloxy or methanesulfonyloxy), $R^{11a}$, $R^{11b}$, $R^{11c}$ and $R^{11d}$ are each $C_{1-6}$ alkyl, $C_{3-8}$ cycloalkyl, $C_{3-8}$ cycloalkyl-$C_{1-6}$ alkyl, $C_{2-6}$ alkenyl or $C_{2-6}$ alkynyl, with $R^{11b}$ and $R^{11c}$ optionally bonding together to form a 4- to 8-membered ring and the 4- to 8-membered ring being a substituent optionally containing multiple N, O or S atoms in the ring, and n is an integer of 1-6. The term "room temperature" used hereunder refers to a temperature in the range of 10 to 40° C.

Production Scheme 1

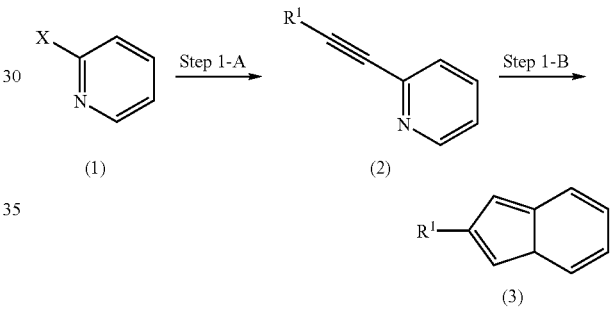

Step 1-A: A 2-halogenopyridine derivative represented by formula (1) may be reacted with an acetylene derivative in the presence of a palladium catalyst and copper (I) iodide, in the presence of a base and either in a solvent or without a solvent, at a temperature of 0° C. to 250° C., to afford an acetylene derivative (2). The solvent used will differ depending on the starting materials, reagents, etc. and is not particularly restricted so long as it dissolves the starting materials to some degree without inhibiting the reaction, and preferably there may be mentioned toluene, xylene, anisole, N,N-dimethylformamide, 1,2-dimethoxyethane, tetrahydrofuran, dioxane, n-butanol, ethanol, methanol, 1-methyl-2-pyrrolidinone and water, which may be used either alone or as a mixed solvent. The base used will differ depending on the starting materials, solvents, etc. and is not particularly restricted so long as it does not inhibit the reaction, and preferably there may be mentioned potassium carbonate, sodium carbonate, cesium fluoride, potassium fluoride, sodium hydrogencarbonate, triethylamine and diethylamine. These bases may also be used as a solvent. Specific palladium or nickel catalysts will differ depending on the starting materials, solvents, etc. and are not particularly restricted so long as they do not inhibit the reaction, and preferably there may be mentioned tetrakis(triphenylphosphine)palladium (0), palladium(II) acetate/triphenylphosphine, palladium(II) chloride, tris(dibenzylideneacetone)dipalladium(0)/tri-tert-butylphosphine, dichloro[1,1'-bis(diphenylphosphine)-ferrocene]palladium(0), [1,2-bis(diphenylphosphino)ethane] dichloronickel(II) and [1,3-bis(diphenylphosphino)propane] dichloronickel(II). Preferably, the palladium catalyst is used at 0.001 to 0.2 equivalent, the acetylene derivative at 1 to 20 equivalents and the base at 1 to 20 equivalents or as the solvent.

Step 1-B: An acetylene derivative represented by formula (2) may be reacted with an N-aminating agent (for example, hydroxylamine O-sulfonate or O-mesitylenesulfonylhydroxyamine) at −50° C. to 40° C., either in a solvent or without a solvent, and the resulting N-aminopyridinium salt may be isolated through a filter or the like or used directly in the system for reaction in the presence or in the absence of a base at 0° C. to 250° C. to afford a cyclized compound represented by formula (3). The solvent used will differ depending on the starting materials, reagents, etc. and is not particularly restricted so long as it dissolves the starting materials to some degree without inhibiting the reaction, and preferably there may be mentioned toluene, xylene, anisole, N,N-dimethylformamide, 1,2-dimethoxyethane, tetrahydrofuran, dioxane, n-butanol, ethanol, methanol and 1-methyl-2-pyrrolidinone, which may be used alone or as a mixed solvent. The base used will differ depending on the starting materials, solvents, etc. and is not particularly restricted so long as it does not inhibit the reaction, and preferably there may be mentioned potassium carbonate, sodium carbonate, cesium fluoride, potassium fluoride, sodium hydrogencarbonate, triethylamine, sodium methoxide, sodium ethoxide, sodium tert-butoxide and potassium tert-butoxide. In this case, the N-aminating agent is preferably used at 1 to 3 equivalents and the base at 1 to 5 equivalents.

Production Scheme 2

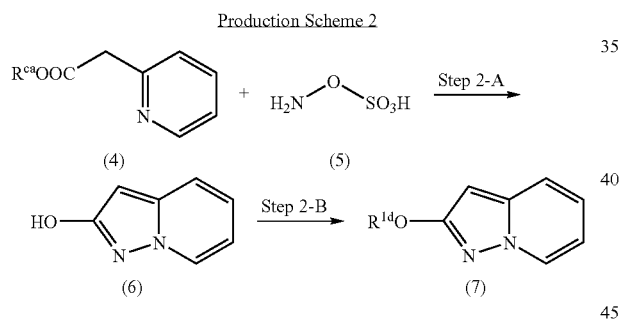

Step 2-A: A 2-pyridylacetic acid ester represented by formula (4) and hydroxylamine-O-sulfonate (5) may be reacted in a solvent in the presence or in the absence of a base, to afford 2-hydroxypyrazolo[1,5-a]pyridine represented by formula (6). The reaction temperature will usually be 0° C. to 100° C. The solvent used will differ depending on the starting materials, reagents, etc. and is not particularly restricted so long as it dissolves the starting materials to some degree without inhibiting the reaction, and preferably there may be mentioned acetone, acetic acid, methanol, ethanol and water, which may be used alone or as a mixed solvent. Hydroxylamine-O-sulfonate is preferably used at 0.1 to 2 equivalents and the base at 1 to 3 equivalents.

Step 2-B: 2-Hydroxypyrazolo[1,5-a]pyridine represented by formula (6) and an alkylating agent may be reacted in a solvent or without a solvent, in the presence or in the absence of a base, to afford a derivative represented by formula (7). The reaction temperature will usually be 0° C. to 100° C. The solvent used will differ depending on the starting materials, reagents, etc. and is not particularly restricted so long as it dissolves the starting materials to some degree without inhibiting the reaction, and preferably there may be mentioned acetone, methanol, ethanol and water, which may be used alone or as a mixed solvent. As alkylating agents there may be mentioned dimethylsulfuric acid, diethylsulfuric acid, alkyl halides, diazomethane and trimethylsilyldiazomethane. The base used will differ depending on the starting materials, solvents, etc. and is not particularly restricted so long as it does not inhibit the reaction, and preferably there may be mentioned potassium carbonate, sodium carbonate, cesium fluoride, potassium fluoride, sodium hydrogencarbonate, triethylamine, diethylamine, sodium methoxide, sodium ethoxide and potassium tert-butoxide. The alkylating agent is preferably used at 1 to 3 equivalents and the base at 1 to 15 equivalents.

Production Scheme 3

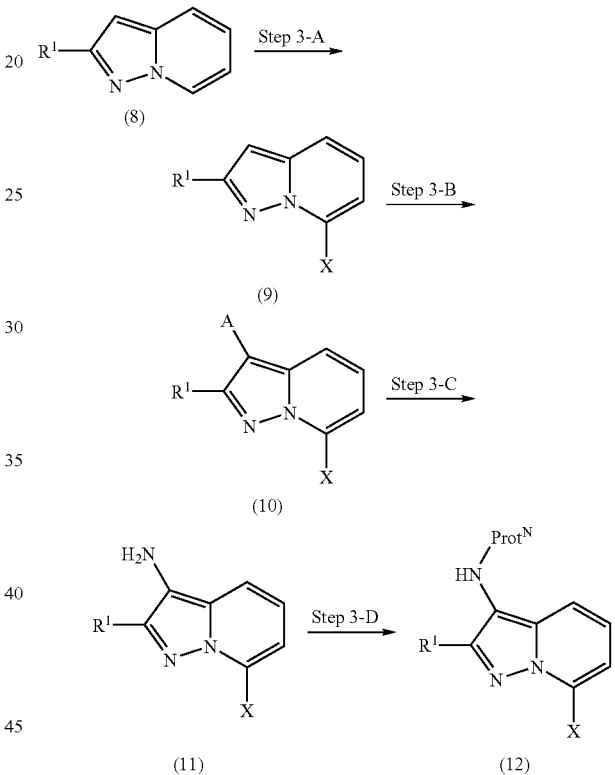

Step 3-A: A pyrazolo[1,5-a]pyridine derivative (compound (3) in Production Scheme 1 or compound (7) in Production Scheme 2, etc.), and an alkyllithium reagent (for example, n-butyllithium, sec-butyllithium, tert-butyllithium, etc.) may be reacted in an inert solvent and then further reacted with a halogenating agent, to afford a pyrazolo[1,5-a]pyridine derivative represented by formula (9) having a halogen introduced at the 7-position. The reaction temperature will usually be −100° C. to 40° C. The halogenating agent used will differ depending on the starting materials, solvents, etc. and is not particularly restricted so long as it does not inhibit the reaction, and preferably there may be mentioned bromine, iodine, N-chlorosuccinimide, N-bromosuccinimide, N-iodosuccinimide, hexachloroethane, 1,2-dibromoethane, 1,2-dibromo-1,1,2,2-tetrachloroethane, 1,2-diiodo-ethane or the like. The solvent used will differ depending on the starting materials, reagents, etc. and is not particularly restricted so long as it dissolves the starting materials to some degree without inhibiting the reaction, and preferably there may be mentioned hexane, pentane, tetrahydrofuran and diethyl ether, which may be used alone or as a mixed solvent. The alkyllithium reagent is preferably used at 1 to 2 equivalents and the halogenating agent at 1 to 3 equivalents.

Step 3-B: A pyrazolo[1,5-a]pyridine derivative represented by formula (9) and a nitrating agent may be reacted either in a solvent or without a solvent to afford a 3-nitropyrazolo[1,5-a]pyridine derivative represented by formula (10). The reaction temperature will usually be −70° C. to 200° C. The nitrating agent used will differ depending on the starting materials, solvent, etc. and is not particularly restricted so long as it does not inhibit the reaction, and preferably there may be mentioned copper nitrate trihydrate, nitric acid, fuming nitric acid, sodium nitrate, nitronium tetrafluoroborate, ammonium nitrate, and the like. The solvent used will differ depending on the starting materials, reagents, etc. and is not particularly restricted so long as it dissolves the starting materials to some degree without inhibiting the reaction, and preferably there may be mentioned acetic anhydride, acetic acid, sulfuric acid, trifluoroacetic anhydride, trifluoroacetic acid, acetonitrile, 1,2-dimethoxyethane and tetrahydrofuran, which may be used alone or as a mixed solvent. The nitrating agent is preferably used at 1 to 2 equivalents.

Alternatively, a pyrazolo[1,5-a]pyridine derivative (9) and a nitrosating agent such as sodium nitrite may be reacted either in a solvent or without a solvent to afford a 3-nitrosopyrazolo[1,5-a]pyridine derivative represented by formula (10). The reaction temperature will usually be −40° C. to 100° C. The nitrosating agent used will differ depending on the starting materials, solvents, etc. and is not particularly restricted so long as it does not inhibit the reaction, and preferably there may be mentioned sodium nitrite, isoamyl nitrite and the like. The solvent used will differ depending on the starting materials, reagents, etc. and is not particularly restricted so long as it dissolves the starting materials to some degree without inhibiting the reaction, and preferably there may be mentioned acetic anhydride, acetic acid, hydrochloric acid, sulfuric acid, trifluoroacetic anhydride, trifluoroacetic acid, acetonitrile, 1,2-dimethoxyethane, water and ethanol, which may be used alone or as a mixed solvent. The nitrosating agent is preferably used at 1 to 2 equivalents.

Step 3-C: A nitro derivative or nitroso derivative represented by formula (10) and a metal (powder) may be reacted in the presence or in the absence of an acid, either in a solvent or without a solvent, to afford a reduced compound, 3-aminopyrazolo[1,5-a]pyridine derivative (11). The reaction temperature will usually be −10° C. to 150° C. The metal (powder) used will differ depending on the starting materials, solvents, etc. and is not particularly restricted so long as it does not inhibit the reaction, and preferably there may be mentioned zinc, iron, tin(II) chloride, nickel(II) chloride and the like. The acid used will differ depending on the starting materials, solvents, etc. and is not particularly restricted so long as it does not inhibit the reaction, and preferably there may be mentioned acetic acid, hydrochloric acid, sulfuric acid, and the like. The solvent used will differ depending on the starting materials, reagents, etc. and is not particularly restricted so long as it dissolves the starting materials to some degree without inhibiting the reaction, and preferably there may be mentioned methanol, ethanol, n-butanol, water and the like, which may be used alone or as a mixed solvent. The metal (powder) is preferably used at 1 to 10 equivalents.

Alternatively, a nitro derivative or nitroso derivative represented by formula (10) may be subjected to hydrogen addition reaction in an inert solvent under a hydrogen atmosphere, in the presence or in the absence of an acid and using a metal catalyst such as Pd—C, to afford a reduced compound, 3-aminopyrazolo[1,5-a]pyridine derivative (11). The pressure of the hydrogen used will usually be 1 to 100 atmospheres and the reaction temperature usually 0° C. to 200° C. The acid and metal catalyst used will differ depending on the starting materials, solvents, etc. and are not particularly restricted so long as they do not inhibit the reaction, and as preferred acids there may be mentioned acetic acid, trifluoroacetic acid and hydrochloric acid, and as preferred metal catalysts there may be mentioned Pd—C, $PtO_2$, Pt—C and Raney-Ni. The solvent used will differ depending on the starting materials, reagents, etc. and is not particularly restricted so long as it dissolves the starting materials to some degree without inhibiting the reaction, and preferably there may be mentioned methanol, ethanol, propanol, butanol, tetrahydrofuran, 1,4-dioxane, ethyl acetate, acetone and N,N-dimethylformamide, which may be used alone or as a mixed solvent. In this reaction, the 3-aminopyrazolo[1,5-a]pyridine derivative (11) may also be obtained by reaction generating hydrogen by heating ammonium formate, etc. in a solvent such as methanol, in the presence of a metal catalyst. The metal catalyst is preferably used at 5 to 100 wt %.

Step 3-D: A 3-aminopyrazolo[1,5-a]pyridine derivative represented by formula (11) and a protecting reagent for amino groups (for example, di-tert-butyl dicarbonate) may be reacted to afford a 3-aminopyrazolo[1,5-a]pyridine derivative (12) having the amino group at 3-position protected by carbamate (for example, tert-butoxycarbonyl). The reaction may be conducted either in a solvent or without a solvent and in the presence or in the absence of a base. The reaction temperature will usually be −70° C. to 150° C. The solvent used will differ depending on the starting materials, reagents, etc. and is not particularly restricted so long as it dissolves the starting materials to some degree without inhibiting the reaction, and preferably there may be mentioned tetrahydrofuran, diethyl ether, 1,4-dioxane, dichloromethane, 1,2-dichloroethane, chloroform and N,N-dimethylformamide, which may be used alone or as a mixed solvent. The base used will differ depending on the starting materials, solvents, etc. and is not particularly restricted so long as it does not inhibit the reaction, and preferably there may be mentioned triethylamine, pyridine, diisopropylethylamine, sodium hydride, potassium carbonate, sodium carbonate, cesium carbonate, sodium hydrogencarbonate, 4-(dimethylamino)pyridine and sodium bis(trimethylsilyl) amide. As preferred examples of protecting groups to be used ("$Prot^N$" in this scheme) there may be mentioned tert-butoxycarbonyl (Boc), as well as 9-fluorenylmethoxycarbonyl (Fmoc), 2,2,2-trichloroethoxycarbonyl (Troc), and the like, whereby the amino group at 3-position is protected under reaction conditions employing reagents and solvents suitable for the protecting group. The protecting reagent for amino groups is preferably used at 1 to 3 equivalents and the base at 1 to 5 equivalents.

Production Scheme 4

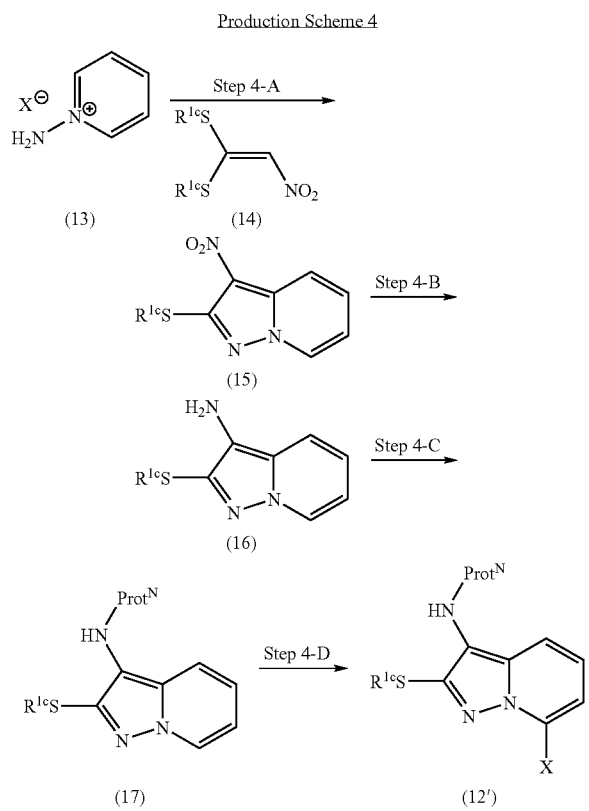

pyridine derivative represented by formula (15) (Reference: Heterocycles, 1977, 6, 379). The reaction temperature will usually be 0° C. to 200° C. The solvent used will differ depending on the starting materials, reagents, etc. and is not particularly restricted so long as it dissolves the starting materials to some degree without inhibiting the reaction, and preferably there may be mentioned ethanol, methanol, 1,2-dimethoxyethane and tetrahydrofuran, which may be used alone or as a mixed solvent. The base used will differ depending on the starting materials, reagents, etc. and is not particularly restricted so long as it does not inhibit the reaction, and preferably there may be mentioned triethylamine, diisopropylethylamine, 4-(dimethylamino)pyridine, sodium bis(trimethylsilyl)amide, and the like. The 1,1-bis(alkylthio)-2-nitroethylene derivative is preferably used at 1 to 2 equivalents and the base at 1 to 5 equivalents.

Step 4-B: A 3-nitropyrazolo[1,5-a]pyridine derivative represented by formula (15) may be reacted in the same manner as Step 3-C in Production Scheme 3 above to afford a 3-aminopyrazolo[1,5-a]pyridine derivative (16).

Step 4-C: A 3-aminopyrazolo[1,5-a]pyridine derivative represented by formula (16) may be reacted in the same manner as Step 3-D in Production Scheme 3 above to afford an amino-protected 3-aminopyrazolo[1,5-a]pyridine derivative (17).

Step 4-D: An amino-protected 3-aminopyrazolo[1,5-a]pyridine derivative represented by formula (17) may be reacted in the same manner as Step 3-A in Production Scheme 3 above to afford a pyrazolo[1,5-a]pyridine derivative (12') having halogen introduced at the 7-position.

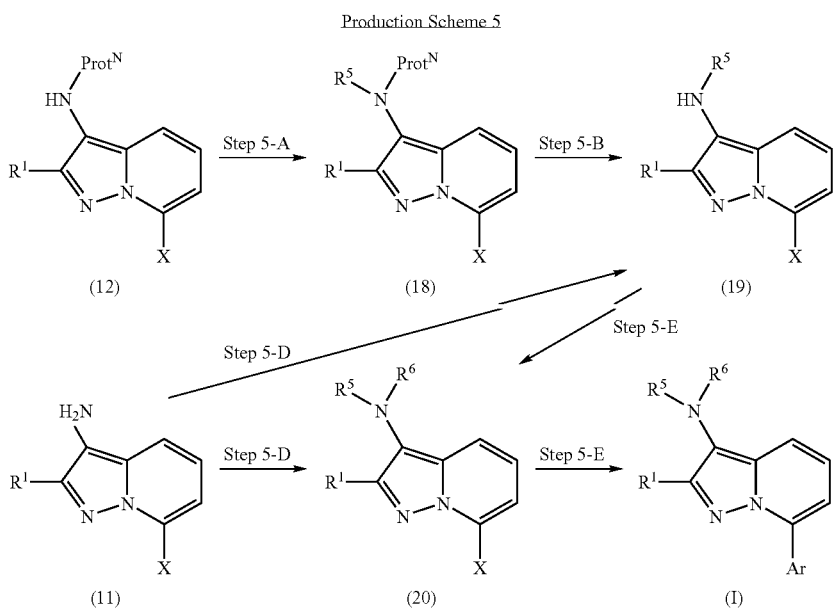

Step 4-A: A 1-aminopyridinium salt derivative represented by formula (13) and a 1,1-bis(alkylthio)-2-nitroethylene derivative represented by formula (14) may be reacted in the presence or in the absence of a base, either in a solvent or without a solvent, to afford a 3-nitropyrazolo[1,5-a]

Step 5-A: A 3-aminopyrazolo[1,5-a]pyridine derivative (12) having the amino group protected with $Prot^N$ may be reacted with an alkylating agent (for example, an optionally substituted alkyl halide or the like) to afford a pyrazolo[1,5-a]pyridine derivative represented by formula (18) having a substituent introduced at the amino group. The reaction may be conducted in a solvent or without a solvent, and in the presence or in the absence of a base. The reaction temperature will usually be −70° C. to 200° C. The solvent used will differ depending on the starting materials, reagents, etc. and is not particularly restricted so long as it dissolves the starting materials to some degree without inhibiting the reaction, and preferably there may be mentioned dichloromethane, acetone, tetrahydrofuran, diethyl ether, N,N-dimethylformamide and dimethylsulfoxide, which may be used alone or as a mixed solvent. The base used will differ depending on the starting materials, solvents, etc. and is not particularly restricted so long as it does not inhibit the reaction, and preferably there may be mentioned sodium hydride, potassium hydride, potassium carbonate, sodium carbonate, cesium carbonate, potassium hydroxide, sodium hydroxide, and the like. The alkylating agent is preferably used at 1 to 3 equivalents and the base at 1 to 5 equivalents.

Step 5-B: A 3-aminopyrazolo[1,5-a]pyridine derivative represented by formula (18) may be subjected to deprotection reaction to afford a deprotected pyrazolo[1,5-a]pyridine derivative (19). The reaction may be conducted in the presence or in the absence of a deprotecting reagent. The reaction temperature will usually be −70° C. to 200° C. The deprotecting reagent used will differ depending on the starting materials, solvents, etc. and is not particularly restricted so long as it does not inhibit the reaction, and preferably there may be mentioned hydrochloric acid, sulfuric acid, trifluoroacetic acid, methanesulfonic acid, iodotrimethylsilane, aluminum(III) chloride, trimethylsilyl triflate, and the like. When a group other than tert-butoxycarbonyl (Boc) is used as the protecting group (for example, Fmoc, Troc, etc.), the deprotection is carried out by a reaction using a reagent suitable for the protecting group. The reaction may be conducted either in a solvent or without a solvent; when it is conducted in a solvent, the solvent used will differ depending on the starting materials, reagents, etc. and is not particularly restricted so long as it dissolves the starting materials to some degree without inhibiting the reaction, and preferably there may be mentioned ethyl acetate, tetrahydrofuran, diethyl ether, 1,4-dioxane, acetonitrile, dichloromethane, chloroform, nitromethane, phenol, anisole and thiophenol, which may be used alone or as a mixed solvent. The deprotecting reagent is preferably used at 1 to 30 equivalents.

Step 5-C: A pyrazolo[1,5-a]pyridine derivative represented by formula (19) may be reacted with a carbonyl derivative (for example, diethylketone), an aldehyde derivative (for example, propionaldehyde) or a carbonyl equivalent (for example, ((1-ethoxycyclopropyl)oxy)trimethylsilane or an acetal-protected substituent) in the presence of a reducing agent to afford a pyrazolo[1,5-a]pyridine derivative represented by formula (20). The reaction temperature will usually be −10° C. to 150° C. The reaction may be conducted in the presence or in the absence of an acid, in a solvent or without a solvent, and in the presence or in the absence of an inorganic salt. The solvent used will differ depending on the starting materials, reagents, etc. and is not particularly restricted so long as it dissolves the starting materials to some degree without inhibiting the reaction, and preferably there may be mentioned tetrahydrofuran, diethyl ether, 1,2-dichloroethane, dichloromethane, chloroform, acetonitrile, ethanol, methanol and water, which may be used alone or as a mixed solvent. The acid, inorganic salt and reducing agent used will differ depending on the starting materials, solvent, etc. and are not particularly restricted so long as they do not inhibit the reaction, and preferably there may be mentioned, as acids, acetic acid, sulfuric acid and the like, as inorganic salts, sodium sulfate and the like, and as reducing agents, sodium triacetoxyborohydride, sodium borohydride, sodium cyanotrihydroborate, and the like. The carbonyl and aldehyde derivatives (including equivalents) are preferably used at 1 to 20 equivalents, the reducing agent at 1 to 5 equivalents and the inorganic salt at 1 to 30 equivalents.

Alternatively, a pyrazolo[1,5-a]pyridine derivative (19) and an acylating reagent may be reacted in the presence or in the absence of a base, in a solvent or without a solvent, to afford a pyrazolo[1,5-a]pyridine derivative (20) having the amino group acylated. The reaction temperature will usually be −20° C. to 150° C. The solvent used will differ depending on the starting materials, reagents, etc. and is not particularly restricted so long as it dissolves the starting materials to some degree without inhibiting the reaction, and preferably there may be mentioned tetrahydrofuran, diethyl ether, 1,2-dichloroethane, dichloromethane, acetonitrile, ethanol, methanol and water, which may be used alone or as a mixed solvent. The base used will differ depending on the starting materials, solvents, etc. and is not particularly restricted so long as it does not inhibit the reaction, and preferably there may be mentioned triethylamine, pyridine, diisopropylethylamine, N,N-diisopropylethylamine, 4-(dimethylamino)pyridine, sodium carbonate, potassium carbonate, sodium hydroxide, potassium hydroxide and the like. The acylating agent is preferably used at 1 to 3 equivalents and the base at 1 to 20 equivalents.

Step 5-D: A 3-aminopyrazolo[1,5-a]pyridine derivative represented by formula (11) may be reacted with a carbonyl derivative (for example, diethylketone) or an aldehyde derivative (for example, propionaldehyde) in the presence of a reducing agent such as sodium triacetoxyborohydride to afford a pyrazolo[1,5-a]pyridine derivative represented by formula (19) or formula (20). Depending on the number of moles of the carbonyl derivative or aldehyde derivative used and the reaction time, it is possible to obtain either a monosubstituted pyrazolo[1,5-a]pyridine derivative represented by formula (19) or a disubstituted pyrazolo[1,5-a]pyridine derivative represented by formula (20). The reaction may be conducted in the presence or in the absence of an acid, in a solvent or without a solvent, and in the presence or in the absence of an inorganic salt. The reaction temperature will usually be −10° C. to 150° C. The solvent used will differ depending on the starting materials, reagents, etc. and is not particularly restricted so long as it dissolves the starting materials to some degree without inhibiting the reaction, and preferably there may be mentioned tetrahydrofuran, diethyl ether, 1,2-dichloroethane, dichloromethane, chloroform, acetonitrile and water, which may be used alone or as a mixed solvent. The acid, inorganic salt and reducing agent used will differ depending on the starting materials, solvents, etc. and are not particularly restricted so long as they do not inhibit the reaction, and preferably there may be mentioned, as acids, acetic acid, sulfuric acid and the like, as inorganic salts, sodium sulfate and the like, and as reducing agents, sodium triacetoxyborohydride, sodium borohydride, sodium cyanoborohydride, and the like. The carbonyl or aldehyde derivative is preferably used at 1 to 20 equivalents, the reducing agent at 1 to 5 equivalents and the inorganic salt at 1 to 30 equivalents.

Step 5-E: A pyrazolo[1,5-a]pyridine derivative represented by formula (20) may be reacted using a metal aryl reagent or metal heteroaryl reagent and a transition metal catalyst, in the presence or in the absence of a base and in a solvent or without a solvent, to afford a pyrazolo[1,5-a]pyridine derivative (I) substituted with an aryl group or heteroaryl group at the 7-position. The reaction temperature will usually be 0° C. to 200° C. Commonly employed combinations of reagents and catalysts include arylboric acid compound/palladium catalysts (Suzuki reaction; N. Miyaura, A. Suzuki, *Chemical Reviews* 1995, 95, 2457), aryl trialkyltin compound/palladium catalysts (Stille reaction; T. N. Mitchell, *Synthesis* 1992, 803), arylzinc compound/palladium catalysts and aryl Grignard compound/nickel catalysts. The specific palladium and nickel catalyst used will differ depending on the starting materials, solvents, etc. and are not particularly restricted so long as they do not inhibit the reaction, and preferably there may be mentioned tetrakis (triphenylphosphine)palladium(0), palladium(II) acetate/ triphenylphosphine, palladium(II) chloride, tris(dibenzylideneacetone)dipalladium(0)/tri-tert-butylphosphine, dichloro[1,1'-bis(diphenylphosphine)-ferrocene]palladium (0), [1,2-bis(diphenylphosphino)ethane]dichloronickel(II), [1,3-bis(diphenylphosphino)propane]dichloronickel(II), and the like. The solvent used will differ depending on the starting materials, reagents, etc. and is not particularly restricted so long as it dissolves the starting materials to some degree without inhibiting the reaction, and preferably there may be mentioned toluene, xylene, mesitylene, anisole, N,N-dimethylformamide, 1,2-dimethoxyethane, tetrahydrofuran, 1,4-dioxane, n-butanol, ethanol, methanol, 1-methyl-2-pyrrolidinone and water, which may be used alone or as a mixed solvent. The base used will differ depending on the starting materials, solvent, etc. and is not particularly restricted so long as it does not inhibit the reaction, and preferably there may be mentioned potassium carbonate, sodium carbonate, barium hydroxide, cesium fluoride, potassium fluoride, sodium hydrogencarbonate, triethylamine, and the like. The metal aryl reagent or metal heteroaryl reagent is preferably used at 1 to 2 equivalents, the transition metal catalyst at 0.001 to 0.2 equivalent and the base at 1 to 5 equivalents.

Step 6-A: A pyrazolo[1,5-a]pyridine derivative represented by formula (12) having the amino group at 3-position protected may be reacted in the same manner as Step 5-E in Production Scheme 5 above to afford a pyrazolo[1,5-a]pyridine derivative (21) having an Ar group introduced at the 7-position.

Step 6-B: A pyrazolo[1,5-a]pyridine derivative represented by formula (21) may be reacted in the same manner as Step 5-A in Production Scheme 5 above to afford a pyrazolo[1,5-a]pyridine derivative represented by formula (22).

Step 6-C: A pyrazolo[1,5-a]pyridine derivative represented by formula (21) or (22) may be reacted in the same manner as Step 5-B in Production Scheme 5 above to afford a deprotected pyrazolo[1,5-a]pyridine derivative (23) or (24), respectively.

Step 6-D: A pyrazolo[1,5-a]pyridine derivative represented by formula (23) may be reacted in the same manner as Step 5-D in Production Scheme 5 above to afford a pyrazolo[1,5-a]pyridine derivative represented by formula (24) or (I), depending on the reaction conditions, etc.

Step 6-E: A pyrazolo[1,5-a]pyridine derivative represented by formula (24) may be reacted in the same manner as Step 5-C in Production Scheme 5 above to afford a pyrazolo[1,5-a]pyridine derivative represented by formula (I).

Production Scheme 7

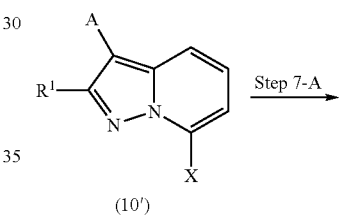

Production Scheme 6

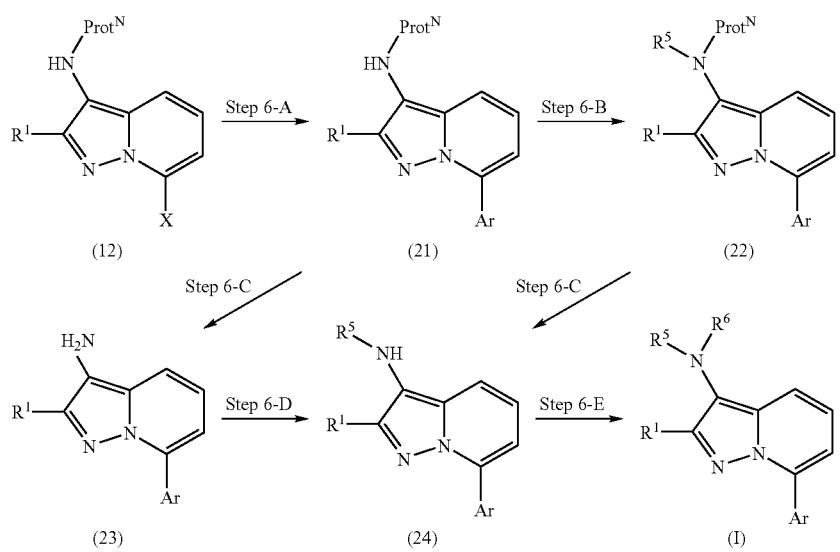

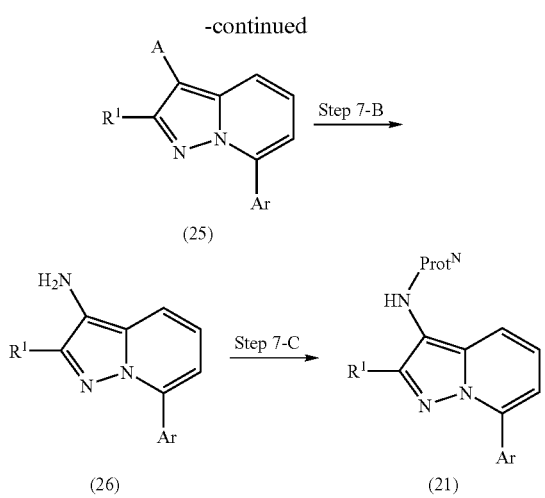

Step 7-A: A 3-nitropyrazolo[1,5-a]pyridine derivative or 3-nitrosopyrazolo[1,5-a]pyridine derivative represented by formula (10') may be reacted in the same manner as Step 5'-E in Production Scheme 5 above to afford a pyrazolo[1,5-a]pyridine derivative (25) having an Ar group substituted at the 7-position.

Step 7-B: A 3-nitropyrazolo[1,5-a]pyridine derivative or 3-nitrosopyrazolo[1,5-a]pyridine derivative represented by formula (25) may be reacted in the same manner as Step 3-C in Production Scheme 3 above to afford a reduced compound, a pyrazolo[1,5-a]pyridine derivative (26).

Step 7-C: A 3-nitropyrazolo[1,5-a]pyridine derivative or 3-nitrosopyrazolo[1,5-a]pyridine derivative represented by formula (26) may be reacted in the same manner as Step 3-D in Production Scheme 3 above to afford a pyrazolo[1,5-a]pyridine derivative (21) having the amino group at 3-position protected.

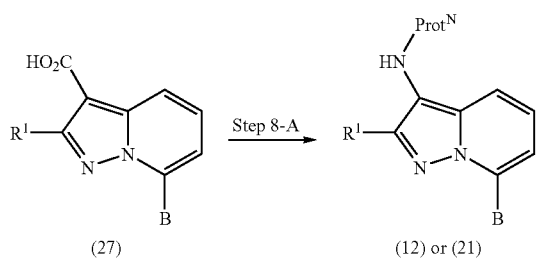

Step 8-A: A carboxylic acid derivative represented by formula (27) and an azidation agent (for example, diphenylphosphoryl azide (DPPA) or sodium azide) may be reacted either in a solvent or without a solvent and in the presence or in the absence of a base, at a temperature of −70° C. to 250° C., to produce an acid azide derivative, and the acid azide derivative subsequently heated at 40° C. to 250° C. for rearrangement reaction such as Curtius rearrangement to generate an isocyanate in the system, and reaction then conducted with tert-butanol or the like, to afford a 3-aminopyrazolo[1,5-a]pyridine derivative (12) or (21) protected with a carbamate group such as tert-butoxycarbonyl (Boc). The solvent used will differ depending on the starting materials, reagents, etc. and is not particularly restricted so long as it dissolves the starting materials to some degree without inhibiting the reaction, and preferably there may be mentioned toluene, xylene, diphenyl ether, tert-butanol, tetrahydrofuran, dioxane, acetonitrile and N,N-dimethylformamide, which may be used alone or as a mixed solvent. The base used will differ depending on the starting materials, solvents, etc. and is not particularly restricted so long as it does not inhibit the reaction, and preferably there may be mentioned triethylamine, diisopropylethylamine, 4-(dimethylamino)pyridine, pyridine, and the like. As an alternative method, the aforementioned acid azide derivative may be synthesized by converting the carboxylic acid derivative (27) to an acid chloride or mixed acid anhydride and then reacting it with an azidation agent (for example, sodium azide, trimethylsilyl azide, etc.). As another alternative method, the target compound (12) or (21) may be obtained by Hofmann rearrangement or Schmidt rearrangement. The azidation agent is preferably used at 1 to 3 equivalents, the base at 1 to 5 equivalents, and the tert-butanol either at 1 to 50 equivalents or as the solvent.

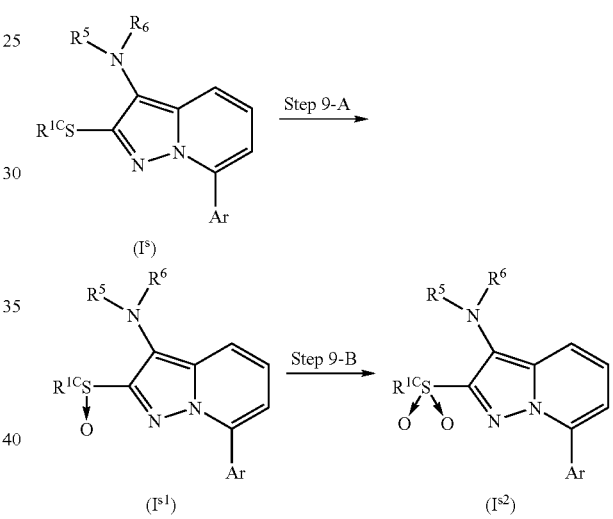

Step 9-A: A sulfide derivative represented by formula (I$^s$) may be oxidized using an oxidizing agent such as m-chloroperbenzoic acid either in a solvent or without a solvent, to afford a sulfoxide derivative (I$^{s1}$). The reaction temperature will usually be −70° C. to 150° C. The solvent used will differ depending on the starting materials, reagents, etc. and is not particularly restricted so long as it dissolves the starting materials to some degree without inhibiting the reaction, and preferably there may be mentioned acetone, acetic acid, trifluoroacetic acid, dichloromethane, chloroform, toluene, nitromethane, methanol, ethanol and water, which may be used alone or as a mixed solvent. As oxidizing agents to be used there may be mentioned m-chloroperbenzoic acid, trifluoroperacetic acid, bis(trimethylsilyl)peracids, sodium periodate, dinitrogen tetraoxide, acid mixture of nitric acid-sulfuric acid, chromic acid, and the like. The oxidizing agent is preferably used at 1 to 2 equivalents.

Step 9-B: A sulfoxide derivative (I$^{s1}$) may be oxidized using an oxidizing agent such as m-chloroperbenzoic acid either in a solvent or without a solvent, to afford a sulfone derivative (I$^{s1}$) The reaction temperature will usually be −70° C. to 150° C. The solvent used will differ depending on the starting materials, reagents, etc. and is not particularly restricted so long as it dissolves the starting materials to some degree without inhibiting the reaction, and preferably there may be mentioned acetone, acetic acid, trifluoroacetic acid, dichloromethane, chloroform, toluene, methanol, ethanol and water, which may be used alone or as a mixed solvent. As oxidizing agents to be used there may be mentioned m-chloroperbenzoic acid, chromic acid, osmium tetraoxide, potassium permanganate, and the like. The oxidizing agent is preferably used at 1 to 2 equivalents.

inert solvent and then reacted with a boric acid ester or the like to afford a boric acid derivative represented by formula (B-1). The reaction temperature will usually be −100° C. to 80° C. The boric acid ester used will differ depending on the starting materials, solvents, etc. and is not particularly restricted so long as it does not inhibit the reaction, and preferably there may be mentioned trimethyl borate, triethyl borate, triisopropyl borate, 2-methoxy-4,4,5,5-tetramethyl-1,3,2-dioxaborane, and the like. The inert solvent used will

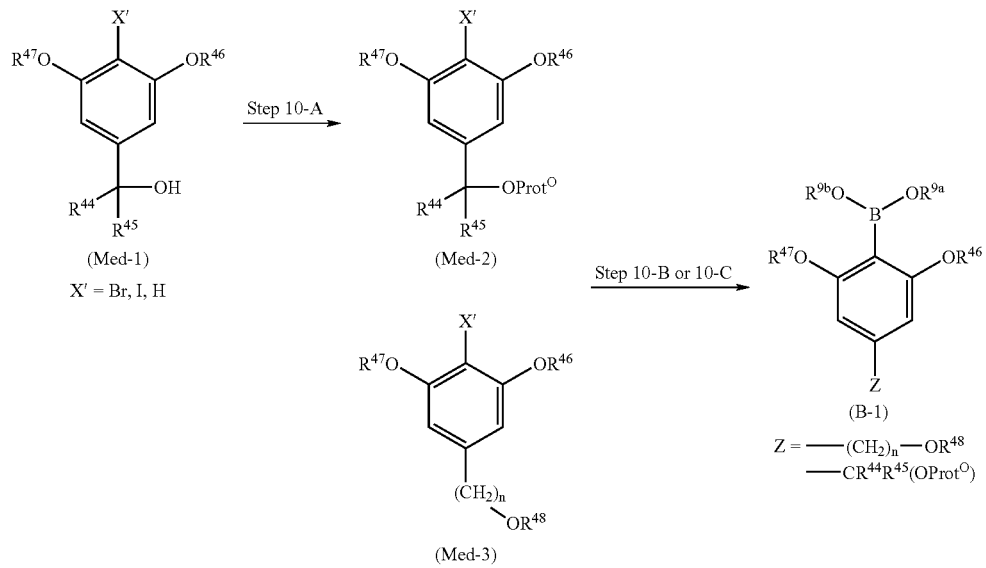

Step 10-A: A benzyl alcohol derivative represented by formula (Med-1) and a substituent-introducing agent which can be used as a protecting group for hydroxyl (for example, a silylating agent or an optionally substituted alkylating agent) may be reacted in a solvent or without a solvent and in the presence or in the absence of a base, to afford a hydroxyl-protected derivative represented by formula (Med-2). The reaction temperature will usually be −70° C. to 200° C. The solvent used will differ depending on the starting materials, reagents, etc. and is not particularly restricted so long as it dissolves the starting materials to some degree without inhibiting the reaction, and preferably there may be mentioned tetrahydrofuran, diethyl ether, N,N-dimethylformamide and dimethylsulfoxide, which may be used alone or as a mixed solvent. As examples of bases to be used there may be mentioned sodium hydride, potassium hydride, potassium carbonate, sodium carbonate, cesium carbonate, potassium hydroxide, sodium hydroxide, triethylamine, pyridine, imidazole, 2,6-lutidine, and the like. As silylating agents there may be mentioned trimethylsilyl chloride, tert-butyldimethylsilyl chloride and tert-butyldiphenylsilyl chloride. As substituted alkylating agents there may be mentioned methoxymethyl chloride and benzyl chloride. In this case, the substituent-introducing agent may be used at 1 to 3 equivalents and the base at 1 to 5 equivalents.

Step 10-B: A compound represented by formula (Med-2) or (Med-3) and an alkyllithium reagent (for example, n-butyllithium, sec-butyllithium, tert-butyllithium, etc.) or a Grignard reagent (for example, methylmagnesium bromide, isopropylmagnesium bromide, etc.) may be reacted in an differ depending on the starting materials, reagents, etc. and is not particularly restricted so long as it dissolves the starting materials to some degree without inhibiting the reaction, and preferably there may be mentioned hexane, pentane, tetrahydrofuran and diethyl ether, which may be used alone or as a mixed solvent. When an alkyllithium reagent is used, a metal complex-forming agent (for example, N,N,N',N'-tetramethylethylenediamine, hexamethylphosphorous triamide (HMPA), etc.) may also be added to increase the reactivity. The alkyllithium reagent or Grignard reagent is preferably used at 1 to 2 equivalents, the boric acid ester at 1 to 3 equivalents and the metal complex-forming agent at 1 to 2 equivalents.

Step 10-C: A compound represented by formula (Med-2) or (Med-3) may be subjected to coupling reaction with alkoxydiboron or pinacolborane in a solvent or without a solvent and in the presence or in the absence of a base, using a transition metal catalyst such as palladium, to afford compound (B-1). The reaction temperature will usually be 0° C. to 250° C. The inert solvent used will differ depending on the starting materials, reagents, etc. and is not particularly restricted so long as it dissolves the starting materials to some degree without inhibiting the reaction, and preferably there may be mentioned toluene, xylene, 1,4-dioxane, dichloroethane, acetonitrile, N,N-dimethylformamide and dimethylsulfoxide, which may be used alone or as a mixed solvent. The base used will differ depending on the starting materials, reagents, etc. and is not particularly restricted so long as it does not inhibit the reaction, and preferably there may be mentioned triethylamine, diisopropylethylamine, pyridine, potassium acetate, 1,8-diazabicyclo[5.4.0]-7-undecene (DBU), and the like. The alkoxydiboron used will differ depending on the starting materials, reagents, etc. and is not particularly restricted so long as it does not inhibit the reaction, and preferably there may be mentioned, bis(pinacolato)diboron, bis(neopentyl glycolato)diboron, bis(hexylene glycolato)diboron, and the like. The palladium catalyst used will also differ depending on the starting materials, reagents, etc. and is not particularly restricted so long as it does not inhibit the reaction, and preferably there may be mentioned tetrakis(triphenylphosphine)palladium(0), palladium(II) acetate/triphenylphosphine, palladium(II) chloride, tris(dibenzylideneacetone)dipalladium(0)/tri-tert-butylphosphine, dichloro[1,1'-bis(diphenylphosphine)-ferrocene]palladium(0), [1,2-bis(diphenylphosphino)ethane]dichloronickel(II), [1,3-bis(diphenylphosphino)propane]dichloronickel(II), and the like. The transition metal catalyst is preferably used at 0.001 to 0.2 equivalent, the base at 1 to 20 equivalents and the alkoxyborane or pinacolborane at 1 to 3 equivalents.

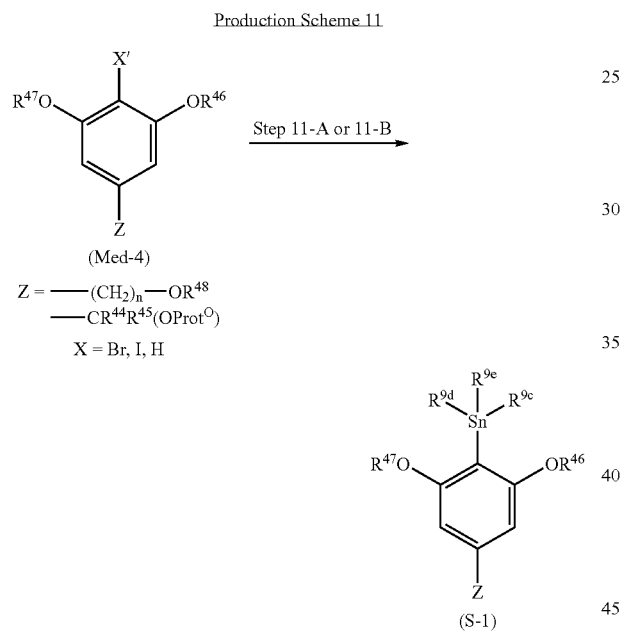

Step 11-A: A derivative represented by formula (Med-4) and an alkyllithium reagent (for example, n-butyllithium, sec-butyllithium, tert-butyllithium, etc.) or Grignard reagent (for example, methylmagnesium bromide, isopropylmagnesium bromide, etc.) may be reacted in an inert solvent, and then reacted with a trialkyltin halide reagent to afford a trialkyltin derivative represented by formula (S-1). The reaction temperature will usually be −100° C. to 50° C. The trialkyltin halide reagent used will differ depending on the starting materials, solvents, etc. and is not particularly restricted so long as it does not inhibit the reaction, and preferably there may be mentioned trimethyltin chloride, triethyltin chloride, tributyltin chloride, trimethyltin bromide, triethyltin bromide and tributyltin bromide. The inert solvent used will differ depending on the starting materials, reagents, etc. and is not particularly restricted so long as it dissolves the starting materials to some degree without inhibiting the reaction, and preferably there may be mentioned hexane, pentane, tetrahydrofuran and diethyl ether, which may be used alone or as a mixed solvent. When an alkyllithium reagent is used, a metal complex-forming agent (for example, N,N,N',N'-tetramethylethylenediamine, hexamethylphosphorous triamide (HMPA), etc.) may also be added to increase the reactivity. The alkyllithium reagent or Grignard reagent is preferably used at 1 to 2 equivalents, the metal complex-forming agent at 1 to 2 equivalents and the trialkyltin halide at 1 to 2 equivalents.

Step 11-B: A compound represented by formula (Med-4) may be subjected to coupling reaction with hexamethylditin (IV), bis(tributyltin(IV) or the like in the same manner as Step C in Production Scheme 10, to afford a trialkyltin derivative represented by formula (S-1).

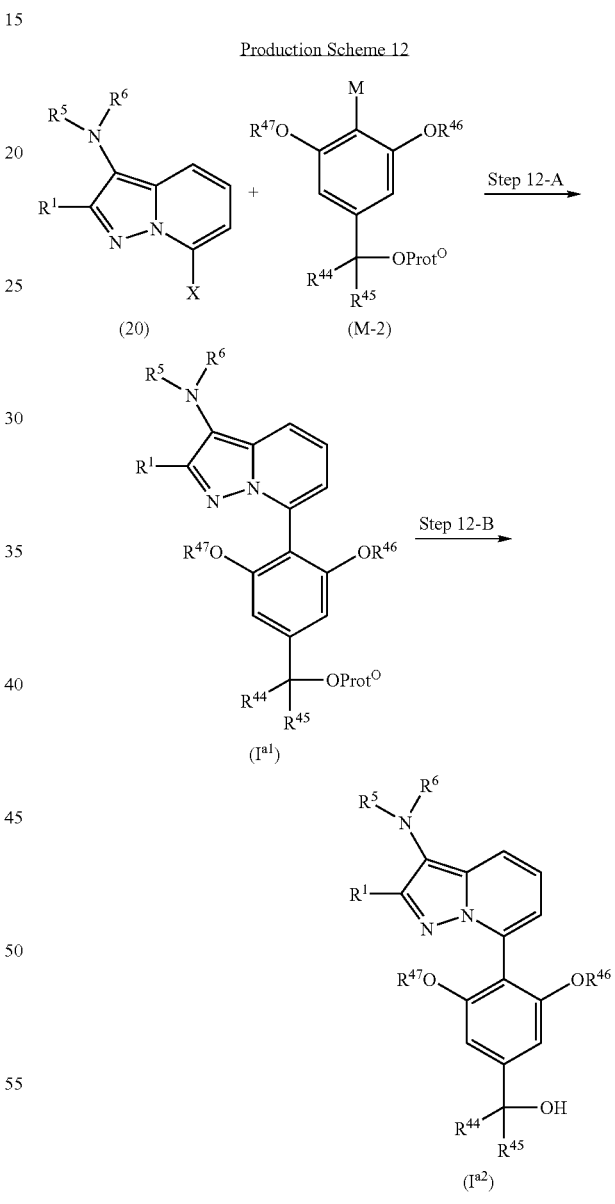

Step 12-A: A compound represented by formula (20) may be subjected to coupling reaction with a metal aryl reagent represented by formula (M-2) in the presence of a transition metal catalyst, in the same manner as Step 5-E in Production Scheme 5 above, to afford a derivative represented by formula ($I^{a1}$).

Step 12-B: A pyrazolo[1,5-a]pyridine derivative represented by formula ($I^{a1}$) having a protected hydroxyl group may be subjected to deprotection reaction suitable for the protecting group to obtain a pyrazolo[1,5-a]pyridine derivative represented by formula ($I^{a2}$) having an alcoholic group. The deprotection reaction is carried out at between −80° C. to 200° C., in the presence or in the absence of a deprotecting reagent, and in a solvent or without a solvent. For example, when the protection is with a silyl group, the solvent used will differ depending on the starting materials, reagents, etc. and is not particularly restricted so long as it dissolves the starting materials to some degree without inhibiting the reaction, and preferably there may be mentioned ethyl acetate, tetrahydrofuran, diethyl ether, dioxane, acetonitrile, methanol, ethanol, dichloromethane, chloroform, nitromethane, phenol, anisole and thiophenol, which may be used alone or as a mixed solvent. As examples of deprotecting reagents to be used there may be mentioned fluorine anion-generating compounds such as tetrabutylammonium fluoride, hydrogen fluoride and cesium fluoride, acids such as hydrochloric acid, sulfuric acid, trifluoroacetic acid and methanesulfonic acid, or bases such as potassium carbonate, sodium carbonate, sodium hydroxide and potassium hydroxide. In the case of a benzyl ether or the like, the benzyl group may be deprotected by hydrogenation reaction in a solvent such as ethanol, in the presence of a metal catalyst such as Pd—C.

Production Scheme 13

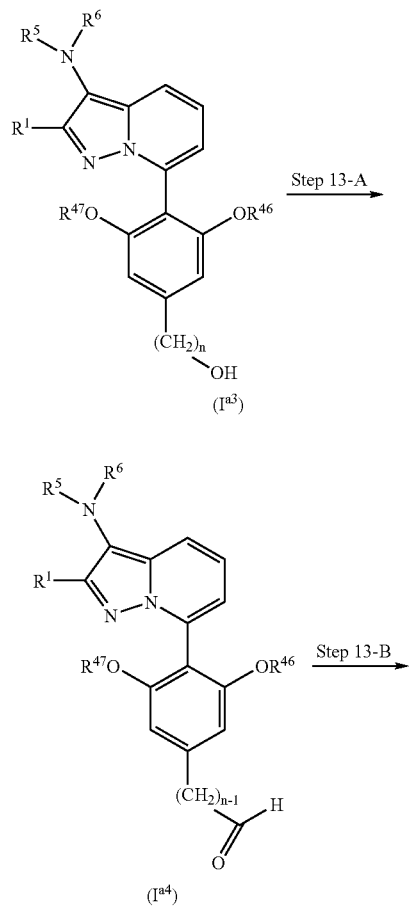

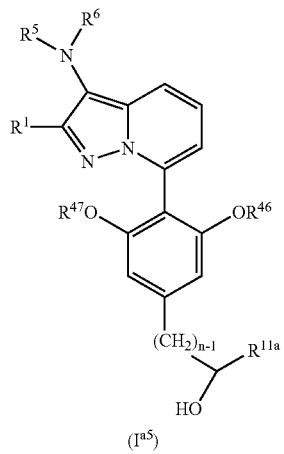

Step 13-A: A pyrazolo[1,5-a]pyridine derivative represented by formula ($I^{a3}$) having a primary alcoholic group may be subjected to oxidation reaction in a solvent or without a solvent in the presence of an oxidizing agent, to afford an aldehyde derivative represented by formula ($I^{a4}$) The reaction temperature will usually be −78° C. to 150° C. The solvent used will differ depending on the starting materials, reagents, etc. and is not particularly restricted so long as it dissolves the starting materials to some degree without inhibiting the reaction, and preferably there may be mentioned tetrahydrofuran, diethyl ether, 1,2-dichloroethane, dichloromethane, chloroform, acetonitrile, toluene and dimethylsulfoxide, which may be used alone or as a mixed solvent. As oxidizing agents to be used there may be mentioned oxalyl chloride utilized as an activating agent for dimethylsulfoxide oxidation (Swern oxidation), as well as metal reagents such as activated manganese dioxide, sulfur trioxide-pyridine complex, pyridinium chlorochromate (PCC), pyridinium dichromate (PDC), 2,3-dichloro-5,6-dicyano-1,4-benzoquinone (DDQ) and Dess-Martin reagent. The oxidizing agent is preferably used at 1 to 30 equivalents.

Step 13-B: A pyrazolo[1,5-a]pyridine derivative represented by formula ($I^{a4}$) having an aldehyde group may be reacted with an alkyl metal reagent such as a Grignard reagent, alkyllithium, alkylzinc or alkylcesium, either in an inert solvent or without a solvent, to afford a pyrazolo[1,5-a]pyridine derivative represented by formula ($I^{a5}$). The reaction temperature will usually be −80° C. to 80° C. The solvent used will differ depending on the starting materials, reagents, etc. and is not particularly restricted so long as it dissolves the starting materials to some degree without inhibiting the reaction, and preferably there may be mentioned hexane, pentane, tetrahydrofuran and diethyl ether, which may be used alone or as a mixed solvent. The alkyl metal reagent is preferably used at 1 to 2 equivalents.

Production Scheme 14

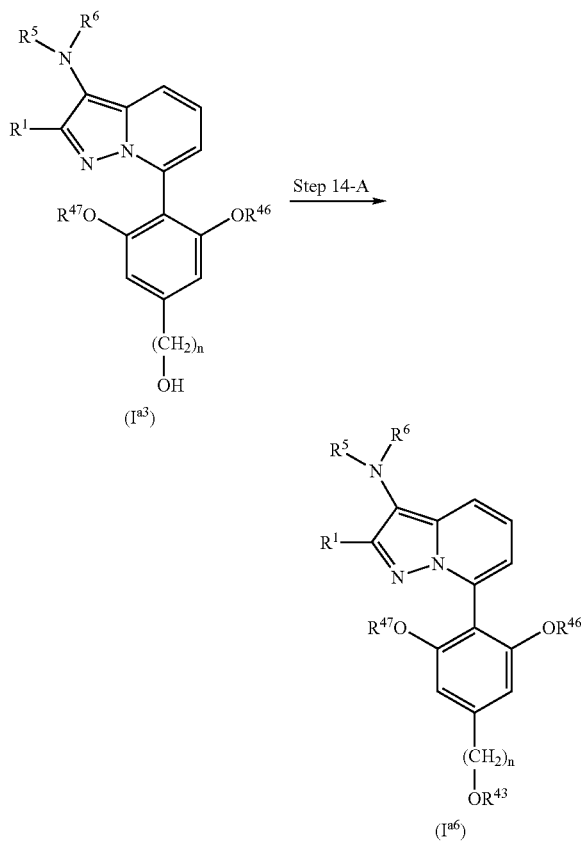

Step 14-A: A pyrazolo[1,5-a]pyridine derivative represented by formula ($I^{a3}$) having a hydroxyl group may be reacted with an alkylating agent (alkyl halide, dialkylsulfuric acid, alkylsulfonic acid ester, etc.) or the like, either in a solvent or without a solvent, in the presence or in the absence of a base and in the presence or in the absence of a phase transfer catalyst, to afford a hydroxyl-alkylated pyrazolo[1,5-a]pyridine derivative represented by formula ($I^{a6}$) The reaction temperature will usually be –10° C. to 200° C. The solvent used will differ depending on the reagents, etc. and is not particularly restricted so long as it dissolves the starting materials to some degree without inhibiting the reaction, and preferably there may be mentioned tetrahydrofuran, acetone, N,N-dimethylformamide, dimethylsulfoxide, ethanol, acetonitrile, toluene and water, which may be used alone or as a mixed solvent. The base used will differ depending on the solvent, etc. and is not particularly restricted so long as it does not inhibit the reaction, and preferably there may be mentioned potassium hydride, sodium hydride, potassium tert-butoxide, potassium carbonate, sodium carbonate, calcium carbonate, potassium hydroxide, sodium hydroxide, barium hydroxide, silver oxide, barium oxide, and the like. The phase transfer catalyst used will differ depending on the solvent, etc. and is not particularly restricted so long as it does not inhibit the reaction, and preferably there may be mentioned tetrabutylammonium iodide, tetrabutylammonium bromide, and tetrabutylammonium hydrogensulfate. The alkylating agent is preferably used at 1 to 2 equivalents, the base at 1 to 2 equivalents and the phase transfer catalyst at 1 to 2 equivalents.

Production Scheme 15

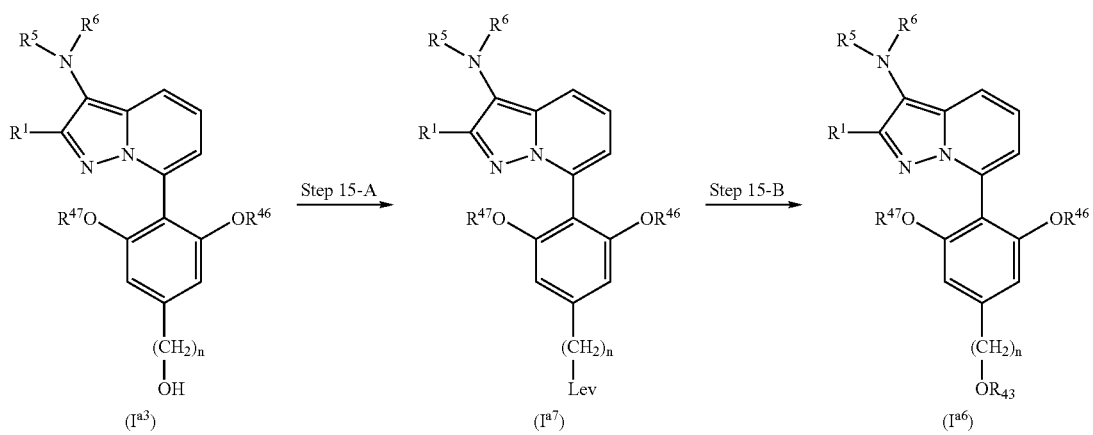

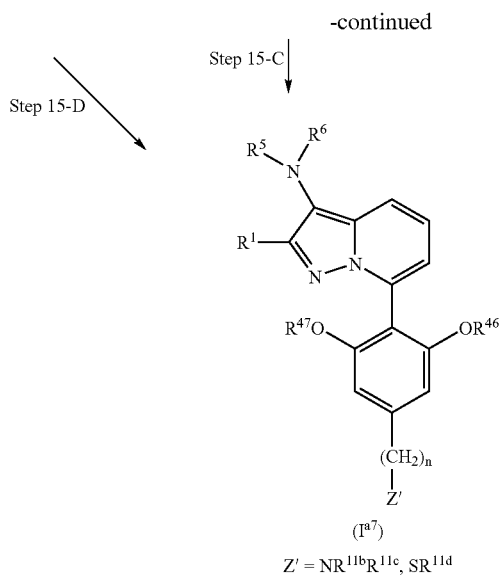

$Z' = NR^{11b}R^{11c}, SR^{11d}$

Step 15-A: The following is a production scheme for a pyrazolo[1,5-a]pyridine derivative represented by formula ($I^{a7}$), wherein the hydroxyl group of a pyrazolo[1,5-a]pyridine derivative represented by formula ($I^{a3}$) having a hydroxyl group is converted to a leaving group.

Sulfonic acid esterification reaction: A pyrazolo[1,5-a]pyridine derivative represented by formula ($I^{a3}$) having a hydroxyl group may be reacted with a sulfonic acid esterification reagent at 0° C. to 250° C., either in a solvent or without a solvent and in the presence or in the absence of a base, to afford a sulfonic acid ester derivative represented by formula ($I^{a7}$). The sulfonic acid esterification reagent used will differ depending on the solvent, etc. and is not particularly restricted so long as it does not inhibit the reaction, and preferably there may be mentioned methanesulfonyl chloride, tosyl chloride, tosyl fluoride, methanesulfonic anhydride, tosylic anhydride, trifluoromethanesulfonic anhydride, and the like. The base used will differ depending on the solvent, etc. and is not particularly restricted so long as it does not inhibit the reaction, and preferably there may be mentioned triethylamine, N-methylmorpholine, pyridine and the like. The solvent used will differ depending on the reagents, etc. and is not particularly restricted so long as it dissolves the starting materials to some degree without inhibiting the reaction, and preferably there may be mentioned dichloromethane, diethyl ether, tetrahydrofuran, tert-butyl ether, acetonitrile, N,N-dimethylformamide, dimethylsulfoxide and toluene, which may be used alone or as a mixed solvent. The sulfonic acid esterification reagent is preferably used at 1 to 2 equivalents and the base at 1 to 2 equivalents.

Halogenation (chlorination, bromination, iodination) reaction: A pyrazolo[1,5-a]pyridine derivative represented by formula ($I^{a3}$) having a hydroxyl group may be reacted with a halogenating agent such as N-chlorosuccinimide, phosphorous oxychloride, thionyl chloride, carbon tetrabromide, N-bromosuccinimide, bromine, phosphorus tribromide, phosphorus pentabromide, iodine or the like or with triphenylphosphine and carbon tetrachloride or carbon tetrabromide, at 0° C. to 250° C. either in a solvent or without a solvent, to afford a halogenated compound ($I^{a7}$). A base such as triethylamine, imidazole or 4-(dimethylamino)pyridine may also be added to the reaction mixture. The solvent used will differ depending on the reagents, etc. and is not particularly restricted so long as it dissolves the starting materials to some degree without inhibiting the reaction, and preferably there may be mentioned dichloromethane, toluene and N,N-dimethylformamide, which may be used alone or as a mixed solvent. Compound ($I^{a7}$) may also be obtained by direct reaction of a compound represented by formula ($I^{a3}$) with thionyl chloride, methanesulfonyl chloride or the like at 0° C. to 250° C. either in a solvent or without a solvent.

Fluorination reaction: A pyrazolo[1,5-a]pyridine derivative represented by formula ($I^{a3}$) having a hydroxyl group may be reacted with a fluorinating reagent at −78° C. to 0° C., either in a solvent or without a solvent, to afford a fluorinated pyrazolo[1,5-a]pyridine derivative represented by formula ($I^{a7}$). The solvent used will differ depending on the reagents and is not particularly restricted so long as it dissolves the starting materials to some degree without inhibiting the reaction, and preferably there may be mentioned dichloromethane, diglyme, isooctane and monofluorotrichloromethane, which may be used alone or as a mixed solvent. The fluorinating reagent used will differ depending on the solvent, etc. and is not particularly restricted so long as it does not inhibit the reaction, and preferably there may be mentioned diethylaminosulfur trifluoride (DAST), sulfur tetrafluoride, morpholinosulfur trifluoride (morph-DAST), and the like. The fluorinating reagent is preferably used at 1 to 5 equivalents.

Step 15-B: A pyrazolo[1,5-a]pyridine derivative represented by formula ($I^{a7}$) may be reacted with a nucleophilic reagent such as an alkali metal salt of an alkoxide at −78° C. to 250° C., either in a solvent or without a solvent, to afford a pyrazolo[1,5-a]pyridine derivative represented by formula ($I^{a6}$). The solvent used will differ depending on the starting materials, reagents, etc. and is not particularly restricted so long as it dissolves the starting materials to some degree without inhibiting the reaction, and preferably there may be mentioned tetrahydrofuran, diethyl ether, N,N-dimethylformamide, dimethylsulfoxide, toluene and ethanol, which may be used alone or as a mixed solvent. As nucleophilic reagents there may be mentioned alkali metal salts of alkoxides, and specifically there may be mentioned sodium methoxide, sodium ethoxide, and the like. The nucleophilic reagent is preferably used at 1 to 2 equivalents.

Step 15-C: A pyrazolo[1,5-a]pyridine derivative represented by formula ($I^{a7}$) having a leaving group may be reacted with a nucleophilic reagent at −78° C. to 250° C., either in a solvent or without a solvent, to afford a pyrazolo[1,5-a]pyridine derivative represented by formula ($I^{a8}$). The solvent used will differ depending on the starting materials, reagents, etc. and is not particularly restricted so long as it dissolves the starting materials to some degree without inhibiting the reaction, and preferably there may be mentioned tetrahydrofuran, diethyl ether, N,N-dimethylformamide, dimethylsulfoxide, toluene and ethanol, which may be used alone or as a mixed solvent. As nucleophilic reagents there may be mentioned amines such as ammonia, methylamine, dimethylamine, morpholine and piperidine, or alkali metal salts of thioalkoxides. The nucleophilic reagent is preferably used at 1 to 2 equivalents.

Alternatively, compound ($I^{a8}$) having an amino group may be obtained by reaction with sodium azide, sodium di-tert-butyliminodicarboxylate, sodium phthalimide or the like as a nucleophilic reagent, followed by reduction and deprotection reactions, etc.

In addition, compound ($I^{a8}$) having a thiol group may be obtained by reaction with potassium thioacetate, thiourea or the like as a nucleophilic reagent, followed by appropriate reactions.

Step 15-D: A pyrazolo[1,5-a]pyridine derivative represented by formula ($I^{a3}$) having a hydroxyl group may be converted to a pyrazolo[1,5-a]pyridine derivative represented by formula ($I^{a8}$) by Mitsunobu reaction using a diazo compound such as diethyl azodicarboxylate and an aminating reagent or the like in the presence of an organic phosphorus compound, in a solvent or without a solvent. The reaction temperature will usually be −70° C. to 80° C. As examples of aminating reagents there may be mentioned phthalimides and the like. As examples of phosphine compounds there may be mentioned triphenylphosphine, tributylphosphine and the like, and as examples of azodicarboxylate compounds there may be mentioned diethyl azodicarboxylate, diisopropyl azodicarboxylate, and the like. The solvent used will differ depending on the starting materials, reagents, etc. and is not particularly restricted so long as it dissolves the starting materials to some degree without inhibiting the reaction, and preferably there may be mentioned tetrahydrofuran, diethyl ether and toluene, which may be used alone or as a mixed solvent.

Production Scheme 16

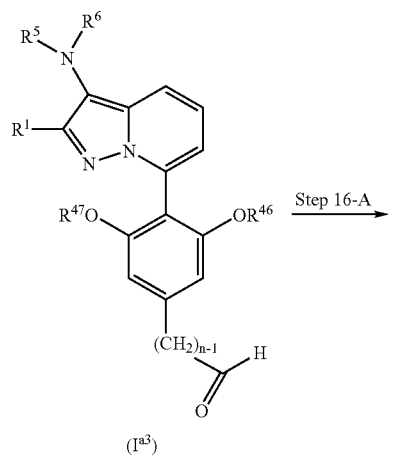

Step 16-A →

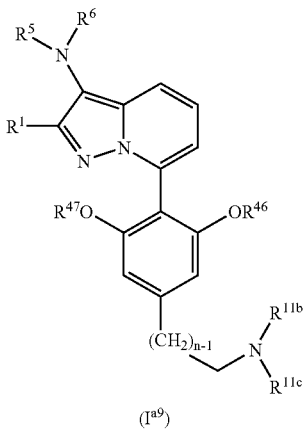

Step 16-A: A pyrazolo[1,5-a]pyridine derivative represented by formula ($I^{a4}$) having an aldehyde group may be reacted in the same manner as Steps 5-C and 5-D in Production Scheme 5 above to afford a pyrazolo[1,5-a]pyridine derivative ($I^{a9}$) having an optionally substituted amino group.

Representative production schemes for compound (I) according to the present invention have been described above, but the starting compounds and reagents used for production of the compounds of the invention may also form salts or hydrates which will differ depending on the starting materials and solvents used, and these are not particularly restricted so long as the reaction is not inhibited. The solvents used will also differ depending on the starting materials and reagents, and they are not particularly restricted so long as they do not inhibit the reaction and dissolve the starting materials to some degree. When compound (I) of the present invention is obtained as a free compound, a common method may be used to convert it to a salt which compound (I) can form. The different isomers (for example, geometric isomers, optical isomers based on asymmetric carbon, rotational isomers, stereoisomers and tautomers) obtained for compound (I) according to the invention may be purified and isolated using common separation means such as recrystallization, diastereomer salt methods, enzymatic separation methods and chromatography methods (for example, thin-layer chromatography, column chromatography, gas chromatography, etc.).

Compounds represented by formula (I) according to the present invention and salts thereof or hydrates of the foregoing may be used directly or in admixture with publicly known pharmaceutically acceptable carriers, and formulated by common methods. As preferred dosage forms there may be mentioned tablets, powders, fine particles, granules, coated tablets, capsules, syrups, lozenges, inhalants, suppositories, injections, ointments, eye salves, eye drops, nasal drops, ear drops, paps, lotions and the like. For the formulation there may be employed any commonly used excipients, binders, disintegrators, lubricants, coloring agents, corrective coatings, and if necessary, stabilizers, emulsifiers, absorbefacients, surfactants, pH adjustors, preservatives, antioxidants, or the like, in combination with various components that are ordinarily used as starting materials for pharmaceutical formulations.

As such components there may be mentioned animal and vegetable oils such as soybean oil, beef tallow and synthetic glycerides; hydrocarbons such as liquid paraffin, squalane and solid paraffin; ester oils such as octyldodecyl myristate and isopropyl myristate; higher alcohols such as cetostearyl alcohol and behenyl alcohol; silicone resins; silicone oils; surfactants such as polyoxyethylene fatty acid esters, sorbitan fatty acid esters, glycerin fatty acid esters, polyoxyethylene sorbitan fatty acid esters, polyoxyethylene hydrogenated castor oil and polyoxyethylene-polyoxypropylene block copolymer; water-soluble polymers such as hydroxyethylcellulose, polyacrylic acid, carboxyvinyl polymer, polyethylene glycol, polyvinylpyrrolidone and methylcellulose; lower alcohols such as ethanol and isopropanol; polyhydric alcohols such as glycerin, propylene glycol, dipropylene glycol and sorbitol; sugars such as glucose and sucrose; inorganic powders such as silicic anhydride, magnesium aluminum silicate and aluminum silicate; purified water, and the like. Examples of excipients which may be used include lactose, corn starch, white soft sugar, glucose, mannitol, sorbit, crystalline cellulose and silicon dioxide; examples of binders which may be used include polyvinyl alcohol, polyvinyl ether, methylcellulose, ethylcellulose, gum arabic, tragacanth, gelatin, shellac, hydroxypropylcellulose, hydroxypropylmethyl cellulose, polyvinylpyrrolidone, polypropylene glycol/polyoxyethylene block polymer and meglumine, calcium citrate, dextrin pectin and carboxymethylcellulose calcium; examples of disintegrators which may be used include starch, agar, gelatin powder, crystalline cellulose, calcium carbonate, sodium hydrogencarbonate, calcium citrate, dextrin, pectin and carboxymethylcellulose calcium; examples of lubricants which may be used include magnesium stearate, talc, polyethylene glycol, silica and hydrogenated vegetable oils; examples of coloring agents which may be used include any of those approved for addition to drugs; examples of corrective coatings which may be used include cocoa powder, menthol, aromatic powders, mentha oil, borneol and powdered cinnamon; and examples of antioxidants which may be used include those approved for addition to drugs, such as ascorbic acid and alpha-tocopherol.

An oral formulation may be prepared by combining a compound of the present invention or salt thereof with an excipient, if necessary adding a binder, disintegrator, lubricant, coloring agent, corrective coating or the like, and forming a powder, fine particles, granules, tablets, coated tablets, capsules, etc. by a common method.

The tablets or granules may, of course, also be coated with a sugar coating, gelatin coating or other type of suitable coating if necessary.

In the case of a liquid formulation such as syrup, injection, eye drops or the like, a common method may be used for formulation with a pH adjustor, solubilizer, isotonizing agent or the like, as well as a solubilizing aid, stabilizer, buffering agent, suspending agent, antioxidant, etc. if necessary. In the case of a liquid formulation, it may also be lyophilized, and an injection may be administered intravenously, subcutaneously or intramuscularly. As preferred examples of suspending agents there may be mentioned methyl cellulose, polysorbate 80, hydroxyethyl cellulose, gum arabic, tragacanth powder, sodium carboxymethylcellulose, polyoxyethylene sorbitan monolaurate and the like; as preferred examples of solubilizing aids there may be mentioned polyoxyethylene hydrogenated castor oil, polysorbate 80, nicotinamide, polyoxyethylene sorbitan monolaurate and the like; as preferred examples of stabilizing agents there may be mentioned sodium sulfite, sodium metasulfite, ether and the like; and as preferred examples of preservatives there may be mentioned methyl paraoxybenzoate, ethyl paraoxybenzoate, sorbic acid, phenol, cresol, chlorocresol, and the like.

There are no particular restrictions on the method of preparing an external agent, and any common method may be employed. The base materials used may be any raw materials commonly employed in drugs, quasi drugs, cosmetics and the like, and as examples there may be mentioned raw materials such as animal and vegetable oils, mineral oils, ester oils, waxes, higher alcohols, fatty acids, silicone oils, surfactants, phospholipids, alcohols, polyhydric alcohols, water-soluble polymers, clay minerals, purified water and the like, with addition of pH adjustors, antioxidants, chelating agents, antiseptics and fungicides, coloring agents, aromas and the like if necessary. Also, if necessary, there may also be included differentiation-inducing components, or other components such as circulation promoters, microbicides, antiphlogistic agents, cell activators, vitamins, amino acids, humectants, keratolytic agents and the like.

Drug formulations comprising compound (I) of the present invention and salt thereof or hydrate of the foregoing as effective ingredients are useful for disease treatment or prevention in mammals (for example, humans, mice, rats, guinea pigs, rabbits, dogs, horses, monkeys, etc.), and especially for disease treatment or prevention in humans. Although the dosage of a drug according to the present invention will differ depending on the patient's severity of symptoms, age, gender, body weight, the dosage form, type of salt, drug sensitivity and specific type of disease, etc., it will generally be from about 30 µg to 10 g, preferably from 100 µg to 500 mg, more preferably from 100 µg to 100 mg per day for adult humans in the case of oral administration or about 1-3000 µg/kg and preferably 3-1000 µg/kg in the case of injection, administered once or divided over several times a day.

EXAMPLES

The following production examples, examples and test examples serve only for the purpose of illustration and are not intended to be restrictive on the compounds of the invention in any way. It will be apparent to those skilled in the art that various modifications may be added beyond these examples and within the scope of the claims of the invention in the present specification in order to maximize the effect of the invention, and such modifications are also encompassed within the claims.

The phrase "purified by silica gel column chromatography and the title compound was obtained from . . . fraction" in the present specification means to obtain the title compound by concentrating the solution of the fractions containing the target compound obtained by silica gel column chromatography, and, if necessary, further by recrystallization.

Production Example 1

2-(1-Butynyl)pyridine

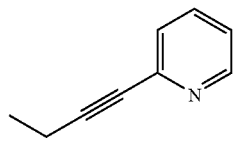

To a solution of 2-bromopyridine (50 g) dissolved in diethylamine (500 mL) was added dichlorobis(triphenylphosphine)palladium(II) (2.2 g) and copper iodide (0.3 g), and the reaction mixture was stirred for 4 hours at room temperature while introducing 1-butyne (100 g) as a gas. The resulting reaction mixture was bubbled with nitrogen, and then ethyl acetate was added. After the reaction mixture was filtered through celite to remove insoluble residue, the filtrate was washed with water and brine. The obtained organic extract was dried over anhydrous magnesium sulfate and filtered, the solvent was evaporated under reduced pressure, the residue was purified by silica gel column chromatography and the title compound (35 g) was obtained as a brown oil from the n-hexane:ethyl acetate (5:1) fraction.

$^1$H NMR (400 MHz, CDCl$_3$) δ 1.26 (t, J=7.6 Hz, 3H), 2.45 (q, J=7.6 Hz, 2H), 7.16-7.20 (m, 1H), 7.35-7.38 (m, 1H), 7.59-7.63 (m, 1H), 8.53-8.54 (m, 1H).

Production Example 2

2-Ethylpyrazolo[1,5-a]pyridine

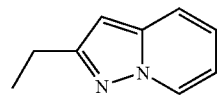

To a solution of 2-(1-butynyl)pyridine (12.8 g) dissolved in dichloromethane (60 mL) was added a solution of O-mesitylenesulfonylhydroxylamine (Reference; Synthesis, 1997, 1) (20 g) in dichloromethane (132 mL) while cooling with ice, and the reaction mixture was stirred for 30 minutes. Diethyl ether (2 L) was added to the reaction mixture to precipitate crystals, which were filtered off and then dried under reduced pressure to afford a crude product of N-amino-2-(1-butynyl)pyridinium mesitylenesulfonate (12.6 g) as colorless crystals.

A portion (6.1 g) of the obtained crude product of N-amino-2-(1-butynyl)pyridinium mesitylenesulfonate was dissolved in tetrahydrofuran (600 mL), and then potassium tert-butoxide (3.55 g) was added thereto at room temperature and the reaction mixture was vigorously stirred for 30 minutes. After adding ice water to the obtained reaction mixture, extraction was performed with ethyl acetate. After re-extraction of the aqueous layer with ethyl acetate and the insoluble residue was filtered with celite, the organic extracts were combined and washed with brine. The obtained organic extract was dried over anhydrous magnesium sulfate and filtered, the solvent was evaporated under reduced pressure, the residue was purified by silica gel column chromatography and the title compound (0.63 g) was obtained as a light yellow oil from the n-hexane:ethyl acetate (10:1) fraction.

$^1$H NMR (400 MHz, CDCl$_3$) δ 1.36 (t, J=7.6 Hz, 3H), 2.86 (q, J=7.6 Hz, 2H), 6,30 (s, 1H), 6.65 (ddd, J=1.6, 6.8, 6.8 Hz, 1H), 7.04 (ddd, J=1.2, 6.8, 8.8 Hz, 1H), 7.41 (ddd, J=1.2, 1.2, 8.8 Hz, 1H), 8.37 (ddd, J=1.2, 1.2, 6.8 Hz, 1H).

Production Example 3

7-Bromo-2-ethylpyrazolo[1,5-a]pyridine

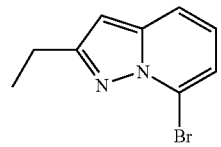

To a solution of 2-ethylpyrazolo[1,5-a]pyridine (80 mg) dissolved in tetrahydrofuran (1 mL) was added n-butyl-lithium (1.6M hexane solution: 0.58 mL) dropwise at −78° C. under a nitrogen stream, and the reaction mixture was further stirred for 30 minutes at the same temperature. A solution of 1,2-dibromo-1,1,2,2-tetrachloroethane (196 mg) in tetrahydrofuran (0.5 mL) was added dropwise to the reaction mixture, and stirring was continued for 30 minutes. After raising the temperature to room temperature and adding water to the reaction mixture, extraction was performed with ethyl acetate and the organic extract was washed with water and brine. The obtained organic extract was dried over anhydrous magnesium sulfate and filtered, the solvent was evaporated under reduced pressure, the residue was purified by silica gel column chromatography and the title compound (90 mg) was obtained as a light brown oil from the n-hexane:ethyl acetate (20:1) fraction.

$^1$H NMR (400 MHz, CDCl$_3$) δ 1.36 (t, J=7.6 Hz, 3H), 2.93 (q, J=7.6 Hz, 2H), 6,49 (s, 1H), 6.94 (dd, J=7.2, 8.4 Hz, 1H), 6.99 (dd, J=1.6, 7.2 Hz, 1H), 7.44 (dd, J=1.6, 8.4 Hz, 1H).

Production Example 4

7-Bromo-2-ethyl-3-nitropyrazolo[1,5-a]pyridine

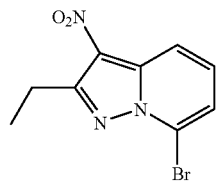

To a solution of 7-bromo-2-ethylpyrazolo[1,5-a]pyridine (1.1 g) dissolved in acetonitrile (20 mL) was added nitronium tetrafluoroborate (1.3 g) was added thereto while cooling with ice, and the reaction mixture was stirred for 30 minutes. The reaction mixture was then added to ice water, extraction was performed with ethyl acetate, and the organic extract was washed with water and brine. The obtained organic extract was dried over anhydrous magnesium sulfate and filtered, and the solvent was evaporated under reduced pressure. The obtained residue was purified by silica gel column chromatography and the title compound (670 mg) was obtained as yellow crystals from the n-hexane:ethyl acetate (10:1) fraction.

$^1$H NMR (400 MHz, CDCl$_3$) δ 1.42 (t, J=7.6 Hz, 3H), 3.27 (q, J=7.6 Hz, 2H), 7.39 (dd, J=1.2, 7.6 Hz, 1H), 7.50 (dd, J=7.6, 8.8 Hz, 1H), 8.38 (dd, J=1.2, 8.8 Hz, 1H).

Production Example 5

7-Bromo-2-ethylpyrazolo[1,5-a]pyridine-3-amine

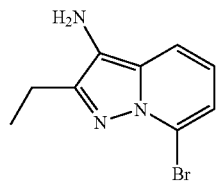

To a suspension of 7-bromo-2-ethyl-3-nitropyrazolo[1,5-a]pyridine (1.78 g) in a mixed solution of ethanol (100 mL), water (50 mL) and acetic acid (10 mL) was added zinc powder (1.78 g) at room temperature and the reaction mixture was stirred for 1 hour at 65° C. The reaction mixture was filtered through celite to remove insoluble residue and the filtrate was evaporated under reduced pressure. Water was added to the obtained residue and extraction was performed with ethyl acetate, and after washing the organic extract with water, saturated aqueous sodium bicarbonate and brine, the organic extract was dried over anhydrous magnesium sulfate and filtered, and the solvent was evaporated under reduced pressure. The obtained residue was purified by silica gel column chromatography (60 g) and the title compound (1.16 g) was obtained as a dark green oil from the ethyl acetate:n-hexane (4:1) fraction.

$^1$H NMR (400 MHz, CDCl$_3$) δ 1.36 (t, J=7.6 Hz, 3H), 2.89 (q, J=7.6 Hz, 2H), 6.81 (dd, J=7.1, 8.7 Hz, 1H), 6.88 (dd, J=1.3, 7.0 Hz, 1H), 7.34 (dd, J=1.3, 8.6 Hz, 1H).

Production Example 6 tert-Butyl N-(7-bromo-2-ethylpyrazolo[1,5-a]pyridin-3-yl)carbamate

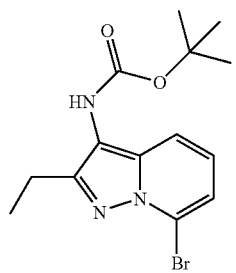

To a solution of 7-bromo-2-ethylpyrazolo[1,5-a]pyridine-3-amine (1.16 g) in dichloromethane (50 mL) was added triethylamine (1.01 mL) and di-tert-butyl dicarbonate (1.34 mL) at room temperature, and the reaction mixture was stirred for 15 hours. After completion of the reaction, the solvent was evaporated under reduced pressure. Ethyl acetate was added to the residue, and the obtained organic extract was washed with water and brine, and dried over anhydrous magnesium sulfate and filtered, then the solvent was evaporated under reduced pressure. The obtained residue was purified by silica gel column chromatography (60 g) and the title compound (1.09 g) was obtained as hazel crystals from the ethyl acetate:n-hexane (1:3) fraction.

$^1$H NMR (400 MHz, CDCl$_3$) δ 1.34 (t, J=7.6 Hz, 3H), 1.52 (br s, 9H), 2.87 (q, J=7.6 Hz, 2H), 5.91 (br s, 1H), 6.92-7.04 (m, 2H), 7.40 (d, J=9.0 Hz, 1H).

Production Example 7

N-(7-Bromo-2-ethylpyrazolo[1,5-a]pyridin-3-yl)-N-cyclopropylmethylamine

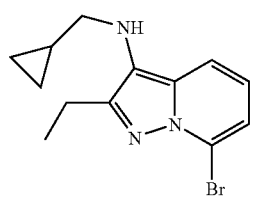

To a solution of tert-butyl N-(7-bromo-2-ethylpyrazolo[1,5-a]pyridin-3-yl)carbamate (658 mg) in N,N-dimethylformamide (15 mL) was added sodium hydride (60% in oil; 116 mg) at room temperature under a nitrogen stream, and the reaction mixture was stirred for 30 minutes. (Bromomethyl)cyclopropane (0.286 mL) was added thereto at the same temperature, and the reaction mixture was stirred for 1 hour at 60° C. After completion of the reaction, the reaction mixture was gradually added to ice, ethyl acetate was added and the organic extract was washed with water and brine, after which it was dried over anhydrous magnesium sulfate and the solvent was evaporated under reduced pressure to afford a crude product of tert-butyl N-(7-bromo-2-ethylpyrazolo[1,5-a]pyridin-3-yl) -N-cyclopropylmethylcarbamate.

To a solution of crude tert-butyl N-(7-bromo-2-ethylpyrazolo[1,5-a]pyridin-3-yl)-N-cyclopropylmethylcarbamate dissolved in ethyl acetate (10 mL) was added 4N hydrochloric acid/ethyl acetate (30 mL), and the reaction mixture was stirred for 2 hours at room temperature. After completion of the reaction, a 5N aqueous sodium hydroxide solution was added to the reaction mixture while cooling with ice for neutralization. The reaction mixture was extracted with ethyl acetate, and after washing the organic extract with water and brine, it was dried over anhydrous magnesium sulfate and the solvent was evaporated under reduced pressure. The residue was purified by silica gel column chromatography (20 g) and the title compound (479 mg) was obtained as a yellow oil from the ethyl acetate:n-hexane (1:3) fraction.

$^1$H NMR (400 MHz, CDCl$_3$) δ 0.14-0.22 (m, 2H), 0.47-0.56 (m, 2H), 0.96-1.10 (m, 1H), 1.37 (t, J=7.6 Hz, 3H), 2.88 (d, J=6.8 Hz, 2H), 2.90 (q, J=7.6 Hz, 2H), 6.83 (dd, J=7.0, 8.8 Hz, 1H), 6.90 (dd, J=1.3, 7.1 Hz, 1H), 7.43 (dd, J=1.3, 8.8 Hz, 1H).

Production Example 8

N-(7-Bromo-2-ethylpyrazolo[1,5-a]pyridin-3-yl)-N-cyclopropylmethyl-N-tetrahydro-2H-4-pyranylmethylamine

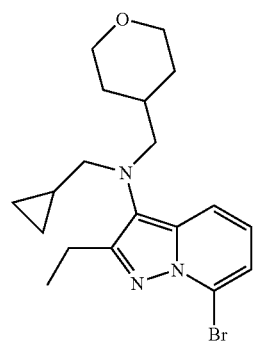

To a solution of N-(7-bromo-2-ethylpyrazolo[1,5-a]pyridin-3-yl)-N-cyclopropylmethylamine (106 mg) in tetrahydrofuran (3 mL) was added tetrahydropyran-4-carbaldehyde (123 mg) at room temperature, and then sodium triacetoxyborohydride (229 mg) was gradually added. After stirring the reaction mixture for 1 hour, saturated aqueous sodium bicarbonate was added thereto. The obtained mixture was extracted with ethyl acetate, and organic extract was washed with brine and then dried over anhydrous magnesium sulfate, and evaporated under reduced pressure. The residue was purified by silica gel column chromatography (10 g) and the title compound (120 mg) was obtained as a yellow oil from the ethyl acetate:n-hexane (1:6) fraction.

$^1$H NMR (400 MHz, CDCl$_3$) δ −0.02-0.06 (m, 2H), 0.33-0.43 (m, 2H), 0.75-0.88 (m, 1H), 1.20-1.34 (m, 2H), 1.38 (t, J=7.6 Hz, 3H), 1.48-1.62 (m, 1H), 1.69-1.78 (m, 2H), 2.88 (d, J=6.8 Hz, 2H), 2.91 (q, J=7.6 Hz, 2H), 3.04 (d, J=7.0 Hz, 2H), 3.30 (dt, J=2.1, 12.0 Hz, 2H), 3.90-4.00 (m, 2H), 6.88 (dd, J=7.1, 8.8 Hz, 1H), 6.96 (dd, J=1.3, 7.1 Hz, 1H), 7.49 (dd, J=1.3, 8.8 Hz, 1H).

Similarly to Production Example 7 and 8, the compound of Production Example 9 was obtained.

Production Example 9

N-(7-Bromo-2-ethylpyrazolo[1,5-a]pyridin-3-yl)-N-butyl-N-tetrahydro-2H-4-pyranylmethylamine Yellow oil

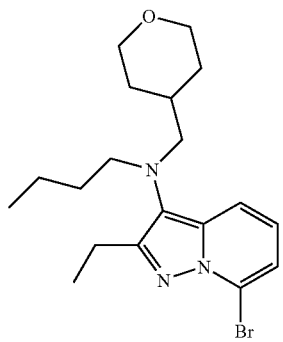

Production Example 10

7-[2,6-Dimethoxy-4-(methoxymethyl)phenyl]-2-ethyl-3-nitropyrazolo[1,5-a]pyridine

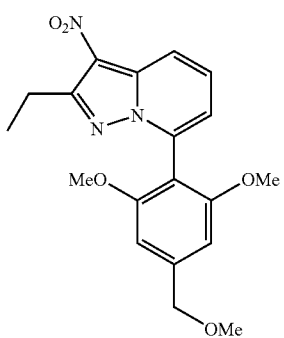

To a solution of 7-bromo-2-ethyl-3-nitropyrazolo[1,5-a]pyridine (1.0 g) dissolved in a mixture of 1,2-dimethoxyethane (50 mL) and water (25 mL) was added 2,6-dimethoxy-4-(methoxymethyl)phenylboric acid (1.26 g), tetrakis(triphenylphosphine)palladium(0) (0.64 g) and barium hydroxide octahydrate (1.75 g), and the reaction mixture was heated and stirred for 2 hours at 80° C. To the resultant reaction mixture was added water and ethyl acetate, and remove insoluble residue was filtered out with celite. The filtrate was extracted with ethyl acetate, the organic extract was washed with brine, dried over anhydrous magnesium sulfate and filtered, and the solvent was evaporated under reduced pressure. The obtained residue was purified by silica gel column chromatography and the title compound (0.77 g) was obtained as yellow crystals from the n-hexane:ethyl acetate (3:1) fraction.

$^1$H NMR (400 MHz, CDCl$_3$) δ 1.28 (t, J=7.2 Hz, 3H), 3.12 (q, J=7.2 Hz, 2H), 3.49 (s, 3H), 3.71 (s, 6H), 4.53 (s, 2H), 6.67 (s, 2H), 7.03 (dd, J=1.6, 7.2 Hz, 1H), 7.65 (dd, J=7.2, 8.8 Hz, 1H), 8.34 (dd, J=1.2, 8.8 Hz, 1H).

Production Example 11

7-Bromo-2-methylpyrazolo[1,5-a]pyridine

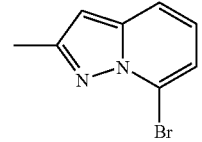

To a solution of 2-methylpyrazolo[1,5-a]pyridine (Reference; Chem. Pharm. Bull., 1983, 31, 4568-5572) (1.0 g) dissolved in tetrahydrofuran (20 mL) was added n-butyllithium (2.66 M hexane solution; 3.7 mL) dropwise at −78° C. under a nitrogen stream, and the reaction mixture was stirred for 30 minutes. To the reaction mixture was added a solution of 1,2-dibromo-1,1,2,2-tetrachloroethane (2.7 g) in tetrahydrofuran (5 mL) dropwise, and stirring was continued for 30 minutes. After adding saturated aqueous ammonium chloride to the obtained reaction mixture, the temperature was raised to room temperature, water was added to the reaction mixture and extraction was performed with ethyl acetate. The organic extract was separated, then washed with brine, dried over anhydrous magnesium sulfate and filtered. The solvent was evaporated under reduced pressure, the residue was purified by silica gel column chromatography and the title compound (1.34 g) was obtained as a yellow oil from the n-hexane:ethyl acetate (10:1) fraction.

$^1$H NMR (400 MHz, CDCl$_3$) δ 2.55 (s, 3H), 6.45 (s, 1H), 6.93 (dd, J=7.2, 8.4 Hz, 1H), 6.97 (dd, J=1.6, 7.2 Hz, 1H), 7.41 (dd, J=1.6, 8.4 Hz, 1H).

Production Example 12

7-Bromo-2-methyl-3-nitropyrazolo[1,5-a]pyridine

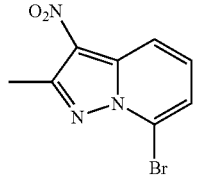

To a solution of 7-bromo-2-methylpyrazolo[1,5-a]pyridine (1.3 g) dissolved in acetonitrile (25 mL) was added nitronium tetrafluoroborate (900 mg) while stirring on ice, and the reaction mixture was stirred for 10 minutes. The obtained reaction mixture was added to ice water, and the precipitated crystals were collected by filtration, washed with water and then dried under reduced pressure to afford crude crystals. These were purified by silica gel column chromatography and the title compound (900 mg) was obtained as yellow crystals from the n-hexane:ethyl acetate (5:1) fraction.

$^1$H NMR (400 MHz, CDCl$_3$) δ 2.85 (s, 3H), 7.38 (dd, J=1.2, 7.6 Hz, 1H), 7.49 (dd, J=7.6, 8.8 Hz, 1H), 7.35 (dd, J=1.2, 8.8 Hz, 1H).

Production Example 13 tert-Butyl N-(7-bromo-2-methylpyrazolo[1,5-a]pyridin-3-yl)carbamate

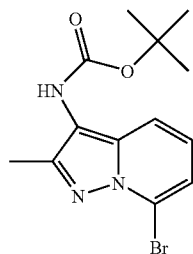

To a Suspension of 7-bromo-2-methyl-3-nitropyrazolo[1,5-a]pyridine (890 mg) in a mixed solution of ethanol (20 mL), water (10 mL) and acetic acid (2 mL) was added zinc powder (890 mg) at room temperature, and the reaction mixture was heated and stirred for 30 minutes at 60° C. After filtering off the insoluble residue, the filtrate was extracted with ethyl acetate and the organic extract was washed with saturated aqueous sodium bicarbonate and brine. The obtained organic extract was dried over anhydrous magnesium sulfate and filtered, the solvent was evaporated under reduced pressure, the residue was purified by silica gel column chromatography and [7-bromo-2-methylpyrazolo[1,5-a]pyridin-3-yl]amine (371 mg) was obtained as an brown oil from the n-hexane:ethyl acetate (1:1) fraction.

To a solution of the obtained [7-bromo-2-methylpyrazolo[1,5-a]pyridin-3-yl]amine and triethylamine (0.342 mL) dissolved in dichloromethane was added di-tert-butyl dicarbonate (429 mg) while cooling with ice, and the reaction mixture was stirred for 15 hours at room temperature. Water was added to the obtained reaction mixture, extraction was performed with ethyl acetate, and the organic extract was washed with water and brine. The obtained organic extract was dried over anhydrous magnesium sulfate and filtered, the solvent was evaporated under reduced pressure, the residue was purified by silica gel column chromatography and the title compound (420 mg) was obtained as an ecru oil from the n-hexane:ethyl acetate (5:1) fraction.

$^1$H NMR (400 MHz, CDCl$_3$) δ 1.52 (br s, 9H), 2.47 (s, 3H), 5.88-5.92 (m, 1H), 6.94-7.00 (m, 2H), 7.37-7.42 (m, 1H).

Similarly to Production Example 7 and 8, the compound of Production Example 14 was obtained.

Production Example 14

N-(7-Bromo-2-methylpyrazolo[1,5-a]pyridin-3-yl)-N-cyclopropylmethyl-N-tetrahydro-2H-4-pyranylmethylamine

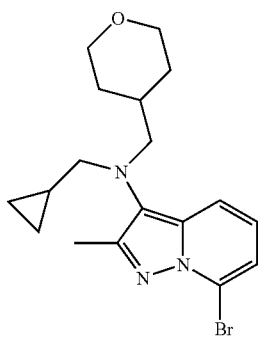

$^1$H NMR (400 MHz, CDCl$_3$) δ −0.04-0.08 (m, 2H), 0.32-0.43 (m, 2H), 0.74-0.88 (m, 1H), 1.20-1.36 (m, 2H), 1.46-1.62 (m, 1H), 1.66-1.78 (m, 2H), 2.52 (s, 3H), 2.87 (d, J=6.8 Hz, 2H), 3.03 (d, J=6.8 Hz, 2H), 3.30 (dt, J=2.0, 12.0 Hz, 2H), 3.89-3.99 (m, 2H), 6.88 (dd, J=1.4, 6.8 Hz, 1H), 6.95 (dd, J=6.8, 8.8 Hz, 1H), 7.47 (dd, J=1.4, 8.8 Hz, 1H).

Production Example 15

2-(3-Methoxy-1-propynyl)pyridine

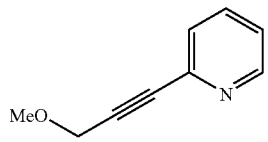

To a solution of 2-bromopyridine (20 g) dissolved in diethylamine (100 mL) was added 3-methoxy-1-propyne (11.8 g), dichlorobis(triphenylphosphine)palladium(II) (888 mg) and copper iodide (121 mg), and the reaction mixture was stirred for 1 hour at 40° C. under a nitrogen stream. After the reaction mixture was filtered through celite to remove insoluble residue, the filtrate was evaporated under reduced pressure, the residue was purified by silica gel column chromatography and the title compound (16.8 g) was obtained as a light orange oil from the n-hexane:ethyl acetate (5:1) fraction.

$^1$H NMR (400 MHz, CDCl$_3$) δ 3.48 (s, 3H), 4.36 (s, 2H), 7.22-7.26 (m, 1H), 7.44-7.47 (m, 1H), 7.66 (ddd, J=1.6, 7.6, 7.6 Hz, 1H), 8.57-8.60 (m, 1H).

Production Example 16

2-(Methoxymethyl)pyrazolo[1,5-a]pyridine

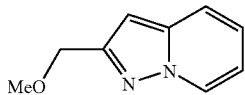

To a solution of 2-(3-methoxy-1-propynyl)pyridine (13.2 g) dissolved in dichloromethane (50 mL) was added a solution of O-mesitylenesulfonylhydroxylamine (Reference; Synthesis, 1997, 1) (21 g) in dichloromethane (80 mL) dropwise while cooling with ice, and the reaction mixture was stirred for 30 minutes. Diethyl ether (1 L) was added to the obtained reaction mixture to precipitate crystals, which were collected by filtration and dried under reduced pressure to afford a crude product of 1-amino-2-(3-methoxy-1-propynyl)pyridinium 2,4,6-trimethyl-1-benzenesulfonate as ecru crystals (27.1 g).

To a solution of the obtained crude product of 1-amino-2-(3-methoxy-1-propynyl)pyridinium 2,4,6-trimethyl-1-benzenesulfonate (27.1 g) dissolved in methanol (100 mL) was added sodium methoxide (28% methanol solution; 14.3 mL) dropwise while cooling with ice, and the reaction mixture was stirred for 20 minutes at room temperature. After adding ice water to the obtained reaction mixture, the methanol was evaporated under reduced pressure, water was added to the residue and extraction was performed 3 times with ethyl acetate. The organic extracts were combined, washed with brine, dried over anhydrous magnesium sulfate and filtered, and the solvent was evaporated under reduced pressure. The residue was purified by silica gel column chromatography and the title compound (3.54 g) was obtained as a light orange oil from the n-hexane:ethyl acetate (5:1) fraction.

¹H NMR (400 MHz, CDCl₃) δ 3.47 (s, 3H), 4.68 (s, 2H), 6.50 (s, 1H), 6.70-6.75 (m, 1H), 7.06-7.11 (m, 1H), 7.47-7.50 (m, 1H), 8.40-8.43 (m, 1H).

Production Example 17

(7-Bromopyrazolo[1,5-a]pyridin-2-yl)methyl methyl ether

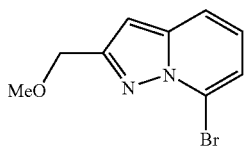

To a solution of 2-(methoxymethyl)pyrazolo[1,5-a]pyridine (3.5 g) dissolved in tetrahydrofuran (350 mL) was added n-butyllithium (2.66M hexane solution; 10.5 mL) dropwise at −78° C. under a nitrogen stream, and the reaction mixture was stirred for 30 minutes. 1,2-Dibromoethane (2.05 mL) was added dropwise to the obtained reaction mixture and stirring was continued for 30 minutes. After adding saturated aqueous ammonium chloride to the reaction mixture, the temperature was raised to room temperature, water was added and extraction was performed with ethyl acetate. The organic extract was washed with brine, dried over anhydrous magnesium sulfate and filtered. The solvent was evaporated under reduced pressure, the residue was purified by silica gel column chromatography and the title compound (2.75 g) was obtained as a light yellow oil from the n-hexane:ethyl acetate (10:1) fraction.

¹H NMR (400 MHz, CDCl₃) δ 3.47 (s, 3H), 4.75 (s, 2H), 6.71 (s, 1H), 6.99 (dd, J=7.2, 8.8 Hz, 1H), 7.05 (dd, J=1.2, 7.2 Hz, 1H), 7.51 (dd, J=1.2, 8.8 Hz, 1H).

Production Example 18

(7-Bromo-3-nitropyrazolo[1,5-a]pyridin-2-yl)methyl methyl ether

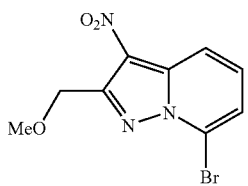

To a solution of (7-bromopyrazolo[1,5-a]pyridin-2-yl)methyl methyl ether (1.0 g) dissolved in acetonitrile (20 mL) was added nitronium tetrafluoroborate (606 mg) while stirring on ice. The obtained reaction mixture was added to ice water, extracted with ethyl acetate and then washed with water and brine. The obtained organic extract was dried over anhydrous magnesium sulfate and filtered, the solvent was evaporated under reduced pressure, the residue was purified by silica gel column chromatography and the title compound (546 mg) was obtained as light yellow crystals from the n-hexane:ethyl acetate (5:1) fraction.

¹H NMR (400 MHz, CDCl₃) δ 3.61 (s, 3H), 5.09 (s, 2H), 7.44 (dd, J=1.2, 7.6 Hz, 1H), 7.54 (dd, J=7.6, 8.8 Hz, 1H), 7.51 (dd, J=1.2, 8.8 Hz, 1H).

Production Example 19 tert-Butyl N-[7-bromo-2-(methoxymethyl)pyrazolo[1,5-a]pyridin-3-yl]carbamate

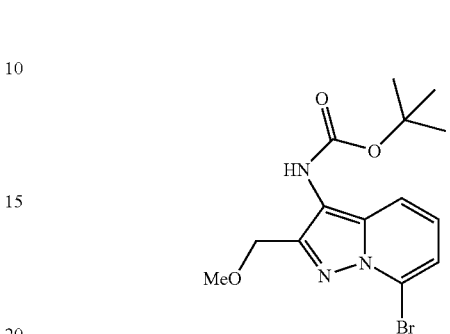

To a suspension of (7-bromo-3-nitropyrazolo[1,5-a]pyridin-2-yl)methyl methyl ether (540 mg) in a mixed solution of ethanol (10 mL), water (5 mL) and acetic acid (1 mL) was added zinc powder (540 mg), and the reaction mixture was heated and stirred for 30 minutes at 60° C. After filtering off insoluble residue, water was added to the filtrate, extraction was performed with ethyl acetate and the organic extract was washed with saturated aqueous sodium bicarbonate and brine. The obtained organic extract was dried over anhydrous magnesium sulfate and filtered, the solvent was evaporated under reduced pressure, the residue was purified by silica gel column chromatography and 7-bromo-2-(methoxymethyl)pyrazolo[1,5-a]pyridine-3-amine (371 mg) was obtained as a brown oil from the n-hexane:ethyl acetate (2:1) fraction.

To a solution of the obtained 7-bromo-2-(methoxymethyl)pyrazolo[1,5-a]pyridine-3-amine dissolved in triethylamine (0.303 mL) and dichloromethane (5 mL) was added di-tert-butyl dicarbonate (380 mg) while cooling with ice, and the reaction mixture was further stirred overnight at room temperature. Water was added to the reaction mixture, extraction was performed with ethyl acetate, and the organic extract was washed with water and brine. The obtained organic extract was dried over anhydrous magnesium sulfate and filtered, the solvent was evaporated under reduced pressure, the residue was purified by silica gel column chromatography and the title compound (360 mg) was obtained as light yellow crystals from the n-hexane:ethyl acetate (5:1) fraction.

¹H NMR (400 MHz, CDCl₃) δ 1.52 (br s, 9H), 3.42 (s, 3H), 4.77 (s, 2H), 6.50-6.62 (m, 1H), 6.97 (dd, J=7.2, 8.8 Hz, 1H), 7.04 (dd, J=1.2, 8.8 Hz, 1H), 7.58-7.68 (m, 1H).

Similarly to Production Example 7 and 8, the compound of Production Example 20 was obtained.

Production Example 20

N-[7-Bromo-2-(methoxymethyl)pyrazolo[1,5-a]pyridin-3-yl]-N-cyclopropylmethyl-N-tetrahydro-2H-4-pyranylmethylamine

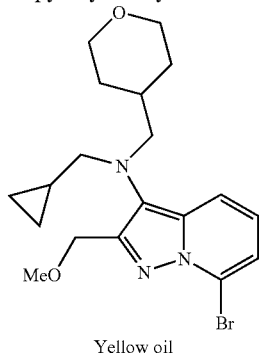

Yellow oil $^1$H NMR (400 MHz, CDCl$_3$) δ −0.04-0.04 (m, 2H), 0.30-0.40 (m, 2H), 0.72-0.86 (m, 1H), 1.18-1.33 (m, 2H), 1.46-1.62 (m, 1H), 1.64-1.75 (m, 2H), 2.87 (d, J=6.8 Hz, 2H), 3.03 (d, J=6.8 Hz, 2H), 3.27 (dt, J=2.0, 11.2 Hz, 2H), 3.44 (s, 3H), 3.86-3.96 (m, 2H), 4.67 (s, 2H), 6.89 (dd, J=1.4, 6.8 Hz, 1H), 7.02 (dd, J=6.8, 8.8 Hz, 1H), 7.54 (dd, J=1.4, 8.8 Hz, 1H).

Production Example 21

7-Bromo-2-methoxypyrazolo[1,5-a]pyridine

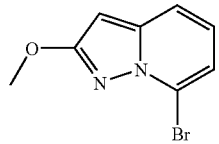

A solution of 2-methoxypyrazolo[1,5-a]pyridine (Reference; Bull. Chem. Soc. Japan, vol. 49(7), 1980-1984(1976)) (7.15 g) in tetrahydrofuran (140 mL) was cooled to −78° C. under a nitrogen stream, and after adding n-butyllithium (1.6M hexane solution: 46 mL) dropwise thereto, the reaction mixture was stirred for 30 minutes. A solution of 1,2-dibromo-1,1,2,2-tetrachloroethane (18.9 g) in tetrahydrofuran (30 mL) was added dropwise to the reaction mixture at −78° C., and stirring was continued for 1 hour. The reaction mixture was raised to room temperature, water was added, and then extraction was performed with ethyl acetate. The organic extract was washed with brine, dried over anhydrous magnesium sulfate and filtered, the solvent was evaporated under reduced pressure, the residue was purified by silica gel column chromatography and the title compound (7.1 g) was obtained as a yellow oil from the n-hexane:ethyl acetate (50:1) fraction.

$^1$H NMR (400 MHz, CDCl$_3$) δ 4.03 (s, 3H), 6.02 (s, 1H), 6.91-6.97 (m, 2H), 7.31 (dd, J=2.4, 7.6 Hz, 1H).

Production Example 22

7-Bromo-2-methoxypyrazolo[1,5-a]pyridine-3-amine

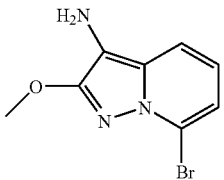

To a solution of 7-bromo-2-methoxypyrazolo[1,5-a]pyridine (1 g) dissolved in acetic acid (10 mL) was added an aqueous solution (5 mL) of sodium nitrite (334 mg), and the reaction mixture was stirred for 20 minutes at room temperature. After adding ethanol (60 mL) and water (30 mL) to the reaction mixture, zinc powder (1 g) was added and the reaction mixture was heated and stirred for 30 minutes at 60° C. The reaction mixture was filtered through celite to remove insoluble residue, water was added and extraction was performed with ethyl acetate. The organic extract was washed with brine, dried over anhydrous magnesium sulfate and filtered, the solvent was evaporated under reduced pressure, the residue was purified by silica gel column chromatography and the title compound (750 mg) was obtained as brown crystals from the n-hexane:ethyl acetate (3:1) fraction.

$^1$H NMR (400 MHz, CDCl$_3$) δ 4.13 (s, 3H), 6.78 (dd, J=1.6, 6.8 Hz, 1H), 6.81 (dd, J=6.8, 8.4 Hz, 1H), 7.24 (dd, J=1.6, 8.4 Hz, 1H).

Production Example 23 tert-Butyl N-(7-bromo-2-methoxypyrazolo[1,5-a]pyridin-3-yl)carbamate

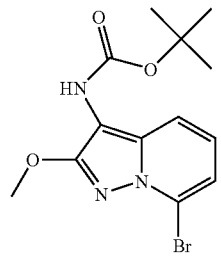

To a solution of 7-bromo-2-methoxypyrazolo[1,5-a]pyridine-3-amine (810 mg) dissolved in dichloromethane (20 mL) was added triethylamine (0.7 mL) and di-tert-butyl dicarbonate (923 µL) while cooling with ice, and the reaction mixture was stirred overnight at room temperature. Water was added to the obtained reaction mixture, extraction was performed with ethyl acetate, and the organic extract was washed with brine. The obtained organic extract was dried over anhydrous magnesium sulfate and filtered, the solvent was evaporated under reduced pressure, the residue was purified by silica gel column chromatography and the title compound (1.05 g) was obtained as yellow crystals from the n-hexane:ethyl acetate (10:1) fraction.

$^1$H NMR (400 MHz, CDCl$_3$) δ 1.49 (s, 9H), 4.12 (s, 3H), 6.89 (dd, J=1.2, 7.6 Hz, 1H), 6.94 (dd, J=7.6, 8.8 Hz, 1H), 7.30-7.39 (m, 1H).

Production Example 24

N-(7-Bromo-2-methoxypyrazolo[1,5-a]pyridin-3-yl)-N-cyclopropylmethyl-N-tetrahydro-2H-4-pyranylmethylamine

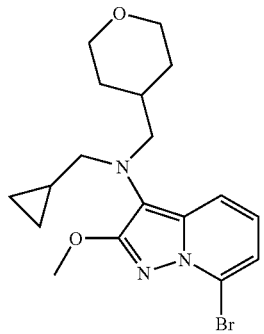

Sodium hydride (60% in oil; 24.6 mg) was added to a solution of tert-butyl N-(7-bromo-2-methoxypyrazolo[1,5-a]pyridin-3-yl)carbamate (140 mg) in N,N-dimethylformamide (10 mL) at room temperature and the reaction mixture was stirred for 30 minutes. (Bromomethyl)cyclopropane (0.06 mL) was added thereto at the same temperature, and the reaction mixture was stirred for 1 hour at 60° C. After completion of the reaction, the reaction mixture was gradually added to ice, extraction was performed with ethyl acetate, the organic extract was washed with water and brine, dried over anhydrous magnesium sulfate and filtered, and the solvent was evaporated under reduced pressure to afford a crude product of tert-butyl N-(7-bromo-2-methoxypyrazolo[1,5-a]pyridin-3-yl)-N-cyclopropylmethylcarbamate.

The obtained crude product of tert-butyl N-(7-bromo-2-methoxypyrazolo[1,5-a]pyridin-3-yl)-N-cyclopropylmethylcarbamate was dissolved in ethyl acetate (10 mL) without purification, and then 4N hydrochloric acid/ethyl acetate (15 mL) was added and the reaction mixture was stirred for 2 hours at room temperature. After completion of the reaction, a 5N aqueous sodium hydroxide solution was added to the reaction mixture while cooling with ice for neutralization. Ethyl acetate was added, and the obtained organic extract was washed with water and brine, dried over anhydrous magnesium sulfate and filtered, and the solvent was evaporated under reduced pressure to afford a crude product of N-(7-bromo-2-methoxypyrazolo[1,5-a]pyridin-3-yl)-N-cyclopropylmethylamine.

The obtained crude product of N-(7-bromo-2-methoxypyrazolo[1,5-a]pyridin-3-yl)-N-cyclopropylmethylamine was dissolved in tetrahydrofuran (10 mL) without further purification, and then tetrahydropyran-4-carbaldehyde (233 mg) was added thereto at room temperature and sodium triacetoxyborohydride (433 mg) was gradually added. After stirring the reaction mixture for 2 hours, to the reaction mixture was added saturated aqueous sodium bicarbonate. After which extraction was performed with ethyl acetate, the organic extract was washed with brine and dried over anhydrous magnesium sulfate, and the solvent was evaporated under reduced pressure. The residue was purified by silica gel column chromatography (10 g) and the title compound (110 mg) was obtained as a yellow oil from the ethyl acetate:n-hexane (1:6) fraction.

$^1$H NMR (400 MHz, CDCl$_3$) δ −0.02-0.10 (m, 2H), 0.20-0.40 (m, 2H), 0.70-0.90 (m, 1H), 1.10-1.39 (m, 2H), 1.40-1.60 (m, 1H), 1.62-1.80 (m, 2H), 2.81 (d, J=6.4 Hz, 2H), 2.95 (d, J=7.2 Hz, 2H), 3.27 (dt, J=2.0, 12.0 Hz, 2H), 3.80-4.00 (m, 2H), 4.11 (s, 3H), 6.80-6.95 (m, 2H), 7.33 (dd, J=1.6, 8.4 Hz, 1H).

Production Example 25 tert-Butyl N-[2-methylthiopyrazolo[1,5-a]pyridin-3-yl]carbamate

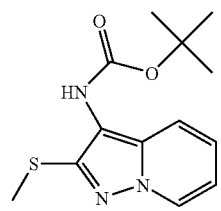

To a suspension of 2-methylthio-3-nitropyrazolo[1,5-a]pyridine (Reference; Heterocycles, 1977, 6, 379) (400 mg) in ethanol (20 mL), water (10 mL), acetic acid (2 mL) was added zinc powder (800 mg) and the reaction mixture was heated and stirred for 30 minutes at 80° C. The insoluble residue was filtered out, water was added to the filtrate and extraction was performed with ethyl acetate, and then the organic extract was washed with saturated aqueous sodium bicarbonate and brine. The organic extract was dried over anhydrous magnesium sulfate and filtered, and the solvent was evaporated under reduced pressure to afford (2-methylthiopyrazolo[1,5-a]pyridin-3-yl)amine as a crude product.

To a solution of the obtained crude (2-methylthiopyrazolo[1,5-a]pyridin-3-yl)amine dissolved in dichloromethane (5 mL) was added triethylamine (0.4 mL) and then di-tert-butyl dicarbonate (625 mg) while cooling with ice and the reaction mixture was stirred overnight at room temperature. Water was added to the reaction mixture, extraction was performed twice with ethyl acetate, and the organic extract was washed with water and brine. The obtained organic extract was dried over anhydrous magnesium sulfate and filtered, the solvent was evaporated under reduced pressure, the residue was purified by silica gel column chromatography and the title compound (230 mg) was obtained as a yellow oil from the n-hexane:ethyl acetate (5:1) fraction.

$^1$H NMR (400 MHz, CDCl$_3$) δ 1.53 (br s, 9H), 2.60 (s, 3H), 6.00-6.15 (m, 1H), 6.69 (t, J=6.8 Hz, 1H), 7.11 (t, J=8.0 Hz, 1H), 7.40-7.50 (m, 1H), 8.83 (d, J=6.8 Hz, 1H).

Production Example 26 tert-Butyl N-[7-iodo-2-methylthiopyrazolo[1,5-a]pyridin-3-yl]carbamate

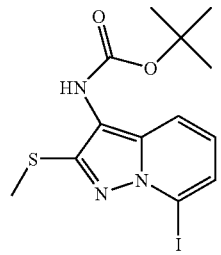

To a solution of tert-butyl N-[2-methylthiopyrazolo[1,5-a]pyridin-3-yl]carbamate (21.6 g) dissolved in tetrahydrofuran (1 L) was n-butyllithium (1.6M hexane solution; 130 mL) dropwise at −78° C. under a nitrogen stream, and the reaction mixture was stirred for 30 minutes. A solution of 1,2-diiodoethane (24 g) in tetrahydrofuran (50 mL) was added to the obtained reaction mixture, and stirring was continued for 1 hour. After adding saturated aqueous ammonium chloride to the reaction mixture, the temperature was raised to room temperature, extraction was performed with ethyl acetate and the organic extract was washed with water and brine. The obtained organic extract was dried over anhydrous magnesium sulfate and filtered, the solvent was evaporated under reduced pressure, the residue was purified by silica gel column chromatography and the title compound (21.5 g) was obtained as yellow crystals from the n-hexane:ethyl acetate (5:1) fraction.

$^1$H NMR (400 MHz, CDCl$_3$) δ 1.52 (s, 9H), 2.64 (s, 3H), 6.02-6.10 (m, 1H), 6.81 (dd, J=7.2, 8.8 Hz, 1H), 7.22 (dd, J=1.2, 7.2 Hz, 1H), 7.42-7.50 (m, 1H).

Production Example 27

N-Cyclopropylmethyl-N-[7-iodo-2-(methylsulfanyl) pyrazolo[1,5-a]pyridin-3-yl]amine

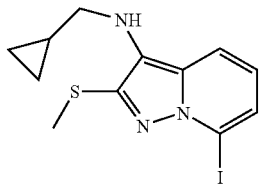

To a solution of tert-butyl N-[7-iodo-2-methylthiopyrazolo[1,5-a]pyridin-3-yl]carbamate (600 mg) in N,N-dimethylformamide (6 mL) was added sodium hydride (60% in oil; 80 mg) with ice bath, and the reaction mixture was stirred for 30 minutes at room temperature. (Bromomethyl)cyclopropane (0.22 mL) was added to the reaction mixture at the same temperature, and stirring was continued for 1 hour at 40° C. After completion of the reaction, the reaction mixture was gradually added to ice, extraction was performed with ethyl acetate, and the organic extract was washed with water and brine. The organic extract was dried over anhydrous magnesium sulfate and the solvent was evaporated under reduced pressure to afford a crude product of tert-butyl N-cyclopropylmethyl-N-[7-iodo-2-(methylsulfanyl)pyrazolo[1,5-a]pyridin-3-yl]carbamate.

To a solution of the crude tert-butyl N-cyclopropylmethyl-N-[7-iodo-2-(methylsulfanyl)pyrazolo[1,5-a]pyridin-3-yl]carbamate dissolved in ethyl acetate (1 mL) was added 4N hydrochloric acid/ethyl acetate (10 mL), and the reaction mixture was stirred for 2 hours at room temperature. After completion of the reaction, saturated aqueous sodium bicarbonate was added to the reaction mixture while cooling with ice for neutralization. The reaction mixture was extracted with ethyl acetate, and after washing the organic extract with water and brine, it was dried over anhydrous magnesium sulfate and the solvent was evaporated under reduced pressure. The residue was purified by silica gel column chromatography (20 g) and the title compound (506 mg) was obtained as a yellow oil from the ethyl acetate:n-hexane (1:3) fraction.

$^1$H NMR (400 MHz, CDCl$_3$) δ 0.16-0.24 (m, 2H), 0.48-0.56 (m, 2H), 1.00-1.10 (m, 1H), 2.60 (s, 3H), 2.96 (d, J=6.0 Hz, 2H), 3.00-3.24 (m, 1H), 6.68 (ddd, J=1.2, 6.8, 8.8 Hz, 1H), 7.17 (dd, J=1.2, 6.8 Hz, 1H), 7.43 (dd, J=1.2, 8.8 Hz, 1H).

Production Example 28

N-Cyclopropylmethyl-N-[7-iodo-2-(methylsulfanyl) pyrazolo[1,5-a]pyridin-3-yl]-N-tetrahydro-2H-4-pyranylmethylamine

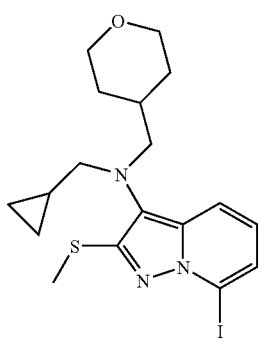

To a solution of N-cyclopropylmethyl-N-[7-iodo-2-(methylsulfanyl)pyrazolo[1,5-a]pyridin-3-yl]amine (70 mg) in tetrahydrofuran (2.5 mL) was added tetrahydropyran-4-carbaldehyde (56 mg) at room temperature, and then sodium triacetoxyborohydride (103 mg) was gradually added. After 1 hour, saturated aqueous sodium bicarbonate was added, extraction was performed with ethyl acetate, the extract was washed with brine and dried over anhydrous magnesium sulfate, and the solvent was evaporated under reduced pressure to afford a crude product of the title compound (50 mg) as a yellow oil.

$^1$H NMR (400 MHz, CDCl$_3$) δ −0.06-0.04 (m, 2H), 0.30-0.38 (m, 2H), 0.74-0.86 (m, 1H), 1.20-1.32 (m, 2H), 1.40-1.60 (m, 1H), 1.66-1.80 (m, 2H), 2.69 (s, 3H), 2.85 (d, J=6.8 Hz, 2H), 3.02 (d, J=7.2 Hz, 2H), 3.22-3.32 (m, 2H), 3.86-3.94 (m, 2H), 6.72 (dd, J=7.2, 8.8 Hz, 1H), 7.15 (dd, J=1.2, 7.2 Hz, 1H), 7.40 (dd, J=1.2, 8.8 Hz, 1H).

Production Example 29

2,6-Dimethoxy-4-(methoxymethyl)phenylboric acid

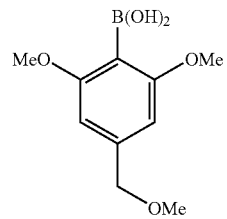

To a solution of 3,5-dimethoxy(methoxymethyl)benzene (23.7 g) in tetrahydrofuran (500 mL) was added n-butyllithium (1.56M hexane solution; 100 mL) at −78° C., and the reaction mixture was stirred for 30 minutes while cooling with ice. After cooling the internal temperature of the obtained reaction mixture to −78° C., to a reaction mixture was added triisopropoxyborane (39 mL), and the internal temperature was raised to room temperature while stirring. After completion of the reaction, saturated aqueous ammonium chloride was added to the reaction mixture while cooling with ice, and then ethyl acetate was added to the reaction mixture, the organic extract was washed with brine and dried over anhydrous magnesium sulfate, and the solvent was evaporated under reduced pressure. The residue was purified by silica gel column chromatography and the title compound (7.5 g) was obtained as a yellow oil from the ethyl acetate fraction.

$^1$H NMR (400 MHz, CDCl$_3$) δ 3.43 (s, 3H), 3.92 (s, 6H), 4.47 (s, 2H), 6.61 (s, 2H), 7.18 (s, 2H).

Production Example 30

4-(Hydroxymethyl)-2,6-dimethoxyphenylboric acid

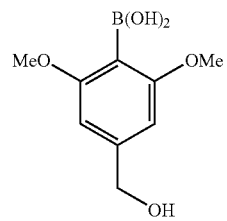

To a solution of 3,5-dimethoxybenzyl alcohol (2.71 g) in tetrahydrofuran (50 mL) was added n-butyllithium (1.56M hexane solution; 36.2 mL)while cooling with ice with ice bath, and the internal temperature was raised to room temperature and stirred for 1 hour. The internal temperature was then cooled to −78° C., to the mixture was added triethoxyborane (9.6 mL), and the temperature was raised to room temperature while stirring. After completion of the reaction, saturated aqueous ammonium chloride was added to the reaction mixture while cooling with ice and the reaction mixture was extracted with ethyl acetate, and then after washing the organic extract with brine, it was dried over anhydrous magnesium sulfate and the solvent was evaporated under reduced pressure. The residue was purified by silica gel column chromatography (50 g) and the title compound (1.72 g) was obtained as a white amorphous solid from the ethyl acetate fraction.

$^1$H NMR (400 MHz, CDCl$_3$) δ 3.92 (s, 6H), 4.73 (s, 2H), 6.65 (s, 2H), 7.18 (s, 2H).

Similarly to Production Example 30, the compounds of Production Example 31 and 32 were synthesized.

Production Example 31

4-(2-Hydroxyethyl)-2,6-dimethoxyphenylboric acid

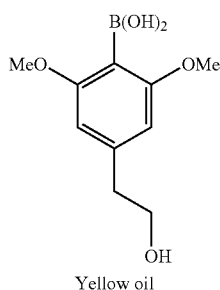

Yellow oil $^1$H NMR (400 MHz, CDCl$_3$) δ 1.56-1.62 (m, 1H), 2.88 (t, J=6.4 Hz, 2H), 3.88-3.92 (m, 2H), 3.90 (s, 6H), 6.51 (s, 2H), 7.14 (s, 2H).

Production Example 32

4-(3-Hydroxypropyl)-2,6-dimethoxyphenylboric acid

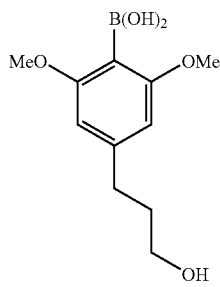

$^1$H NMR (400 MHz, CDCl$_3$) δ 1.84-1.94 (m, 2H), 2.68-2.76 (m, 2H), 3.64-3.74 (m, 2H), 3.90 (s, 6H), 6.48 (s, 2H), 7.16 (s, 2H).

Similarly to Production Example 29, the compounds of Production Example 33 to 35 were synthesized.

Production Example 33

4-(Ethoxymethyl)-2,6-dimethoxyphenylboric acid

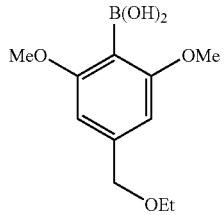

$^1$H NMR (400 MHz, CDCl$_3$) δ 1.28 (t, J=7.1 Hz, 3H), 3.58 (q, J=7.1 Hz, 2H), 3.92 (s, 6H), 4.51 (s, 2H), 6.63 (s, 2H), 7.19 (s, 2H).

Production Example 34

4-[1-[1-(tert-Butyl)-1,1-dimethylsilyl]oxyethyl]-2,6-dimethoxyphenylboric acid

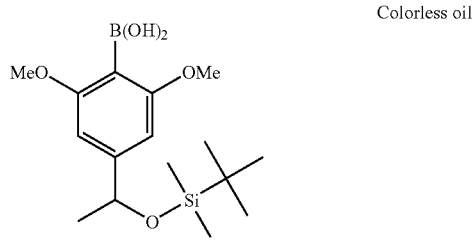

Colorless oil $^1$H NMR (400 MHz, CDCl$_3$) δ 0.01 (s, 3H), 0.08 (s, 3H), 0.92 (s, 9H), 1.41 (d, J=6.4 Hz, 3H), 3.90 (s, 6H), 4.84 (q, J=6.4 Hz, 1H), 6.61 (s, 2H), 7.17 (s, 2H).

Production Example 35

2,4-Dimethoxy-6-(methoxymethyl)phenylboric acid

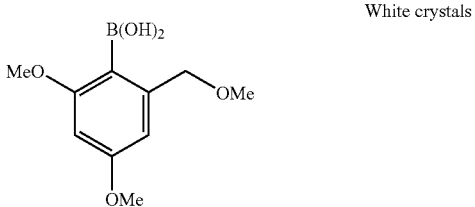

White crystals $^1$H NMR (400 MHz, CDCl$_3$) δ 3.41 (s, 3H), 3.85 (s, 3H), 3.88 (s, 3H), 4.53 (s, 2H), 6.48 (d, J=2.4 Hz, 1H), 6.55 (d, J=2.4 Hz, 1H), 7.09 (br s, 2H).

Example 1

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine

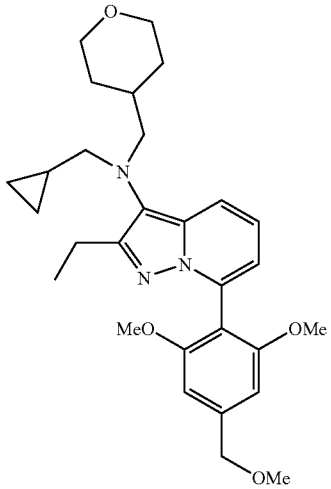

To a solution of N-(7-bromo-2-ethylpyrazolo[1,5-a]pyridin-3-yl)-N-cyclopropylmethyl-N-tetrahydro-2H-4-pyranylmethylamine(60 mg) dissolved in 1,2-dimethoxyethane (2 mL) and water (1 mL) was added 2,6-dimethoxy-4-(methoxymethyl)phenylboric acid (45 mg), tetrakis(triphenylphosphine)palladium(0) (35 mg) and barium hydroxide octahydrate (72 mg), and the reaction mixture was heated and stirred for 4 hours at 90° C. The reaction mixture was then cooled to room temperature, water and ethyl acetate were added, the reaction mixture was filtered through celite to remove insoluble residue, and the filtrate was extracted with ethyl acetate. The combined organic extract was washed with brine, dried over anhydrous magnesium sulfate and filtered, and the solvent was evaporated under reduced pressure. The residue was purified by silica gel column chromatography and the title compound (40 mg) was obtained as light yellow crystals from the n-hexane:ethyl acetate (1:1) fraction.

$^1$H NMR (400 MHz, CDCl$_3$) δ −0.02-0.04 (m, 2H), 0.34-0.38 (m, 2H), 0.80-0.90 (m, 1H), 1.22 (t, J=7.6 Hz, 3H), 1.24-1.34 (m, 2H), 1.54-1.64 (m, 1H), 1.74-1.80 (m, 2H), 2.77 (q, J=7.6 Hz, 2H), 2.88 (d, J=6.8 Hz, 2H), 3.05 (d, J=7.2 Hz, 2H), 3.31 (t, J=11.6 Hz, 2H), 3.49 (s, 3H), 3.73 (s, 6H), 3.90-4.00 (m, 2H), 4.53 (s, 2H), 6.59 (dd, J=1.2, 6.8 Hz, 1H), 6.67 (s, 2H), 7.00 (dd, J=6.8, 8.8 Hz, 1H), 7.44 (dd, J=1.2, 8.8 Hz, 1H).

Example 1-2

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine

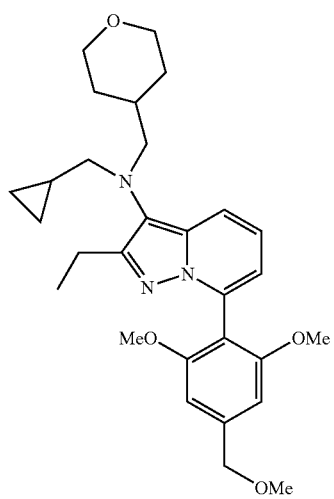

The title compound (29 g) was recrystallized from ethanol (80 mL) to afford light yellow crystals (27.5 g).

$^1$H NMR (600 MHz, DMSO-d$_6$) δ −0.02-0.00 (m, 2H), 0.32-0.35 (m, 2H), 0.73-0.79 (m, 1H), 1.11-1.19 (m, 5H), 1.51-1.57 (m, 1H), 1.69-1.72 (br dd, J=2.0, 12.7 Hz, 2H), 2.65 (q, J=7.6 Hz, 2H), 2.84 (d, J=6.8 Hz, 2H), 3.01 (d, J=7.1 Hz, 2H), 3.21 (ddd, J=1.7, 11.7, 11.7 Hz, 2H), 3.39 (s, 3H), 3.63 (s, 6H), 3.82 (br dd, J=2.4, 11.5 Hz, 2H), 4.49 (s, 2H), 6.55 (dd, J=1.2, 6.8 Hz, 1H), 6.74 (s, 2H), 7.06 (dd, J=6.6, 8.8 Hz, 1H), 7.51 (dd, J=1.2, 8.8 Hz, 1H).

Similarly to Example 1, the compounds of Example 2 to 9 were synthesized.

Example 2

N-Cyclopropylmethyl-N-7-[2,6-dimethoxy-4-(1-methoxyethyl)phenyl]-2-ethylpyrazolo[1,5-a]pyridin-3-yl-N-tetrahydro-2H-4-pyranylmethylamine Light yellow crystals

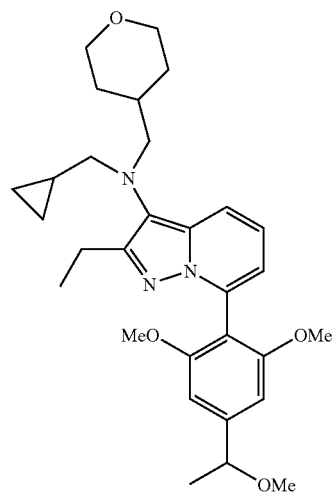

$^1$H NMR (400 MHz, CDCl$_3$) δ −0.02-0.04 (m, 2H), 0.32-0.38 (m, 2H), 0.80-0.92 (m, 1H), 1.23 (t, J=7.6 Hz, 3H), 1.22-1.34 (m, 2H), 1.52 (d, J=6.4 Hz, 3H), 1.52-1.64 (m, 1H), 1.72-1.82 (m, 2H), 2.79 (q, J=7.6 Hz, 2H), 2.89 (d, J=6.4 Hz, 2H), 3.05 (d, J=7.2 Hz, 2H), 3.26-3.34 (m, 2H), 3.36 (s, 3H), 3.73 (s, 6H), 3.90-3.98 (m, 2H), 4.34 (q, J=6.8 Hz, 1H), 6.61 (dd, J=1.2, 6.8 Hz, 1H), 6.64 (d, J=2.8 Hz, 2H), 7.01 (dd, J=6.8, 8.8 Hz, 1H), 7.44 (dd, J=1.2, 8.8 Hz, 1H).

Example 3

N-Cyclopropylmethyl-N-7-[4-(ethoxymethyl)-2,6-dimethoxyphenyl]-2-ethylpyrazolo[1,5-a]pyridin-3-yl-N-tetrahydro-2H-4-pyranylmethylamine Yellow crystals

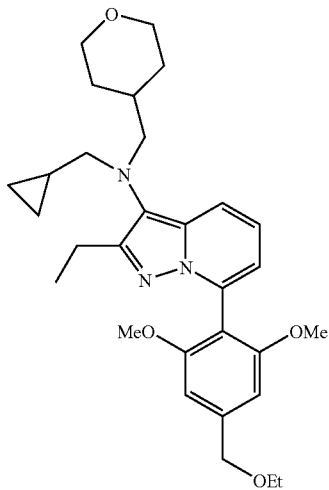

$^1$H NMR (400 MHz, CDCl$_3$) δ −0.02-0.06 (m, 2H), 0.34-0.43 (m, 2H), 0.80-0.94 (m, 1H), 1.24 (t, J=7.5 Hz, 3H), 1.33 (t, J=7.0 Hz, 3H), 1.20-1.38 (m, 2H), 1.54-1.68

(m, 1H), 1.74-1.84 (m, 2H), 2.78 (q, J=7.5 Hz, 2H), 2.90 (d, J=6.6 Hz, 2H), 3.07 (d, J=7.0 Hz, 2H), 3.33 (dt, J=1.6, 12.0 Hz, 2H), 3.66 (q, J=7.0 Hz, 2H), 3.75 (s, 6H), 3.92-4.02 (m, 2H), 4.59 (s, 2H), 6.61 (br d, J=6.8 Hz, 1H), 6.71 (s, 2H), 7.03 (dd, J=7.0, 8.8 Hz, 1H), 7.46 (br d, J=8.8 Hz, 1H).

Example 4

N-Cyclopropylmethyl-N-7-[2,6-dimethoxy-4-(methoxymethyl)phenyl]-2-ethylpyrazolo[1,5-a]pyridin-3-yl-N-tetrahydro-3-furanylmethylamine Yellow oil

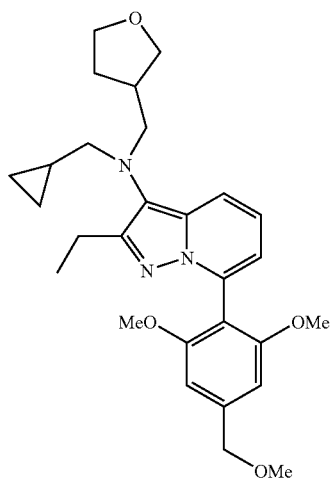

$^1$H NMR (400 MHz, CDCl$_3$) δ −0.02-0.04 (m, 2H), 0.32-0.42 (m, 2H), 0.80-0.82 (m, 1H), 1.21 (t, J=7.6 Hz, 3H), 1.58-1.66 (m, 1H), 1.84-1.94 (m, 1H), 2.20-2.32 (m, 1H), 2.74 (q, J=7.6 Hz, 2H), 2.90 (d, J=6.4 Hz, 2H), 3.40-3.50 (m, 1H), 3.18-3.26 (m, 1H), 3.47 (s, 3H), 3.58-3.70 (m, 2H), 3.71 (s, 6H), 3.72-3.82 (m, 2H), 4.51 (s, 2H), 6.58 (dd, J=0.8, 6.8 Hz, 1H), 6.66 (s, 2H), 7.00 (ddd, J=0.2, 6.8, 8.8 Hz, 1H), 7.42 (dd, J=0.6, 8.8 Hz, 1H)

Example 5

(4-3-[(cyclopropylmethyl)(tetrahydro-2H-4-pyranylmethyl)amino]-2-ethylpyrazolo[1,5-a]pyridin-7-yl-3,5-dimethoxyphenyl)methanol

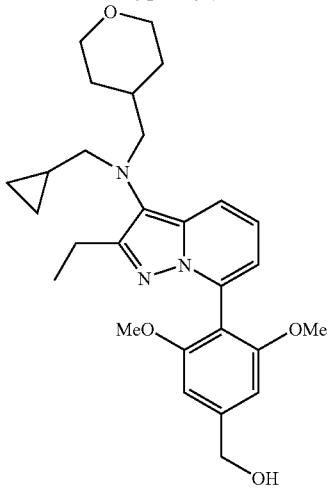

Light yellow amorphous solid $^1$H NMR (400 MHz, CDCl$_3$) δ −0.03-0.05 (m, 2H), 0.32-0.40 (m, 2H), 0.80-0.90 (m, 1H), 1.22 (t, J=7.5 Hz, 3H), 1.22-1.35 (m, 2H), 1.53-1.66 (m, 1H), 1.72-1.81 (m, 2H), 1.96 (t, J=5.6 Hz, 1H), 2.78 (q, J=7.5 Hz, 2H), 2.86-2.92 (m, 2H), 3.02-3.09 (m, 2H), 3.28-3.38 (m, 2H), 3.74 (s, 6H), 3.90-4.00 (m, 2H), 4.76 (d, J=5.6 Hz, 2H), 6.61 (dd, J=1.3, 6.8 Hz, 1H), 6.72 (s, 2H), 7.02 (dd, J=6.8, 8.8 Hz, 1H), 7.46 (dd, J=1.3, 8.8 Hz, 1H).

Example 6

(4-3-[(Cyclobutylmethyl)(tetrahydro-2H-4-pyranylmethyl)amino]-2-ethylpyrazolo[1,5-a]pyridin-7-yl-3,5-dimethoxyphenyl)methanol

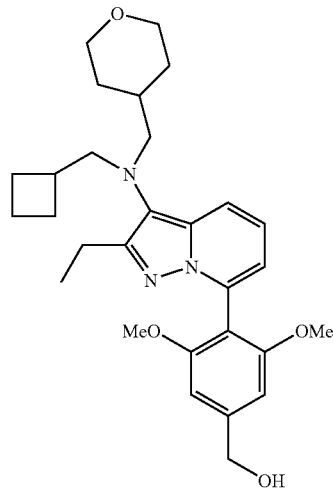

Light yellow amorphous solid $^1$H NMR (400 MHz, CDCl$_3$) δ 1.19-1.32 (m, 2H), 1.21 (t, J=7.5 Hz, 3H), 1.51-1.64 (m, 3H), 1.70-1.95 (m, 6H), 2.01 (t, J=5.6 Hz, 1H), 2.26-2.39 (m, 1H), 2.73 (q, J=7.5 Hz, 2H), 2.90-2.97 (m, 2H), 3.02-3.08 (m, 2H), 3.26-3.37 (m, 2H), 3.73 (s, 6H), 3.89-3.99 (m, 2H), 4.74 (d, J=5.6 Hz, 2H), 6.60 (dd, J=1.3, 6.8 Hz, 1H), 6.71 (s, 2H), 7.02 (dd, J=6.8, 8.8 Hz, 1H), 7.41 (dd, J=1.3, 8.8 Hz, 1H).

Example 7

2-(4-3-[(Cyclopropylmethyl)(tetrahydro-2H-4-pyranylmethyl)amino]-2-ethylpyrazolo[1,5-a]pyridin-7-yl-3,5-dimethoxyphenyl)-1-ethanol

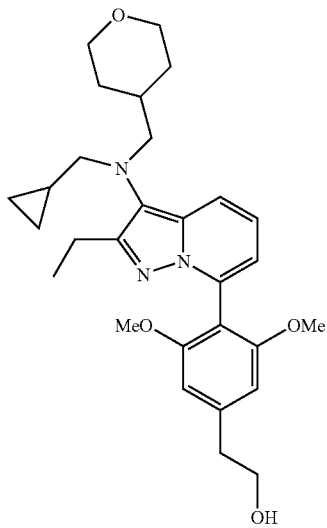

Light green oil $^1$H NMR (400 MHz, CDCl$_3$) δ −0.04-0.02 (m, 2H), 0.32-0.38 (m, 2H), 0.78-0.88 (m, 1H), 1.21 (t, J=7.6 Hz, 3H), 1.22-1.32 (m, 2H), 1.52-1.65 (m, 2H), 1.72-1.80 (m, 2H), 2.75 (q, J=7.6 Hz, 2H), 2.87 (d, J=6.8 Hz, 2H), 2.92 (t, J=6.4 Hz, 2H), 3.04 (d, J=7.2 Hz, 2H), 3.26-3.34 (m, 2H), 3.70 (s, 6H), 3.90-3.98 (m, 4H), 6.55 (s, 2H), 6.58 (dd, J=1.6, 6.8 Hz, 1H), 7.00 (dd, J=6.8, 8.8 Hz, 1H), 7.43 (dd, J=1.6, 8.8 Hz, 1H).

Example 8

3-(4-3-[(Cyclopropylmethyl)(tetrahydro-2H-4-pyranylmethyl)amino]-2-ethylpyrazolo[1,5-a]pyridin-7-yl-3,5-dimethoxyphenyl)-1-propanol

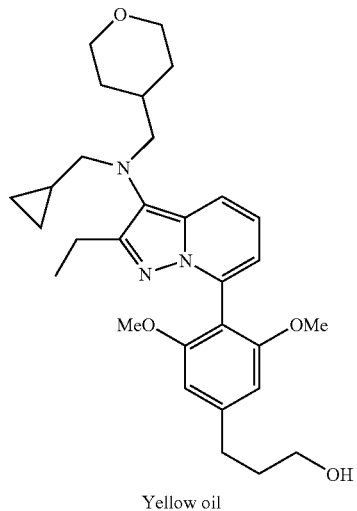

Yellow oil $^1$H NMR (400 MHz, CDCl$_3$) δ −0.03-0.01 (m, 2H), 0.33-0.37 (m, 2H), 0.81-0.85 (m, 1H), 1.19-1.31 (m, 5H), 1.50-1.57 (m, 1H), 1.72-1.77 (m, 2H), 1.95-2.04 (m, 2H), 2.73-2.80 (m, 4H), 2.87 (d, J=6.8 Hz, 2H), 3.04 (d, J=6.8 Hz, 2H), 3.30 (dt, J=2.0, 12.0 Hz, 2H), 3.70 (s, 6H), 3.76 (t, J=6.4 Hz, 2H), 3.91-3.95 (m, 2H), 6.54 (s, 2H), 6.59 (dd, J=1.2, 6.8 Hz, 1H), 7.00 (dd, J=6.8, 8.8 Hz, 1H), 7.43 (dd, J=1.6, 8.8 Hz, 1H).

Example 9

N-Cyclopropylmethyl-N-7-[2,4-dimethoxy-6-(methoxymethyl)phenyl]-2-ethylpyrazolo[1,5-a]pyridin-3-yl-N-tetrahydro-2H-4-pyranylmethylamine

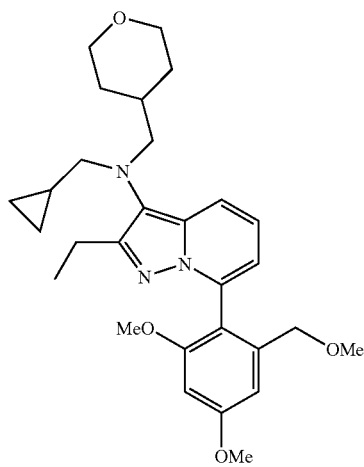

Light yellow crystals $^1$H NMR (400 MHz, CDCl$_3$) δ −0.04-0.02 (m, 2H), 0.30-0.36 (m, 2H), 0.78-0.88 (m, 1H), 1.20 (t, J=7.6 Hz, 3H), 1.20-1.32 (m, 2H), 1.52-1.64 (m, 1H), 1.72-1.80 (m, 2H), 2.70-2.80 (m, 2H), 2.87 (d, J=6.8 Hz, 2H), 3.04 (d, J=6.8 Hz, 2H), 3.19 (s, 3H), 3.28-3.34 (m, 2H), 3.68 (s, 3H), 3.88 (s, 3H), 3.90-3.98 (m, 2H), 3.98 (d, J=12.8 Hz, 1H), 4.21 (d, J=12.8 Hz, 1H), 6.51 (d, J=2.4 Hz, 1H), 6.54 (dd, J=1.6, 6.8 Hz, 1H), 6.76 (d, J=2.4 Hz, 1H), 6.99 (dd, J=6.8, 8.8 Hz, 1H), 7.44 (dd, J=1.2, 8.8 Hz, 1H).

Example 10 tert-Butyl N-7-[2,6-dimethoxy-4-(methoxymethyl)phenyl]-2-ethylpyrazolo[1,5-a]pyridin-3-ylcarbamate

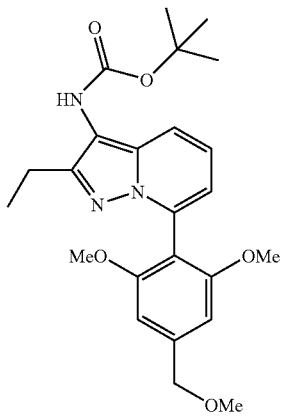

To a solution of tert-butyl N-(7-bromo-2-ethylpyrazolo[1,5-a]pyridin-3-yl)carbamate (100 mg) dissolved in 1,2-dimethoxyethane (6 mL) and water (3 mL) was added 2,6-dimethoxy-4-(methoxymethyl)phenylboric acid (100 mg), tetrakis(triphenylphosphine)palladium(0) (51 mg) and barium hydroxide octahydrate (139 mg), and the reaction mixture was heated and stirred for 3 hours at 80° C. under a nitrogen stream. Water was added to the obtained reaction mixture and extraction was performed with ethyl acetate. The organic extract was washed with brine, dried over anhydrous magnesium sulfate and filtered, and then the solvent was evaporated under reduced pressure, the residue was purified by silica gel column chromatography and the title compound (87 mg) was obtained as a light yellow amorphous solid from the n-hexane:ethyl acetate (2:1) fraction.

$^1$H NMR (400 MHz, CDCl$_3$) δ 1.21 (t, J=7.6 Hz, 3H), 1.54 (br s, 9H), 2.72 (q, J=7.6 Hz, 2H), 3.47 (s, 3H), 3.69 (s, 6H), 4.51 (s, 2H), 5.82-5.90 (m, 1H), 6.58-6.65 (m, 1H), 6.65 (s, 2H), 7.08-7.14 (m, 1H), 7.32-7.38 (m, 1H).

Example 11

N-Cyclobutylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine

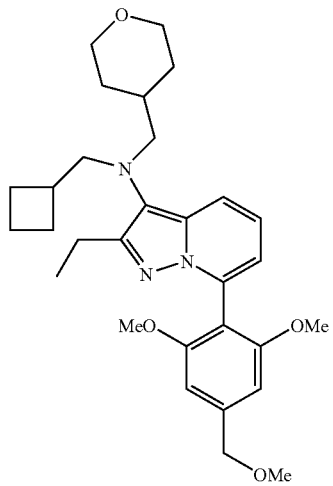

To a solution of tert-butyl N-7-[2,6-dimethoxy-4-(methoxymethyl)phenyl]-2-ethylpyrazolo[1,5-a]pyridin-3-ylcarbamate (43 mg) dissolved in N,N-dimethylformamide (1 mL) was added sodium hydride (60% in oil; 6 mg), and (bromomethyl)cyclobutane (0.013 mL), and the mixture was stirred for 1 hour at room temperature. Water was added to the obtained reaction mixture, which was then extracted with ethyl acetate and washed with brine. The obtained organic extract was dried over anhydrous magnesium sulfate and filtered, and the solvent was evaporated under reduced pressure to obtain a crude product of tert-butyl N-cyclobutylmethyl-N-7-[2,6-dimethoxy-4-(methoxymethyl)phenyl]-2-ethylpyrazolo[1,5-a]pyridin-3-ylcarbamate.

The obtained crude product of tert-butyl N-cyclobutylmethyl-N-7-[2,6-dimethoxy-4-(methoxymethyl)phenyl]-2-ethylpyrazolo[1,5-a]pyridin-3-ylcarbamate was dissolved in ethyl acetate (1 mL) without further purification, and then 4N hydrochloric acid (ethyl acetate solution; 2 mL) was added and the mixture was stirred for 1 hour at 40° C. After neutralizing the obtained reaction mixture with 5N aqueous sodium hydroxide while cooling with ice, extraction was performed with ethyl acetate and the organic extract was washed with brine. It was then dried over anhydrous magnesium sulfate and filtered, and the solvent was evaporated under reduced pressure to afford a crude product of N-cyclobutylmethyl-N-7-[2,6-dimethoxy-4-(methoxymethyl)phenyl]-2-ethylpyrazolo[1,5-a]pyridin-3-ylamine.

To a solution of the obtained residue dissolved in tetrahydrofuran (1 mL) without further purification was added tetrahydropyran-4-carbaldehyde (33 mg) and sodium triacetoxyborohydride (62 mg), and the mixture was stirred for 1 hour at room temperature. Water and then saturated aqueous sodium bicarbonate were added to the obtained reaction mixture, extraction was performed with ethyl acetate, and the organic extract was washed with brine. It was then dried over anhydrous magnesium sulfate and filtered, the solvent was evaporated under reduced pressure, the residue was purified by silica gel column chromatography and the title compound (24 mg) was obtained as a yellow oil from the n-hexane:ethyl acetate (5:1) fraction.

$^1$H NMR (400 MHz, CDCl$_3$) δ 1.21 (t, J=7.6 Hz, 3H), 1.22-1.30 (m, 2H), 1.55-1.62 (m, 3H), 1.71-1.80 (m, 4H), 1.81-1.93 (m, 2H), 2.28-2.36 (m, 1H), 2.72 (q, J=7.6 Hz, 2H), 2.93 (d, J=6.8 Hz, 2H), 3.04 (d, J=7.2 Hz, 2H), 3.27-3.35 (m, 2H), 3.48 (s, 3H), 3.72 (s, 6H), 3.91-3.96 (m, 2H), 4.52 (s, 2H), 6.59 (br d, J=6.8 Hz, 1H), 6.67 (s, 2H), 7.01 (dd, J=6.8, 8.8 Hz, 1H), 7.40 (br d, J=8.8 Hz, 1H).

Similarly to Example 11, the compounds of Example 12 to 14 were synthesized.

Example 12

N-Butyl-N-7-[2,6-dimethoxy-4-(methoxymethyl)phenyl]-2-ethylpyrazolo[1,5-a]pyridin-3-yl-N-tetrahydro-2H-4-pyranylmethylamine

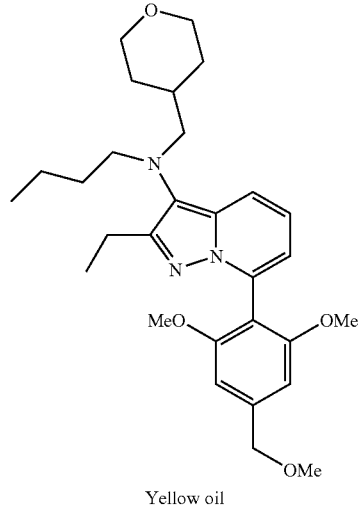

Yellow oil $^1$H NMR (400 MHz, CDCl$_3$) δ 0.86 (t, J=6.8 Hz, 3H), 1.22 (t, J=7.6 Hz, 3H), 1.24-1.40 (m, 6H), 1.50-1.60 (m, 1H), 1.70-1.78 (m, 2H), 2.73 (q, J=7.6 Hz, 2H), 2.96 (d, J=7.2 Hz, 2H), 3.01 (t, J=7.2 Hz, 2H), 3.26-3.35 (m, 2H), 3.49 (s, 3H), 3.73 (s, 6H), 3.90-3.97 (m, 2H), 4.53 (s, 2H), 6.60 (dd, J=1.2, 6.8 Hz, 1H), 6.68 (s, 2H), 7.01 (dd, J=6.8, 8.8 Hz, 1H), 7.42 (dd, J=1.2, 8.8 Hz, 1H).

Example 13

N-7-[2,6-Dimethoxy-4-(methoxymethyl)phenyl]-2-ethylpyrazolo[1,5-a]pyridin-3-yl-N-propyl-N-tetrahydro-2H-4-pyranylmethylamine

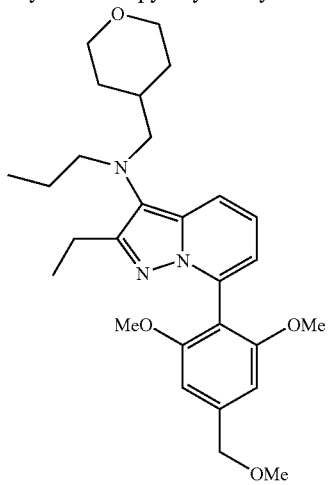

Light yellow amorphous solid $^1$H NMR (400 MHz, CDCl$_3$) δ 0.87 (t, J=7.6 Hz, 3H), 1.20 (t, J=7.2 Hz, 3H), 1.23-1.32 (m, 2H), 1.36-1.45 (m, 2H), 1.52-1.62 (m, 1H), 1.72-1.78 (m, 2H), 2.73 (q, J=7.2 Hz, 2H), 2.96-3.00 (m, 4H), 3.27-3.35 (m, 2H), 3.49 (s, 3H), 3.73 (s, 6H), 3.90-3.97 (m, 2H), 4.53 (s, 2H), 6.60 (dd, J=1.6, 6.8 Hz, 1H), 6.68 (s, 2H), 7.01 (dd, J=6.8, 8.8 Hz, 1H), 7.42 (dd, J=1.6, 8.8 Hz, 1H).

Example 14

N-7-[2,6-Dimethoxy-4-(methoxymethyl)phenyl]-2-ethylpyrazolo[1,5-a]pyridin-3-yl-N-isobutyl-N-tetrahydro-2H-4-pyranylmethylamine

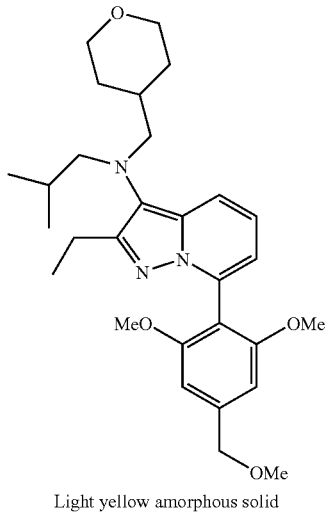

Light yellow amorphous solid $^1$H NMR (400 MHz, CDCl$_3$) δ 0.91 (d, J=6.8 Hz, 6H), 1.20 (t, J=7.6 Hz, 3H), 1.22-1.31 (m, 2H), 1.50-1.62 (m, 2H), 1.72-1.80 (m, 2H), 2.74 (q, J=7.6 Hz, 2H), 2.82 (d, J=7.2 Hz, 2H), 2.91 (d, J=6.8 Hz, 2H), 3.26-3.34 (m, 2H), 3.47 (s, 3H), 3.72 (s, 6H), 3.90-3.96 (m, 2H), 4.52 (s, 2H), 6.58 (dd, J=1.6, 6.8 Hz, 1H), 6.66 (s, 2H), 7.00 (dd, J=6.8, 8.8 Hz, 1H), 7.43 (dd, J=1.6, 8.8 Hz, 1H).

Example 15

7-[2,6-Dimethoxy-4-(methoxymethyl)phenyl]-2-ethylpyrazolo[1,5-a]pyridine-3-amine

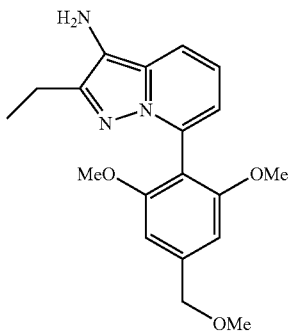

A suspension of 7-[2,6-dimethoxy-4-(methoxymethyl)phenyl]-2-ethyl-3-nitropyrazolo[1,5-a]pyridine (0.7 g) in a mixed solvent of ethanol (35 mL), water (18 mL) and acetic acid (3.5 mL) was added zinc powder (0.7 g) at room temperature, and the reaction mixture was heated and stirred for 30 minutes at 60° C. The reaction mixture was filtered through celite to remove insoluble residue, water was added to the filtrate and extraction was performed with ethyl acetate. The obtained organic extract was washed with brine, saturated aqueous sodium bicarbonate and then brine and dried over anhydrous magnesium sulfate and filtered, after which the solvent was evaporated under reduced pressure. The residue was purified by silica gel column chromatography and the title compound (0.48 g) was obtained as a yellow oil from the n-hexane:ethyl acetate (4:1) fraction.

$^1$H NMR (400 MHz, CDCl$_3$) δ 1.23 (t, J=7.6 Hz, 3H), 2.60-2.98 (m, 2H), 3.47 (s, 3H), 3.70 (s, 6H), 4.51 (s, 2H), 6.40-6.60 (m, 1H), 6.65 (s, 2H), 6.90-7.08 (m, 1H), 7.24-7.38 (m, 1H). MS (ESI)m/z 342 MH$^+$

Example 16 tert-Butyl N-7-[2,6-dimethoxy-4-(methoxymethyl)phenyl]-2-ethylpyrazolo[1,5-a]pyridin-3-ylcarbamate

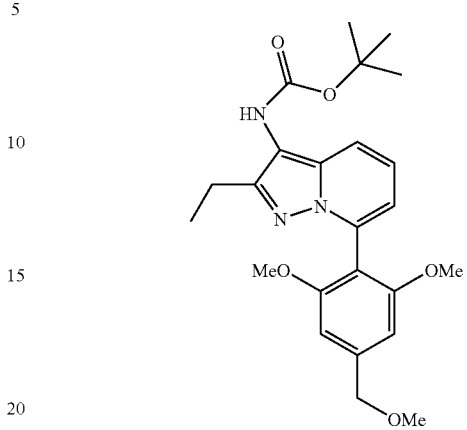

To a solution of 7-[2,6-dimethoxy-4-(methoxymethyl)phenyl]-2-ethylpyrazolo[1,5-a]pyridine-3-amine (0.48 g) dissolved in dichloromethane (4.8 mL) was added triethylamine (0.3 mL) and di-tert-butyl dicarbonate (0.39 mL) at room temperature, and the reaction mixture was stirred overnight at room temperature. Water was added to the obtained reaction mixture and extraction was performed with ethyl acetate. The organic extract was washed with brine, dried over anhydrous magnesium sulfate and filtered, and the solvent was evaporated under reduced pressure. The residue was purified by silica gel column chromatography and the title compound (0.54 g) was obtained as white crystals from the n-hexane:ethyl acetate (1:1) fraction.

$^1$H NMR (400 MHz, CDCl$_3$) δ 1.21 (t, J=7.6 Hz, 3H), 1.54 (br s, 9H), 2.72 (q, J=7.6 Hz, 2H), 3.47 (s, 3H), 3.69 (s, 6H), 4.51 (s, 2H), 5.86 (br s, 1H), 6.61 (d, J=6.8 Hz, 1H), 6.65 (s, 2H), 7.10 (dd, J=6.8, 8.8 Hz, 1H), 7.35 (d, J=8.8 Hz, 1H).

Example 17

N-7-[4-(1-[1-(tert-Butyl)-1,1-dimethylsilyl]oxyethyl)-2,6-dimethoxyphenyl]-2-ethylpyrazolo[1,5-a]pyridin-3-yl-N-cyclopropylmethyl-N-tetrahydro-2H-4-pyranylmethylamine

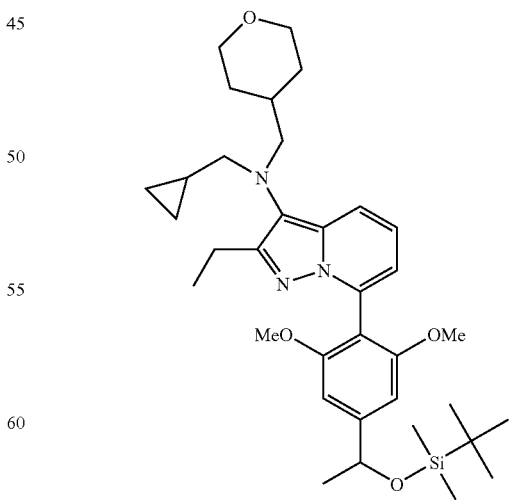

To a solution of N-(7-bromo-2-methoxypyrazolo[1,5-a]pyridin-3-yl)-N-cyclopropylmethylamine (70 mg) dissolved in 1,2-dimethoxyethane (4 mL) and water (2 mL) was added 4-[1-[1-(tert-butyl)-1,1-dimethylsilyl]oxyethyl]-2,6- dimethoxyphenylboric acid (92 mg), tetrakis(triphenylphosphine)palladium(0) (31 mg) and barium hydroxide octahydrate (85 mg), and the mixture was heated and stirred for 1 hour at 80° C. under a nitrogen stream. Ethyl acetate was added to the reaction mixture, and after filtering off the insoluble residue, extraction was performed with ethyl acetate and the organic extract was washed with brine. The obtained organic extract was dried over anhydrous magnesium sulfate and filtered, the solvent was evaporated under reduced pressure, the residue was purified by silica gel column chromatography and the title compound (112 mg) was obtained as a yellow oil from the n-hexane:ethyl acetate (4:1) fraction.

$^1$H NMR (400 MHz, CDCl$_3$) δ –0.07-0.03 (m, 2H), 0.07 (s, 3H), 0.12 (s, 3H), 0.32-0.38 (m, 2H), 0.79-0.88 (m, 1H), 0.96 (s, 9H), 1.21-1.33 (m, 2H), 1.26 (t, J=7.2 Hz, 3H), 1.49 (d, J=6.4 Hz, 3H), 1.51-1.63 (m, 1H), 1.70-1.80 (m, 2H), 2.77 (q, J=7.2 Hz, 2H), 2.84-2.91 (m, 2H), 3.00-3.07 (m, 2H), 3.25-3.35 (m, 2H), 3.70 (s, 6H), 3.89-3.97 (m, 2H), 4.92 (q, J=6.4 Hz, 1H), 6.61 (dd, J=1.3, 6.8 Hz, 1H), 6.67 (s, 1H), 6.68 (s, 1H), 7.00 (dd, J=6.8, 8.8 Hz, 1H), 7.43 (dd, J=1.3, 8.8 Hz, 1H).

Example 18

1-(4-3-[(Cyclopropylmethyl)(tetrahydro-2H-4-pyranylmethyl)amino]-2-ethylpyrazolo[1,5-a]pyridin-7-yl-3,5-dimethoxyphenyl)-1-ethanol

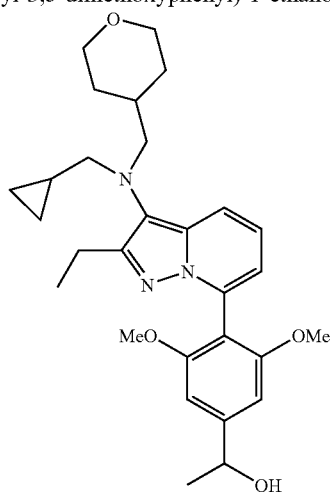

To a solution of N-[7-[4-[1-[1-(tert-butyl)-1,1-dimethylsilyl]oxyethyl]-2,6-dimethoxyphenyl]-2-ethylpyrazolo[1,5-a]pyridin-3-yl]-N-cyclopropylmethyl-N-tetrahydro-2H-4-pyranylmethylamine (112 mg) dissolved in tetrahydrofuran (1 mL) was added tetrabutylammonium fluoride (1M tetrahydrofuran solution; 0.27 mL) at room temperature, and the reaction mixture was stirred for 3 hours at the same temperature. After adding saturated aqueous ammonium chloride to the obtained reaction mixture, extraction was performed with ethyl acetate, the organic extract was washed with brine, dried over anhydrous magnesium sulfate and filtered, and the solvent was evaporated under reduced pressure. The residue was purified by silica gel column chromatography and the title compound (66 mg) was obtained as a light yellow amorphous solid from the n-hexane:ethyl acetate (1:2) fraction.

$^1$H NMR (400 MHz, CDCl$_3$) δ –0.04-0.12 (m, 2H), 0.32-0.38 (m, 2H), 0.78-0.88 (m, 1H), 1.21 (t, J=7.5 Hz, 3H), 1.21-1.33 (m, 2H), 1.50-1.65 (m, 4H), 1.70-1.80 (m, 2H), 2.76 (q, J=7.5 Hz, 2H), 2.84-2.91 (m, 2H), 3.01-3.08 (m, 2H), 3.26-3.37 (m, 2H), 3.73 (s, 6H), 3.88-3.98 (m, 2H), 4.91-4.99 (m, 1H), 6.59 (dd, J=1.3, 6.8 Hz, 1H), 6.70 (s, 1H), 6.74 (s, 1H), 7.01 (dd, J=6.8, 8.8 Hz, 1H), 7.45 (dd, J=1.3, 8.8 Hz, 1H).

Example 19

4-3-[(Cyclopropylmethyl)(tetrahydro-2H-4-pyranylmethyl)amino]-2-ethylpyrazolo[1,5-a]pyridin-7-yl-3,5-dimethoxybenzaldehyde

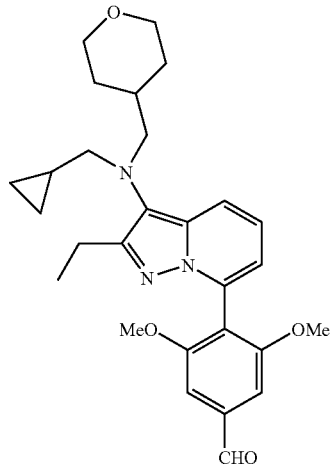

To a solution of (4-3-[(cyclopropylmethyl)(tetrahydro-2H-4-pyranylmethyl)amino]-2-ethylpyrazolo[1,5-a]pyridin-7-yl-3,5-dimethoxyphenyl)methanol (50 mg) in acetone (2 mL) was added activated manganese(IV) oxide (250 mg) at room temperature, and the reaction mixture was stirred for 12 hours. The manganese oxide was filtered out from the reaction mixture and the filtrate was evaporated under reduced pressure. The residue was purified by silica gel column chromatography and the title compound (41 mg) was obtained as a yellow solid from the ethyl acetate:n-hexane (1:2) fraction.

$^1$H NMR (400 MHz, CDCl$_3$) δ –0.02-0.01 (m, 2H), 0.30-0.40 (m, 2H), 0.80-0.88 (m, 1H), 1.18-1.32 (m, 5H), 1.54-1.62 (m, 1H), 1.72-1.80 (m, 2H), 2.75 (q, J=7.6 Hz, 2H), 2.88 (d, J=6.8 Hz, 2H), 3.05 (d, J=6.8 Hz, 2H), 3.25-3.34 (m, 2H), 3.79 (s, 6H), 3.93-3.98 (m, 2H), 6.61 (dd, J=1.2, 6.8 Hz, 1H), 7.03 (dd, J=6.8, 8.8 Hz, 1H), 7.21 (s, 2H), 7.49 (dd, J=1.2, 8.8 Hz, 1H), 10.02 (s, 1H).

Example 20

N-Butyl-N-7-[4-(ethoxymethyl)-2,6-dimethoxyphenyl]-2-ethylpyrazolo[1,5-a]pyridin-3-yl-N-tetrahydro-2H-4-pyranylmethylamine

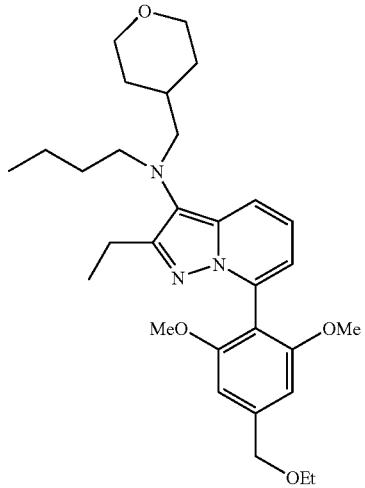

N-(7-Bromo-2-ethylpyrazolo[1,5-a]pyridin-3-yl)-N-butyl-N-tetrahydro-2H-4-pyranylmethylamine (150 mg) and 4-(hydroxymethyl)-2,6-dimethoxyphenylboric acid (250 mg) were reacted with the same manner as Example 1 to afford (4-3-[butyl(tetrahydro-2H-4-pyranylmethyl)amino]-2-ethylpyrazolo[1,5-a]pyridin-7-yl-3,5-dimethoxyphenyl)methanol (189 mg) as a yellow oil.

To a solution of the obtained (4-3-[butyl(tetrahydro-2H-4-pyranylmethyl)amino]-2-ethylpyrazolo[1,5-a]pyridin-7-yl-3,5-dimethoxyphenyl)methanol (189 mg) in N,N-dimethylformamide (15 mL) was added sodium hydride (60% oil; 24 mg) at room temperature, and the reaction mixture was stirred for 30 minutes. Next, to the resulting mixture was added iodoethane (0.047 mL), and the mixture was stirred for 1 hour at 60° C. After completion of the reaction, ice was added to the reaction mixture while cooling with ice, extraction was performed with ethyl acetate and the organic extract was washed with brine and dried over anhydrous magnesium sulfate, after which the solvent was evaporated under reduced pressure. The residue was purified by silica gel column chromatography (10 g) and the title compound (111 mg) was obtained as yellow crystals from the ethyl acetate: n-hexane (1:2) fraction.

$^1$H NMR (400 MHz, CDCl$_3$) δ 0.86 (t, J=7.0 Hz, 3H), 1.20 (t, J=7.5 Hz, 3H), 1.31 (t, J=7.0 Hz, 3H), 1.17-1.42 (m, 6H), 1.50-1.64 (m, 1H), 1.70-1.79 (m, 2H), 2.73 (q, J=7.5 Hz, 2H), 2.96 (d, J=7.0 Hz, 2H), 3.01 (t, J=7.0 Hz, 2H), 3.33 (dt, J=1.6, 12.0 Hz, 2H), 3.64 (q, J=7.0 Hz, 2H), 3.72 (s, 6H), 3.90-4.00 (m, 2H), 4.57 (s, 2H), 6.59 (dd, J=1.1, 6.8 Hz, 1H), 6.69 (s, 2H), 7.01 (dd, J=6.9, 8.9 Hz, 1H), 7.42 (dd, J=1.3, 8.8 Hz, 1H).

Similarly to Example 20, the compounds of Example 21 to 27 were synthesized.

Example 21

N-Cyclopropylmethyl-N-(7-2,6-dimethoxy-4-[(2-piperidinoethoxy)methyl]phenyl-2-ethylpyrazolo[1,5-a]pyridin-3-yl)-N-tetrahydro-2H-4-pyranylmethylamine Yellow oil

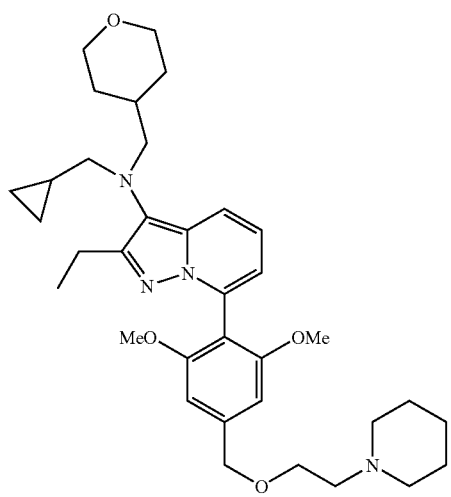

$^1$H NMR (400 MHz, CDCl$_3$) δ −0.05-0.02 (m, 2H), 0.32-0.38 (m, 2H), 0.80-0.88 (m, 1H), 1.18-1.32 (m, 5H), 1.40-1.48 (m, 2H), 1.52-1.68 (m, 5H), 1.70-1.78 (m, 2H), 2.40-2.55 (m, 4H), 2.64 (t, J=6.0 Hz, 2H), 2.76 (q, J=7.2 Hz, 2H), 2.87 (d, J=6.8 Hz, 2H), 3.04 (d, J=6.8 Hz, 2H), 3.31 (t, J=11.2 Hz, 2H), 3.68 (t, J=6.4 Hz, 2H), 3.71 (s, 6H), 3.90-3.97 (m, 2H), 4.59 (s, 2H), 6.58 (dd, J=0.8, 6.8 Hz, 1H), 6.68 (s, 2H), 7.00 (dd, J=6.8, 8.4 Hz, 1H), 7.44 (br d, J=8.8 Hz, 1H).

Example 22

N-Cyclopropylmethyl-N-(7-2,6-dimethoxy-4-[(2-methoxyethoxy)methyl]phenyl-2-ethylpyrazolo[1,5-a]pyridin-3-yl)-N-tetrahydro-2H-4-pyranylmethylamine Yellow oil

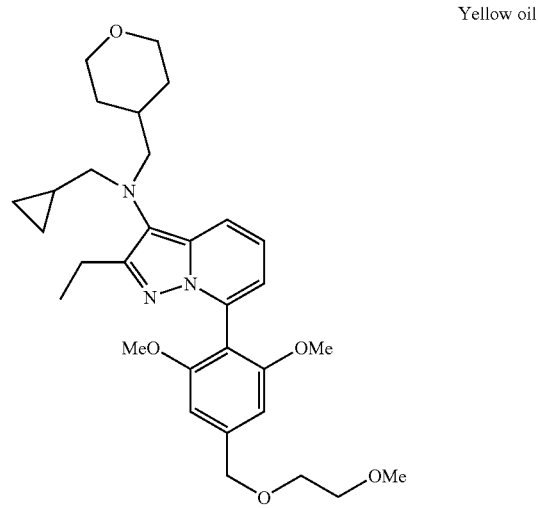

$^1$H NMR (400 MHz, CDCl$_3$) δ −0.02-0.01 (m, 2H), 0.30-0.38 (m, 2H), 0.80-0.90 (m, 1H), 1.19-1.30 (m, 5H), 1.50-1.62 (m, 1H), 1.72-1.80 (m, 2H), 2.75 (q, J=7.6 Hz, 2H), 2.87 (d, J=6.8 Hz, 2H), 3.04 (d, J=6.8 Hz, 2H), 3.25-3.35 (m, 2H), 3.43 (s, 3H), 3.62-3.65 (m, 2H), 3.71-3.73 (m, 8H), 3.90-3.98 (m, 2H), 4.64 (s, 2H), 6.57 (dd, J=1.6, 6.8 Hz, 1H), 6.70 (s, 2H), 7.00 (dd, J=6.8, 9.2 Hz, 1H), 7.44 (dd, J=1.2, 8.8 Hz, 1H).

Example 23

N-7-[4-(Ethoxymethyl)-2,6-dimethoxyphenyl]-2-ethylpyrazolo[1,5-a]pyridin-3-yl-N-propyl-N-tetrahydro-2H-4-pyranylmethylamine Yellow oil

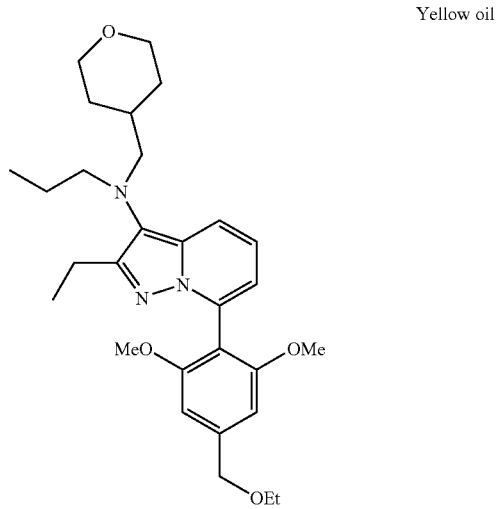

$^1$H NMR (400 MHz, CDCl$_3$) δ 0.87 (t, J=7.4 Hz, 3H), 1.20 (t, J=7.5 Hz, 3H), 1.31 (t, J=7.0 Hz, 3H), 1.18-1.33 (m, 2H), 1.34-1.47 (m, 2H), 1.50-1.65 (m, 1H), 1.70-1.80 (m, 2H), 2.74 (q, J=7.5 Hz, 2H), 2.96 (d, J=7.1 Hz, 2H), 2.93-3.02 (m, 2H), 3.31 (dt, J=1.8, 12.0 Hz, 2H), 3.64 (q, J=7.0 Hz, 2H), 3.72 (s, 6H), 3.90-4.98 (m, 2H), 4.57 (s, 2H), 6.59 (dd, J=1.4, 7.0 Hz, 1H), 6.69 (s, 2H), 7.01 (dd, J=7.0, 8.8 Hz, 1H), 7.42 (dd, J=1.3, 8.8 Hz, 1H).

Example 24

N-Cyclopropylmethyl-N-7-[2,6-dimethoxy-4-(2-methoxymethyl)phenyl]-2-ethylpyrazolo[1,5-a]pyridin-3-yl-N-tetrahydro-2H-4-pyranylmethylamine Light green oil

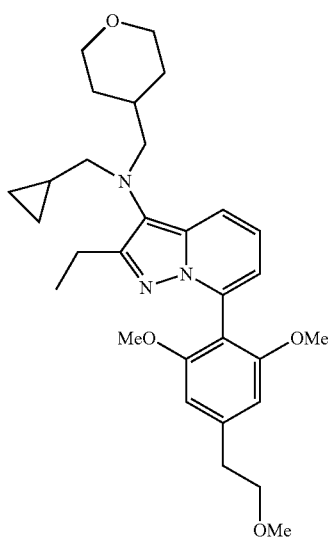

¹H NMR (400 MHz, CDCl₃) δ −0.04-0.02 (m, 2H), 0.32-0.38 (m, 2H), 0.78-0.88 (m, 1H), 1.21 (t, J=7.6 Hz, 3H), 1.22-1.32 (m, 2H), 1.52-1.65 (m, 1H), 1.70-1.80 (m, 2H), 2.75 (q, J=7.6 Hz, 2H), 2.87 (d, J=6.8 Hz, 2H), 2.94 (t, J=6.8 Hz, 2H), 3.03 (d, J=6.8 Hz, 2H), 3.26-3.34 (m, 2H), 3.41 (s, 3H), 3.68 (s, 6H), 3.66-3.78 (m, 2H), 3.90-3.96 (m, 2H), 6.55 (s, 2H), 6.58 (dd, J=1.2, 6.8 Hz, 1H), 6.99 (dd, J=6.8, 8.8 Hz, 1H), 7.42 (dd, J=1.2, 8.8 Hz, 1H).

Example 25

N-Cyclopropylmethyl-N-(7-2,6-dimethoxy-4-[(2-morpholinoethoxy)methyl]phenyl-2-ethylpyrazolo[1,5-a]pyridin-3-yl)-N-tetrahydro-2H-4-pyranylmethylamine

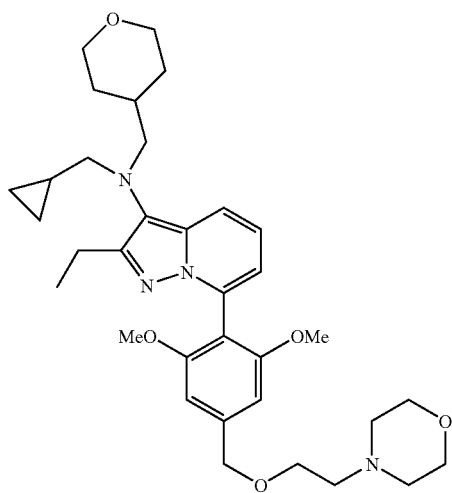

Yellow crystal

¹H NMR (400 MHz, CDCl₃) δ −0.02-0.01 (m, 2H), 0.33-0.36 (m, 2H), 0.80-0.84 (m, 1H), 1.19-1.28 (m, 5H), 1.50-1.60 (m, 1H), 1.70-1.80 (m, 2H), 2.52-2.58 (m, 4H), 2.67 (t, J=5.6 Hz, 2H), 2.75 (q, J=7.6 Hz, 2H), 2.87 (d, J=6.8 Hz, 2H), 3.04 (d, J=7.2 Hz, 2H), 3.30 (dt, J=2.0, 12.0 Hz, 2H), 3.68 (t, J=5.6 Hz, 2H), 3.71 (s, 6H), 3.75 (t, J=4.8 Hz, 4H), 3.91-3.95 (m, 2H), 4.60 (s, 2H), 6.58 (dd, J=1.6, 6.8 Hz, 1H), 6.67 (s, 2H), 7.00 (dd, J=6.8, 8.8 Hz, 1H), 7.44 (dd, J=1.6, 8.8 Hz, 1H)

Example 26

N-Cyclopropylmethyl-N-(7-2,6-dimethoxy-4-[3-(2-morpholinoethoxy)propyl]phenyl-2-ethylpyrazolo[1,5-a]pyridin-3-yl)-N-tetrahydro-2H-4-pyranylmethylamine Yellow oil

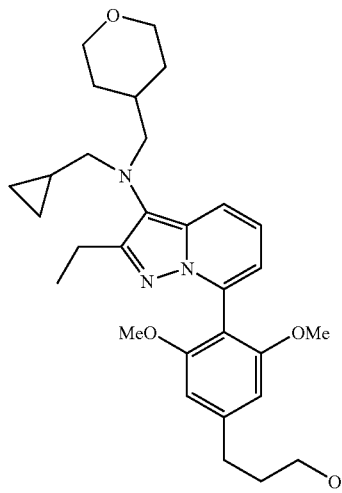

¹H NMR (400 MHz, CDCl₃) δ −0.03-0.01 (m, 2H), 0.33-0.37 (m, 2H), 0.78-0.88 (m, 1H), 1.17-1.35 (m, 5H), 1.50-1.60 (m, 1H), 1.70-1.78 (m, 2H), 1.95-2.02 (m, 2H), 2.45-2.58 (m, 6H), 2.63 (t, J=6.0 Hz, 2H), 2.72-2.79 (m, 4H), 2.87 (d, J=6.8 Hz, 2H), 3.04 (d, J=6.8 Hz, 2H), 3.30 (dt, J=2.0, 12.0 Hz, 2H), 3.54 (t, J=6.4 Hz, 2H), 3.62 (t, J=6.0 Hz, 2H), 3.69-3.75 (m, 8H), 3.92-3.95 (m, 2H), 6.52 (s, 2H), 6.59 (dd, J=1.2, 6.4 Hz, 1H), 7.00 (d, J=6.8, 8.8 Hz, 1H), 7.43 (dd, J=1.6, 7.8 Hz, 1H).

Example 27

N-Cyclopropylmethyl-N-7-[2,6-dimethoxy-4-(3-methoxypropyl)phenyl]-2-ethylpyrazolo[1,5-a]pyridin-3-yl-N-tetrahydro-2H-4-pyranylmethylamine Yellow oil

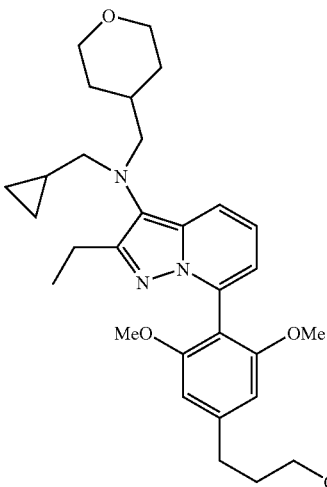

¹H NMR (400 MHz, CDCl₃) δ −0.03-0.01 (m, 2H), 0.33-0.37 (m, 2H), 0.81-0.85 (m, 1H), 1.19-1.31 (m, 5H), 1.50-1.60 (m, 1H), 1.72-1.80 (m, 2H), 1.94-2.01 (m, 2H), 2.73-2.79 (m, 4H), 2.87 (d, J=6.4 Hz, 2H), 3.04 (d, J=6.8 Hz, 2H), 3.30 (dt, J=2.0, 11.6 Hz, 2H), 3.33 (s, 3H), 3.48 (t, J=6.4 Hz, 2H), 3.70 (s, 6H), 3.92-3.95 (m, 2H), 6.53 (s, 2H), 6.59 (dd, J=1.2, 6.8 Hz, 1H), 7.00 (dd, J=6.4, 8.8 Hz, 1H), 7.43 (dd, J=1.2, 8.4 Hz, 1H).

Example 28

N-7-[4-(Chloromethyl)-2,6-dimethoxyphenyl]-2-ethylpyrazolo[1,5-a]pyridin-3-yl-N-cyclopropylmethyl-N-tetrahydro-2H-4-pyranylmethylamine

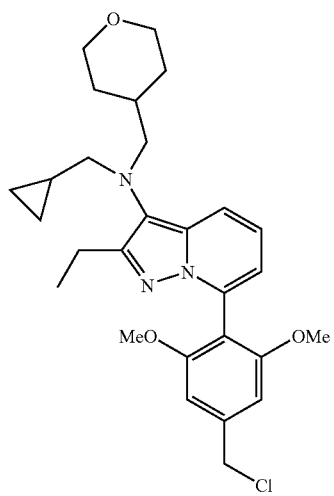

To a solution of (4-3-[(cyclopropylmethyl) (tetrahydro-2H-4-pyranylmethyl)amino]-2-ethylpyrazolo[1,5-a]pyridin-7-yl-3,5-dimethoxyphenyl)methanol (122 mg) in dichloromethane (5 mL) was added triethylamine (0.076 mL), methanesulfonyl chloride (0.023 mL) and 4-(dimethylamino)pyridine (0.5 mg) at room temperature, and the reaction mixture was stirred for 2 hours. After completion of the reaction, water was added to the reaction mixture, extraction was performed with ethyl acetate and the organic extract was washed with brine and dried over anhydrous magnesium sulfate, after which the solvent was evaporated under reduced pressure. The residue was purified by silica gel column chromatography (15 g) and the title compound (45 mg) was obtained as a yellow amorphous solid from the ethyl acetate:n-hexane (1:2) fraction.

$^1$H NMR (400 MHz, CDCl$_3$) δ −0.02-0.04 (m, 2H), 0.33-0.41 (m, 2H), 0.79-0.92 (m, 1H), 1.23 (t, J=7.6 Hz, 3H), 1.20-1.36 (m, 2H), 1.53-1.67 (m, 1H), 1.72-1.82 (m, 2H), 2.77 (q, J=7.6 Hz, 2H), 2.89 (d, J=6.8 Hz, 2H), 3.06 (d, J=7.0 Hz, 2H), 3.32 (dt, J=2.0, 12.0 Hz, 2H), 3.75 (s, 6H), 3.90-4.00 (m, 2H), 4.66 (s, 2H), 6.60 (dd, J=1.4, 6.8 Hz, 1H), 6.74 (s, 2H), 7.02 (dd, J=6.8, 8.8 Hz, 1H), 7.47 (dd, J=1.5, 8.8 Hz, 1H).

Example 29

N-Cyclopropylmethyl-N-2-ethyl-7-[4-(isopropoxymethyl)-2,6-dimethoxyphenyl]pyrazolo[1,5-a]pyridin-3-yl-N-tetrahydro-2H-4-pyranylmethylamine

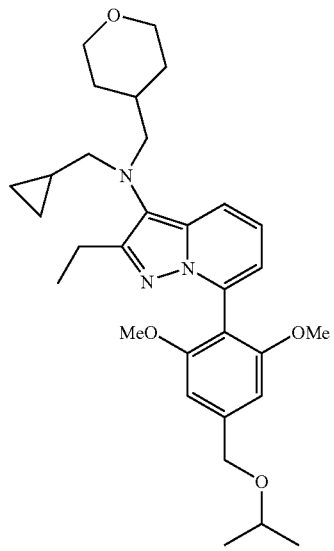

To a solution of 2-propanol (8 μL) in N,N-dimethylformamide (1.5 mL) was added sodium hydride (60% in oil; 4.3 mg) at room temperature, and the reaction mixture was stirred for 15 minutes. A solution of N-7-[4-(chloromethyl)-2,6-dimethoxyphenyl]-2-ethylpyrazolo[1,5-a]pyridin-3-yl-N-cyclopropylmethyl-N-tetrahydro-2H-4-pyranylmethylamine (45 mg) in N,N-dimethylformamide (3.5 mL) and sodium iodide (0.5 mg) were added to the obtained reaction mixture, and then the reaction mixture was stirred for 20 minutes at 40° C. and further stirred for 20 minutes at 80° C. To the obtained reaction mixture was added ice, extraction was performed with ethyl acetate and the organic extract was washed with brine and dried over anhydrous magnesium sulfate, after which the solvent was evaporated under reduced pressure. The residue was purified by silica gel column chromatography (10 g) and the title compound (9 mg) was obtained as a yellow oil from the ethyl acetate:n-hexane (1:2) fraction.

$^1$H NMR (400 MHz, CDCl$_3$) δ −0.03-0.04 (m, 2H), 0.32-0.41 (m, 2H), 0.79-0.92 (m, 1H), 1.22 (t, J=7.6 Hz, 3H), 1.29 (d, J=6.0 Hz, 6H), 1.20-1.36 (m, 2H), 1.53-1.67 (m, 1H), 1.72-1.82 (m, 2H), 2.77 (q, J=7.5 Hz, 2H), 2.89 (d, J=6.6 Hz, 2H), 3.06 (d, J=7.0 Hz, 2H), 3.32 (dt, J=2.0, 12.0 Hz, 2H), 3.73 (s, 6H), 3.70-3.84 (m, 1H), 3.90-4.00 (m, 2H), 4.59 (s, 2H), 6.59 (dd, J=1.3, 6.8 Hz, 1H), 6.70 (s, 2H), 7.01 (dd, J=6.8, 8.8 Hz, 1H), 7.45 (dd, J=1.5, 8.8 Hz, 1H).

Example 30

3-(4-3-[(Cyclopropylmethyl)(tetrahydro-2H-4-pyranylmethyl)amino]-2-ethylpyrazolo[1,5-a]pyridin-7-yl-3,5-dimethoxyphenyl)propyl methanesulfonate

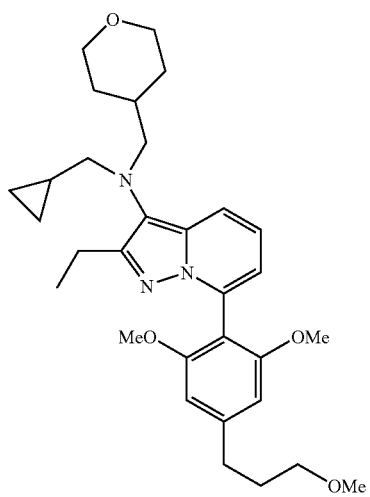

To a solution of 3-(4-3-[(cyclopropylmethyl)(tetrahydro-2H-4-pyranylmethyl)amino]-2-ethylpyrazolo[1,5-a]pyridin-7-yl-3,5-dimethoxyphenyl)-1-propanol (190 mg) in dichloromethane (20 mL) was added triethylamine (0.062 mL), methanesulfonyl chloride (51 mg) and 4-(dimethylamino) pyridine (0.5 mg) at room temperature, and the reaction mixture was stirred for 2 hours. After completion of the reaction, water was added to the reaction mixture, extraction was performed with ethyl acetate and the organic extract was washed with brine and dried over anhydrous magnesium sulfate, after which the solvent was evaporated under reduced pressure. The residue was purified by silica gel column chromatography (15 g) and the title compound (179 mg) was obtained as a yellow oil from the ethyl acetate:n-hexane (1:2) fraction.

$^1$H NMR (400 MHz, CDCl$_3$) δ −0.03-0.01 (m, 2H), 0.33-0.37 (m, 2H), 0.81-0.85 (m, 1H), 1.19-1.35 (m, 5H), 1.50-1.57 (m, 1H), 1.72-1.77 (m, 2H), 1.85-2.00 (m, 2H), 2.70-2.90 (m, 6H), 3.04-3.10 (m, 5H), 3.25-3.35 (m, 2H), 3.70 (s, 6H), 4.33 (t, J=6.4 Hz, 2H), 3.91-3.99 (m, 2H), 6.53 (s, 2H), 6.59-6.62 (m, 1H), 6.95-7.05 (m, 1H), 7.43-7.48 (m, 1H).

Example 31

N-Cyclopropylmethyl-N-7-[2,6-dimethoxy-4-(3-morpholinopropyl)phenyl]-2-ethylpyrazolo[1,5-a]pyridin-3-yl-N-tetrahydro-2H-4-pyranylmethylamine

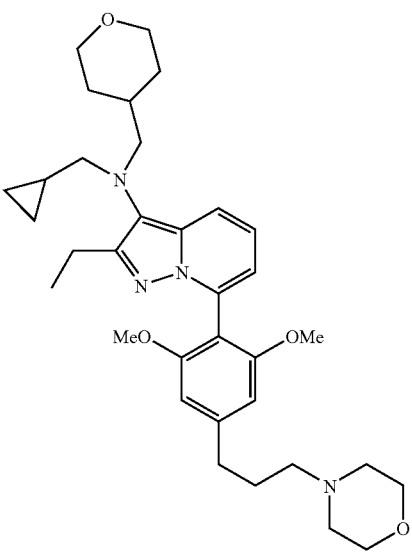

To a solution of 3-(4-3-[(cyclopropylmethyl)(tetrahydro-2H-4-pyranylmethyl)amino]-2-ethylpyrazolo[1,5-a]pyridin-7-yl-3,5-dimethoxyphenyl)propyl methanesulfonate (50 mg) in dichloromethane (10 mL) was added morpholine (60 mg) at room temperature, and the reaction mixture was stirred for 12 hours at the same temperature. After completion of the reaction, water was added to the reaction mixture, extraction was performed with ethyl acetate and the organic extract was washed with brine and dried over anhydrous magnesium sulfate, after which the solvent was evaporated under reduced pressure. The residue was purified by silica gel column chromatography (10 g) and the title compound (16 mg) was obtained as a yellow oil from the ethyl acetate fraction.

$^1$H NMR (400 MHz, CDCl$_3$) δ −0.02-0.02 (m, 2H), 0.35-0.40 (m, 2H), 0.80-0.90 (m, 1H), 1.20-1.35 (m, 5H), 1.55-1.60 (m, 1H), 1.73-1.80 (m, 2H), 1.90-1.98 (m, 2H), 2.45-1.52 (m, 6H), 2.70-2.81 (m, 4H), 2.89 (d, J=7.2 Hz, 2H), 3.06 (d, J=7.2 Hz, 2H), 3.32 (br t, J=9.6 Hz, 2H), 3.70-3.79 (m, 10H), 3.93-3.97 (m, 2H), 6.54 (s, 2H), 6.61 (dd, J=0.8, 6.8 Hz, 1H), 7.06 (dd, J=6.8, 8.8 Hz, 1H), 7.45 (dd, J=1.2, 8.8 Hz, 1H).

Example 32

N-Cyclopropylmethyl-N-7-[2,6-dimethoxy-4-(morpholinomethyl)phenyl]-2-ethylpyrazolo[1,5-a]pyridin-3-yl-N-tetrahydro-2H-4-pyranylmethylamine

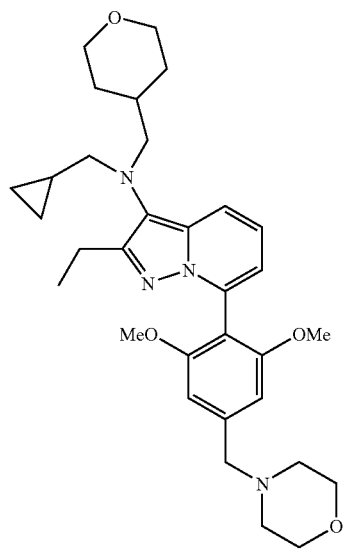

To a solution of 4-3-[(cyclopropylmethyl)(tetrahydro-2H-4-pyranylmethyl)amino]-2-ethylpyrazolo[1,5-a]pyridin-7-yl-3,5-dimethoxybenzaldehyde (15 mg) in acetic acid (0.5 mL) and tetrahydrofuran (0.5 mL) was added morpholine (3.2 mg) while stirring at room temperature, and then sodium triacetoxyborohydride (8 mg) was added and the reaction mixture was stirred for 2 hours. Water was added to the obtained reaction mixture and extraction was performed with ethyl acetate. The obtained organic extract was dried over anhydrous magnesium sulfate and filtered, and the solvent was evaporated under reduced pressure. The obtained residue was purified by silica gel column chromatography and the title compound (8.5 mg) was obtained as a yellow oil from the ethyl acetate:n-hexane (2:1) fraction.

$^1$H NMR (400 MHz, CDCl$_3$) δ −0.04-0.01 (m, 2H), 0.32-0.38 (m, 2H), 0.78-0.88 (m, 1H), 1.18-1.32 (m, 5H), 1.50-1.62 (m, 1H), 1.72-1.78 (m, 2H), 2.48-2.58 (m, 4H), 2.76 (q, J=8.0 Hz, 2H), 2.87 (d, J=6.8 Hz, 2H), 3.04 (d, J=7.2 Hz, 2H), 3.26-3.34 (m, 2H), 3.54 (s, 2H), 3.71 (s, 6H), 3.75-3.78 (m, 4H), 3.91-3.95 (m, 2H), 6.59 (br d, J=6.8 Hz, 1H), 6.69 (s, 2H), 7.00 (dd, J=6.8, 8.8 Hz, 1H), 7.44 (br d, J=8.8 Hz, 1H).

Similarly to Example 32, the compounds of Example 33 and 34 were synthesized.

Example 33

N3-Cyclopropylmethyl-N3-tetrahydro-2H-4-pyranylmethyl-7-4-[(dimethylamino)methyl]-2,6-dimethoxyphenyl-2-ethylpyrazolo[1,5-a]pyridin-3-amine Yellow oil

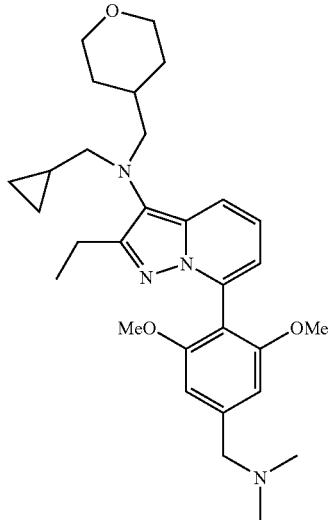

$^1$H NMR (400 MHz, CDCl$_3$) δ −0.03-0.01 (m, 2H), 0.32-0.37 (m, 2H), 0.78-0.90 (m, 1H), 1.18-1.32 (m, 5H), 1.50-1.62 (m, 1H), 1.70-1.78 (m, 2H), 2.34 (br s, 6H), 2.76 (q, J=7.6 Hz, 2H), 2.87 (d, J=6.8 Hz, 2H), 3.04 (d, J=6.8 Hz, 2H), 3.25-3.35 (m, 2H), 3.45-3.52 (m, 2H), 3.71 (s, 6H), 3.90-3.95 (m, 2H), 6.60 (dd, J=1.2, 6.8 Hz, 1H), 6.67 (s, 2H), 7.00 (dd, J=7.2, 8.4 Hz, 1H), 7.44 (dd, J=1.2, 8.8 Hz, 1H).

Example 34

N-Cyclopropylmethyl-N-7-[2,6-dimethoxy-4-(tetrahydro-1H-1-pyrrolylmethyl)phenyl]-2-ethylpyrazolo[1,5-a]pyridin-3-yl-N-tetrahydro-2H-4-pyranylmethylamine Yellow oil

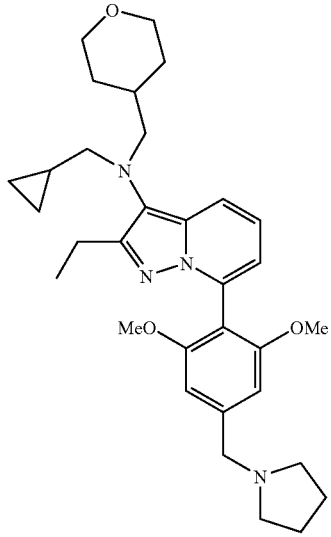

$^1$H NMR (400 MHz, CDCl$_3$) δ −0.02-0.00 (m, 2H), 0.30-0.40 (m, 2H), 0.80-0.88 (m, 1H), 1.19-1.32 (m, 5H), 1.50-1.64 (m, 1H), 1.72-1.78 (m, 2H), 1.80-1.90 (m, 4H), 2.56-2.68 (m, 4H), 2.76 (q, J=7.6 Hz, 2H), 2.87 (d, J=6.8 Hz, 2H), 3.04 (d, J=6.8 Hz, 2H), 3.26-3.34 (m, 2H), 3.67 (br s,

2H), 3.71 (s, 6H), 3.92-3.95 (m, 2H), 6.59 (dd, J=0.8, 6.8 Hz, 1H), 6.69 (s, 2H), 6.98-7.02 (m, 1H), 7.44 (br d, J=8.8 Hz, 1H).

Example 35 tert-Butyl N-7-[2,6-dimethoxy-4-(methoxymethyl) phenyl]-2-methylpyrazolo[1,5-a]pyridin-3-ylcarbamate

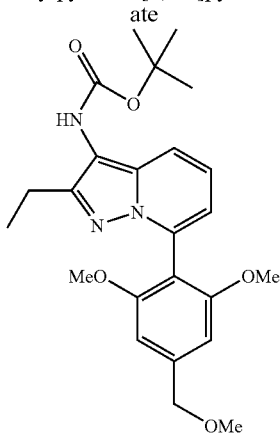

To a solution of tert-butyl N-(7-bromo-2-methylpyrazolo[1,5-a]pyridin-3-yl)carbamate (300 mg) dissolved in a mixture of 1,2-dimethoxyethane (10 mL) and water (5 mL) was added 2,6-dimethoxy-4-methoxymethylphenylboric acid (353 mg), tetrakis(triphenylphosphine)palladium(0) (159 mg) and barium hydroxide octahydrate (435 mg), and the reaction mixture was heated and stirred for 6 hours at 80° C. under a nitrogen stream. Water was added to the obtained reaction mixture, extraction was performed with ethyl acetate, the organic extract was washed with brine, dried over anhydrous magnesium sulfate and filtered, and the solvent was evaporated under reduced pressure. The residue was purified by silica gel column chromatography and the title compound (176 mg) was obtained as a light brown oil from the n-hexane:ethyl acetate (1:1) fraction.

$^1$H NMR (400 MHz, CDCl$_3$) δ 1.54 (br s, 9H), 3.32 (s, 3H), 3.47 (s, 3H), 3.69 (s, 6H), 4.51 (s, 2H), 5.86-5.92 (m, 1H), 6.56-6.61 (m, 1H), 6.65 (s, 2H), 7.11 (dd, J=6.8, 8.8 Hz, 1H), 7.34 (dd, J=1.2, 8.8 Hz, 1H).

Example 36

N-Cyclopropylmethyl-N-7-[2,6-dimethoxy-4-(methoxymethyl)phenyl]-2-methylpyrazolo[1,5-a]pyridin-3-ylamine

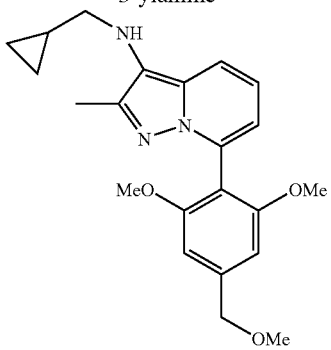

To a solution of tert-butyl N-7-[2,6-dimethoxy-4-(methoxymethyl)phenyl]-2-methylpyrazolo[1,5-a]pyridin-3-ylcarbamate (175 mg) dissolved in N,N-dimethylformamide (4 mL) was added sodium hydride (60% in oil; 25 mg) and (bromomethyl)cyclopropane (0.047 mL), and the reaction mixture was stirred for 1 hour at 40° C. Water was added to the obtained reaction mixture, extraction was performed with ethyl acetate, and the organic extract was washed with brine. The obtained organic extract was dried over anhydrous magnesium sulfate and filtered, and the solvent was evaporated under reduced pressure to afford a crude product of tert-butyl N-cyclopropylmethyl-N-7-[2,6-dimethoxy-4-(methoxymethyl)phenyl]-2-methylpyrazolo[1,5-a]pyridin-3-ylcarbamate.

The obtained crude product of tert-butyl N-cyclopropylmethyl-N-7-[2,6-dimethoxy-4-(methoxymethyl)phenyl]-2-methylpyrazolo[1,5-a]pyridin-3-ylcarbamate was dissolved in ethyl acetate (5 mL) without purification, 4N hydrochloric acid (ethyl acetate solution; 10 mL) was added thereto at room temperature, and the reaction mixture was stirred for 1 hour at 40° C. After neutralizing the reaction mixture with a 5N aqueous sodium hydroxide solution while cooling with ice, extraction was performed with ethyl acetate, the organic extract was washed with brine, dried over anhydrous magnesium sulfate and filtered, the solvent was evaporated under reduced pressure, the residue was purified by silica gel column chromatography and the title compound (100 mg) was obtained as a yellow oil from the n-hexane:ethyl acetate (1:2) fraction.

$^1$H NMR (400 MHz, CDCl$_3$) δ 0.15-0.20 (m, 2H), 0.48-0.54 (m, 2H), 1.02-1.10 (m, 1H), 2.35 (s, 3H), 2.88 (d, J=6.8 Hz, 2H), 3.47 (s, 3H), 3.70 (s, 6H), 4.51 (s, 2H), 6.63 (dd, J=1.2, 6.8 Hz, 1H), 6.65 (s, 2H), 6.99 (dd, J=6.8, 8.8 Hz, 1H), 7.36-7.40 (m, 1H).

Example 37

N-Cyclopropylmethyl-N-7-[2,6-dimethoxy-4-(methoxymethyl)phenyl]-2-methylpyrazolo[1,5-a]pyridin-3-yl-N-tetrahydro-2H-4-pyranylmethylamine

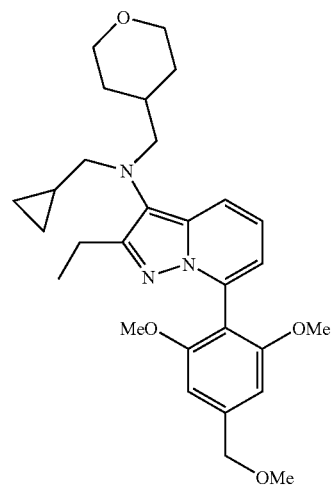

To a solution of N-cyclopropylmethyl-N-7-[2,6-dimethoxy-4-(methoxymethyl)phenyl]-2-methylpyrazolo[1,5-a]pyridin-3-ylamine (60 mg) dissolved in tetrahydrofuran (3 mL) was added tetrahydropyran-4-carbaldehyde (36 mg) and sodium triacetoxyborohydride (67 mg), and the reaction mixture was stirred for 1 hour at room temperature. Water and then saturated aqueous sodium bicarbonate were added to the obtained reaction mixture, extraction was performed with ethyl acetate, the organic extract was washed with brine, dried over anhydrous magnesium sulfate and filtered, and the solvent was evaporated under reduced pressure. The residue was purified by silica gel column chromatography, and the crystals obtained from the n-hexane:ethyl acetate (1:1) fraction were filtered, washed with n-hexane and then dried to afford the title compound (63 mg) as light yellow crystals.

¹H NMR (400 MHz, CDCl₃) δ −0.05-0.02 (m, 2H), 0.31-0.36 (m, 2H), 0.78-0.88 (m, 1H), 1.20-1.32 (m, 2H), 1.54-1.64 (m, 1H), 1.72-1.78 (m, 2H), 2.34 (s, 3H), 2.85 (d, J=7.2 Hz, 2H), 3.03 (d, J=7.2 Hz, 2H), 3.26-3.34 (m, 2H), 3.47 (s, 3H), 3.71 (s, 6H), 3.90-3.96 (m, 2H), 4.51 (s, 2H), 6.53 (dd, J=1.2, 6.8 Hz, 1H), 6.66 (s, 2H), 7.00 (dd, J=6.8, 8.8 Hz, 1H), 7.42 (dd, J=1.2, 8.8 Hz, 1H).

Example 38

N-Cyclopropylmethyl-N-7-[2,6-dimethoxy-4-(methoxymethyl)phenyl]-2-methylpyrazolo[1,5-a]pyridin-3-yl-N-tetrahydro-3-furanylmethylamine

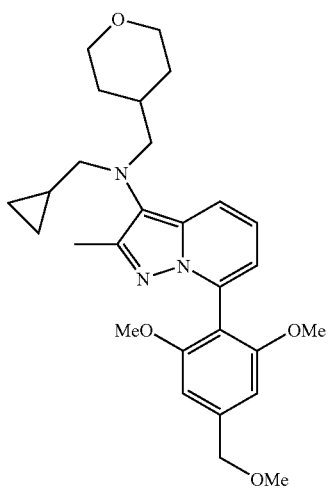

To a solution of N-cyclopropylmethyl-N-7-[2,6-dimethoxy-4-(methoxymethyl)phenyl]-2-methylpyrazolo[1,5-a]pyridin-3-ylamine (40 mg) dissolved in tetrahydrofuran (3 mL) was added tetrahydrofuran-3-carbaldehyde (50% aqueous solution; 0.064 mL), 3 M aqueous sulfuric acid (0.105 mL) and sodium borohydride (8 mg) while cooling with ice, and the reaction mixture was stirred for 1 hour. Water and then saturated aqueous sodium bicarbonate were added to the obtained reaction mixture, extraction was performed with ethyl acetate, and the organic extract was washed with brine. The obtained organic extract was dried over anhydrous magnesium sulfate and filtered, the solvent was evaporated under reduced pressure, the residue was purified by silica gel column chromatography and the title compound (30 mg) was obtained as light yellow crystals from the n-hexane:ethyl acetate (1:1) fraction.

¹H NMR (400 MHz, CDCl₃) δ −0.03-0.03 (m, 2H), 0.33-0.38 (m, 2H), 0.80-0.90 (m, 1H), 1.54-1.68 (m, 1H), 1.85-1.95 (m, 1H), 2.20-2.29 (m, 1H), 2.33 (s, 3H), 2.87-2.90 (m, 2H), 3.06 (dd, J=8.8, 12.0 Hz, 1H), 3.22 (dd, J=6.4, 12.0 Hz, 1H), 3.47 (s, 3H), 3.59-3.70 (m, 2H), 3.71 (s, 6H), 3.72-3.88 (m, 2H), 4.51 (s, 2H), 6.54 (dd, J=1.2, 6.8 Hz, 1H), 6.66 (s, 2H), 7.01 (dd, J=6.8, 8.8 Hz, 1H), 7.41 (dd, J=1.2, 8.8 Hz, 1H).

Similarly to Example 20, the compounds of Example 39 and 40 were obtained.

Example 39

(4-3-[(Cyclopropylamine)(tetrahydro-2H-4-pyranylmethyl)amino]-2-methylpyrazolo[1,5-a]pyridin-7-yl-3,5-dimethoxyphenyl)methanol

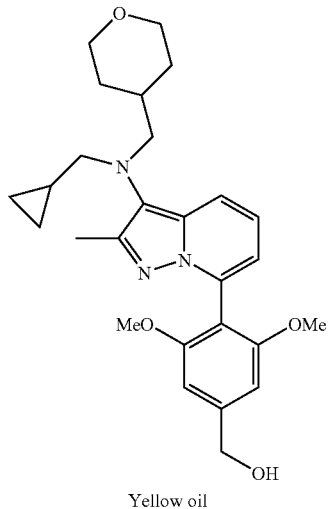

Yellow oil

¹H NMR (400 MHz, CDCl₃) δ −0.04-0.06 (m, 2H), 0.34-0.42 (m, 2H), 0.80-0.94 (m, 1H), 1.23-1.38 (m, 2H), 1.54-1.72 (m, 1H), 1.74-1.84 (m, 2H), 2.38 (s, 3H), 2.47 (br s, 1H), 2.89 (d, J=6.8 Hz, 2H), 3.07 (d, J=7.0 Hz, 2H), 3.34 (dt, J=2.0, 12.0 Hz, 2H), 3.74 (s, 6H), 3.90-4.02 (m, 2H), 4.71 (s, 2H), 6.57 (dd, J=1.4, 6.8 Hz, 1H), 6.71 (s, 2H), 7.05 (dd, J=6.8, 8.8 Hz, 1H), 7.52-7.60 (m, 1H).

Example 40

N-Cyclopropylamine-N-7-[4-(ethoxymethyl)-2,6-dimethoxyphenyl]-2-methylpyrazolo[1,5-a]pyridin-3-yl-N-tetrahydro-2H-4-pyranylmethylamine

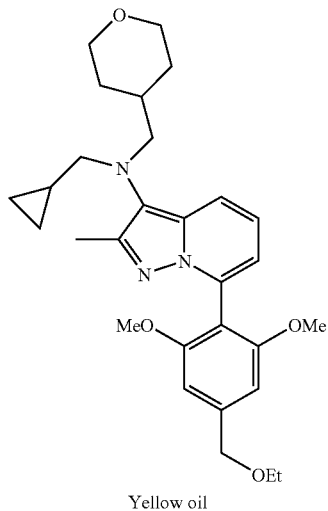

Yellow oil

¹H NMR (400 MHz, CDCl₃) δ −0.03-0.05 (m, 2H), 0.32-0.42 (m, 2H), 0.80-0.94 (m, 1H), 1.34 (t, J=7.2 Hz, 3H), 1.22-1.38 (m, 2H), 1.54-1.70 (m, 1H), 1.74-1.84 (m, 2H), 2.38 (s, 3H), 2.89 (d, J=6.8 Hz, 2H), 3.07 (d, J=7.2 Hz, 2H), 3.34 (dt, J=1.6, 12.0 Hz, 2H), 3.66 (q, J=7.2 Hz, 2H), 3.75 (s, 6H), 3.92-4.02 (m, 2H), 4.59 (s, 2H), 6.57 (dd, J=1.4, 6.8 Hz, 1H), 6.72 (s, 2H), 7.04 (dd, J=6.8, 8.8 Hz, 1H), 7.45 (dd, J=1.4, 8.8 Hz, 1H).

Example 41 tert-Butyl N-[7-[2,6-dimethoxy-4-(methoxymethyl)phenyl]-2-(methoxymethyl)pyrazolo[1,5-a]pyridin-3-yl)carbamate

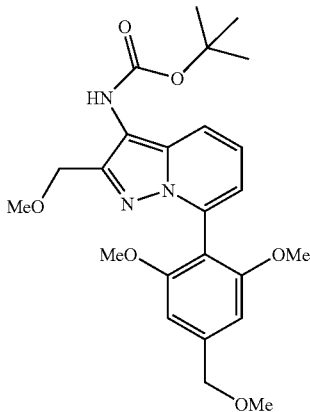

To a solution of tert-butyl N-[7-bromo-2-(methoxymethyl)pyrazolo[1,5-a]pyridin-3-yl]carbamate (300 mg) dissolved in 1,2-dimethoxyethane (10 mL) and water (5 mL) was added 2,6-dimethoxy-4-methoxymethylphenylboric acid (323 mg), tetrakis(triphenylphosphine)palladium(0) (146 mg) and barium hydroxide octahydrate (398 mg), and the reaction mixture was heated and stirred for 2 hours at 80° C. under a nitrogen stream. Water was added to the obtained reaction mixture, the reaction mixture was extracted with ethyl acetate, and the organic extract was washed with brine. The obtained organic extract was dried over anhydrous magnesium sulfate and filtered, and the solvent was evaporated under reduced pressure. The residue was purified by silica gel column chromatography and the title compound (245 mg) was obtained as a light yellow amorphous solid from the n-hexane:ethyl acetate (1:1) fraction.

$^1$H NMR (400 MHz, CDCl$_3$) δ 1.55 (br s, 9H), 3.32 (s, 3H), 3.76 (s, 3H), 3.68 (s, 6H), 4.51 (s, 2H), 4.62 (s, 2H), 6.37-6.46 (m, 1H), 6.65 (s, 2H), 7.13 (dd, J=6.8, 8.8 Hz, 1H), 7.50-7.58 (m, 1H).

Example 42

N-Cyclopropylmethyl-N-[7-[2,6-dimethoxy-4-(methoxymethyl)phenyl]-2-(methoxymethyl)pyrazolo[1,5-a]pyridin-3-yl]amine

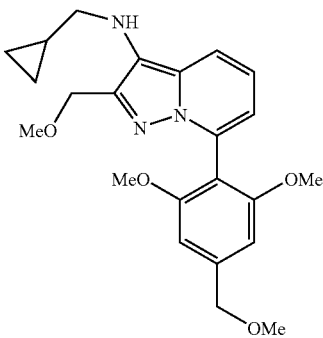

To a solution of tert-butyl N-[7-[2,6-dimethoxy-4-(methoxymethyl)phenyl]-2-(methoxymethyl)pyrazolo[1,5-a]pyridin-3-yl]carbamate (170 mg) dissolved in N,N-dimethylformamide (4 mL) was added sodium hydride (60% in oil; 22 mg) and (bromomethyl)cyclopropane (0.043 mL), and the reaction mixture was stirred for 30 minutes at 40° C. Water was added to the obtained reaction mixture, extraction was performed with ethyl acetate and the organic extract was washed with brine. The obtained organic extract was dried over anhydrous magnesium sulfate and filtered, and the solvent was evaporated under reduced pressure to afford a crude product of tert-butyl N-cyclopropylmethyl-N-[7-[2,6-dimethoxy-4-(methoxymethyl)phenyl]-2-(methoxymethyl)pyrazolo[1,5-a]pyridin-3-yl]carbamate.

The obtained tert-butyl N-cyclopropylmethyl-N-[7-[2,6-dimethoxy-4-(methoxymethyl)phenyl]-2-(methoxymethyl)pyrazolo[1,5-a]pyridin-3-yl]carbamate was dissolved in ethyl acetate (5 mL) without purification, and then 4N hydrochloric acid (ethyl acetate solution; 10 mL) was added thereto and the reaction mixture was stirred for 30 minutes at 40° C. The reaction mixture was neutralized with a 5N aqueous sodium hydroxide solution while cooling with ice, and then the reaction mixture was extracted with ethyl acetate and the organic extract was washed with water and brine. The organic extract was dried over anhydrous magnesium sulfate and filtered, the solvent was evaporated under reduced pressure, the residue was purified by silica gel column chromatography and the title compound (95 mg) was obtained as a yellow oil from the n-hexane:ethyl acetate (2:3) fraction.

$^1$H NMR (400 MHz, CDCl$_3$) δ 0.15-0.20 (m, 2H), 0.48-0.54 (m, 2H), 1.02-1.10 (m, 1H), 1.20-1.32 (m, 2H), 2.35 (s, 3H), 2.88 (d, J=6.8 Hz, 2H), 3.47 (s, 3H), 3.70 (s, 6H), 4.51 (s, 2H), 6.63 (dd, J=1.2, 6.8 Hz, 1H), 6.65 (s, 2H), 6.99 (dd, J=6.8, 8.8 Hz, 1H), 7.36-7.40 (m, 1H).

Example 43

N-Cyclopropylmethyl-N-[7-[2,6-dimethoxy-4-(methoxymethyl)phenyl]-2-(methoxymethyl)pyrazolo[1,5-a]pyridin-3-yl]-N-tetrahydro-2H-4-pyranylmethylamine

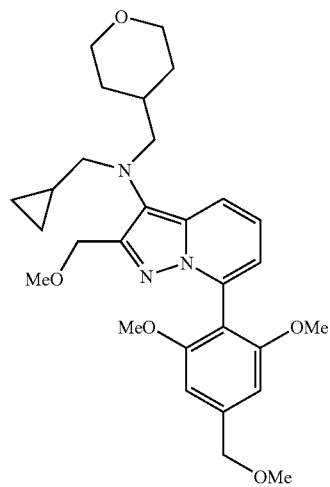

To a solution of N-cyclopropylmethyl-N-[7-[2,6-dimethoxy-4-(methoxymethyl)phenyl]-2-(methoxymethyl)pyrazolo[1,5-a]pyridin-3-yl]amine (80 mg) dissolved in tetrahydrofuran (2 mL) was added tetrahydropyran-4-carbaldehyde (44 mg) and sodium triacetoxyborohydride (82 mg), and the reaction mixture was stirred for 30 minutes at room temperature. Water and saturated aqueous sodium bicarbonate were added to the reaction mixture, extraction was performed with ethyl acetate and the organic extract was washed with brine. The organic extract was dried over anhydrous magnesium sulfate and filtered, the solvent was evaporated under reduced pressure, the residue was purified by silica gel column chromatography and the title compound (63 mg) was obtained as a yellow oil from the n-hexane: ethyl acetate (1:2) fraction.

$^1$H NMR (400 MHz, CDCl$_3$) δ −0.01-0.01 (m, 2H), 0.33-0.37 (m, 2H), 0.78-0.88 (m, 1H), 1.20-1.32 (m, 2H), 1.52-1.65 (m, 1H), 1.72-1.78 (m, 2H), 2.87 (d, J=6.8 Hz, 2H), 3.05 (d, J=6.8 Hz, 2H), 3.26-3.33 (m, 2H), 3.29 (s, 3H), 3.48 (s, 3H), 3.70 (s, 6H), 3.89-3.95 (m, 2H), 4.51 (s, 2H), 4.56 (s, 2H), 6.63 (dd, J=1.2, 6.8 Hz, 1H), 6.65 (s, 2H), 7.03 (dd, J=6.8, 8.8 Hz, 1H), 7.51 (dd, J=1.2, 8.8 Hz, 1H).

Example 44

N-Cyclopropylmethyl-N-[7-[2,6-dimethoxy-4-(methoxymethyl)phenyl]-2-(methoxymethyl)pyrazolo[1,5-a]pyridin-3-yl]-N-tetrahydro-3-furanylmethylamine

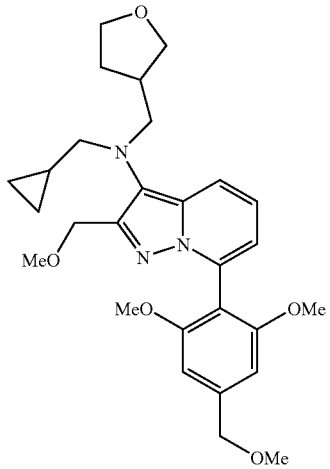

To a solution of N-cyclopropylmethyl-N-[7-[2,6-dimethoxy-4-(methoxymethyl)phenyl]-2-(methoxymethyl)pyrazolo[1,5-a]pyridin-3-yl]amine (15 mg) dissolved in tetrahydrofuran (1 mL) was added tetrahydrofuran-3-carbaldehyde (50% aqueous solution; 0.022 mL), a 3M aqueous sulfuric acid solution (0.036 mL) and sodium borohydride (2.8 mg) while cooling with ice and the reaction mixture was stirred for 1 hour at the same temperature. Water and then saturated aqueous sodium bicarbonate were added to the obtained reaction mixture, extraction was performed with ethyl acetate, the organic extract was washed with brine, dried over anhydrous magnesium sulfate and filtered, and the solvent was evaporated under reduced pressure. The residue was purified by silica gel column chromatography and the title compound (4.8 mg) was obtained as light yellow crystals from the n-hexane:ethyl acetate (1:2) fraction.

$^1$H NMR (400 MHz, CDCl$_3$) δ 0.00-0.06 (m, 2H), 0.32-0.40 (m, 2H), 0.80-0.90 (m, 1H), 1.55-1.68 (m, 1H), 1.86-1.95 (m, 1H), 2.21-2.32 (m, 1H), 2.88-2.92 (m, 2H), 3.08 (dd, J=8.8, 12.0 Hz, 1H), 3.23 (dd, J=6.8, 12.0 Hz, 1H), 3.30 (s, 3H), 3.48 (s, 3H), 3.60-3.68 (m, 2H), 3.69 (s, 6H), 3.72-3.84 (m, 2H), 4.51 (s, 2H), 4.55 (s, 2H), 6.54 (dd, J=1.2, 6.8 Hz, 1H), 6.66 (s, 2H), 7.01 (dd, J=6.8, 8.8 Hz, 1H), 7.41 (dd, J=1.2, 8.8 Hz, 1H).

Similarly to Example 20, the compound of Example 45 and 46 were obtained.

Example 45

4-[3-[(Cyclopropylamine)(tetrahydro-2H-4-pyranylmethyl)amino]-2-(methoxymethyl)pyrazolo[1,5-a]pyridin-7-yl]-3,5-dimethoxyphenylmethanol

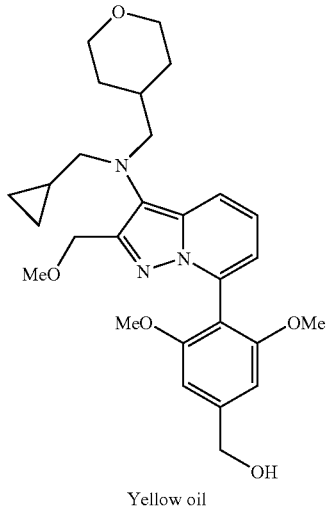

Yellow oil $^1$H NMR (400 MHz, CDCl$_3$) δ −0.04-0.04 (m, 2H), 0.30-0.40 (m, 2H), 0.78-0.92 (m, 1H), 1.20-1.34 (m, 2H), 1.53-1.70 (m, 1H), 1.71-1.80 (m, 2H), 2.20 (br s, 1H), 2.88 (d, J=6.8 Hz, 2H), 3.05 (d, J=7.2 Hz, 2H), 3.29 (s, 3H), 3.24-3.38 (m, 2H), 3.70 (s, 6H), 3.88-3.98 (m, 2H), 4.57 (s, 2H), 4.71 (s, 2H), 6.63 (dd, J=1.4, 6.8 Hz, 1H), 6.68 (s, 2H), 7.05 (dd, J=6.8, 8.8 Hz, 1H), 7.49-7.57 (m, 1H).

Example 46

N-Cyclopropylamine-N-[7-[4-(ethoxymethyl)-2,6-dimethoxyphenyl]-2-(methoxymethyl)pyrazolo[1,5-a]pyridin-3-yl]-N-tetrahydro-2H-4-pyranylmethylamine

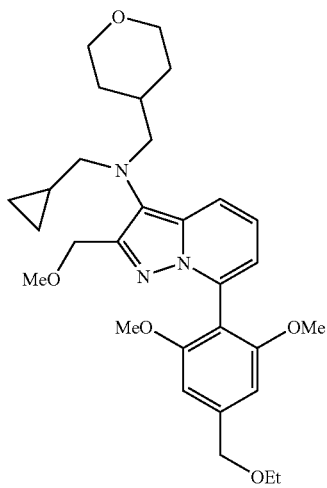

Yellow oil $^1$H NMR (400 MHz, CDCl$_3$) δ −0.04-0.04 (m, 2H), 0.30-0.40 (m, 2H), 0.78-0.92 (m, 1H), 1.31 (t, J=6.8 Hz, 3H), 1.20-1.36 (m, 2H), 1.54-1.68 (m, 1H), 1.70-1.81 (m, 2H), 2.89 (d, J=6.8 Hz, 2H), 3.06 (d, J=6.8 Hz, 2H), 3.30 (s, 3H), 3.26-3.36 (m, 2H), 3.64 (q, J=6.8 Hz, 2H), 3.71 (s, 6H), 3.89-3.98 (m, 2H), 4.56 (s, 2H), 4.57 (s, 2H), 6.64 (dd, J=1.6, 6.8 Hz, 1H), 6.68 (s, 2H), 7.05 (dd, J=6.8, 8.8 Hz, 1H), 7.52 (dd, J=1.6, 8.8 Hz, 1H).

Example 47

N-Cyclopropylmethyl-N-7-[2,6-dimethoxy-4-(methoxymethyl)phenyl]-2-methoxypyrazolo[1,5-a]pyridin-3-yl-N-tetrahydro-2H-4-pyranylmethylamine

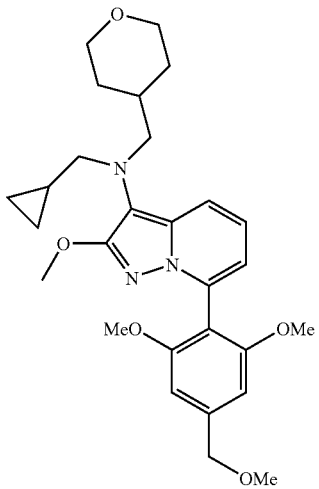

To a solution of N-(7-bromo-2-methoxypyrazolo[1,5-a]pyridin-3-yl)-N-cyclopropylmethyl-N-tetrahydro-2H-4-pyranylmethylamine (48 mg) dissolved in a mixture of 1,2-dimethoxyethane (2 mL) and water (1 mL) was added 2,6-dimethoxy-4-(methoxymethyl)phenylboric acid (36 mg), tetrakis(triphenylphosphine)palladium(0) (28 mg) and barium hydroxide octahydrate (58 mg), and the reaction mixture was heated and stirred for 2 hours at 85° C. Water and ethyl acetate were added to the obtained reaction mixture, the reaction mixture was filtered through celite to remove insoluble residue, and then the filtrate was extracted with ethyl acetate. The obtained organic extract was washed with brine, dried over anhydrous magnesium sulfate and filtered, and the solvent was evaporated under reduced pressure. The obtained residue was purified by silica gel column chromatography and the title compound (40 mg) was obtained as light yellow crystals from the n-hexane:ethyl acetate (2:1) fraction.

$^1$H NMR (400 MHz, CDCl$_3$) δ −0.02-0.04 (m, 2H), 0.30-0.36 (m, 2H), 0.80-0.92 (m, 1H), 1.24-1.36 (m, 2H), 1.52-1.64 (m, 1H), 1.74-1.82 (m, 2H), 2.84 (d, J=6.8 Hz, 2H), 2.97 (d, J=6.8 Hz, 2H), 3.32 (td, J=2.0, 11.6 Hz, 2H), 3.51 (s, 3H), 3.76 (s, 6H), 3.87 (s, 3H), 3.90-3.98 (m, 2H), 4.55 (s, 2H), 6.51 (dd, J=1.6, 6.8 Hz, 1H), 6.69 (s, 2H), 7.04 (dd, J=7.2, 8.8 Hz, 1H), 7.33 (dd, J=1.6, 8.8 Hz, 1H).

Similarly to Example 47, the compounds of Example 48 to 51 were synthesized.

Example 48

N-Cyclopropylmethyl-N-7-[2,6-dimethoxy-4-(1-methoxyethyl)phenyl]-2-methoxypyrazolo[1,5-a]pyridin-3-yl-N-tetrahydro-2H-4-pyranylmethylamine

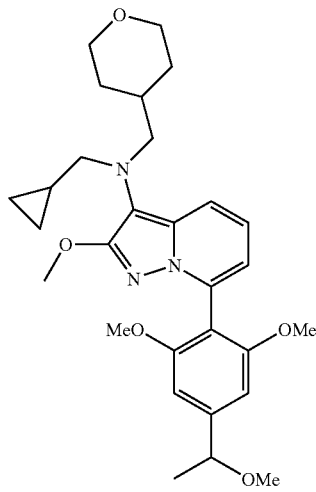

Light yellow crystals $^1$H NMR (400 MHz, CDCl$_3$) δ −0.02-0.04 (m, 2H), 0.30-0.38 (m, 2H), 0.80-0.92 (m, 1H), 1.22-1.34 (m, 2H), 1.55 (d, J=1.6 Hz, 3H), 1.56-1.68 (m, 1H), 1.72-1.82 (m, 2H), 2.84 (d, J=6.8 Hz, 2H), 2.97 (d, J=7.2 Hz, 2H), 3.26-3.34 (m, 2H), 3.37 (s, 3H), 3.77 (s, 6H), 3.89 (s, 3H), 3.90-3.98 (m, 2H), 4.37 (q, J=6.4 Hz, 1H), 6.53 (dd, J=1.2, 7.2 Hz, 1H), 6.66 (d, J=3.2 Hz, 2H), 7.04 (dd, J=7.2, 8.8 Hz, 1H), 7.33 (dd, J=1.6, 8.8 Hz, 1H).

Example 49

(4-3-[(Cyclopropylmethyl)(tetrahydro-2H-4-pyranylmethyl)amino]-2-methoxypyrazolo[1,5-a]pyridin-7-yl-3,5-dimethoxyphenyl)methanol Yellow amorphous solid $^1$H NMR (400 MHz, CDCl$_3$) δ −0.02-0.06 (m, 2H), 0.30-0.38 (m, 2H), 0.80-0.93 (m, 1H), 1.23-1.38 (m, 2H), 1.53-1.67 (m, 1H), 1.74-1.88 (m, 2H), 2.84 (d, J=6.6 Hz, 2H), 2.98 (d, J=7.0 Hz, 2H), 3.33 (dt, J=1.7, 12.0 Hz, 2H), 3.77 (s, 6H), 3.88 (s, 3H), 3.91-4.00 (m, 2H), 4.81 (br d, J=4.6 Hz, 2H), 6.50-6.55 (m, 1H), 6.74 (s, 2H), 7.02-7.09 (m, 1H), 7.32-7.38 (m, 1H).

Example 50

N-Cyclopropylmethyl-N-7-[4-(ethoxymethyl)-2,6-dimethoxyphenyl]-2-methoxypyrazolo[1,5-a]pyridin-3-yl-N-tetrahydro-2H-4-pyranylmethylamine

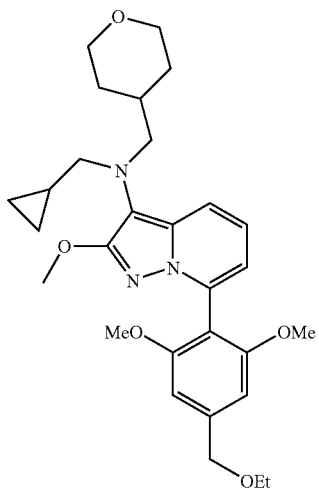

Yellow oil $^1$H NMR (400 MHz, CDCl$_3$) δ −0.02-0.07 (m, 2H), 0.30-0.39 (m, 2H), 0.82-0.95 (m, 1H), 1.36 (t, J=7.0 Hz, 3H), 1.25-1.39 (m, 2H), 1.55-1.68 (m, 1H), 1.75-1.84 (m, 2H), 2.85 (d, J=6.8 Hz, 2H), 2.99 (d, J=7.0 Hz, 2H), 3.34 (dt, J=1.8, 12.0 Hz, 2H), 3.69 (q, J=7.0 Hz, 2H), 3.78 (s, 6H), 3.89 (s, 3H), 3.92-4.00 (m, 2H), 4.62 (s, 2H), 6.52 (dd, J=1.4, 6.9 Hz, 1H), 6.72 (s, 2H), 7.06 (dd, J=6.9, 8.9 Hz, 1H), 7.35 (dd, J=1.4, 8.9 Hz, 1H).

Example 51

N-Cyclopropylmethyl-N-7-[2,6-dimethoxy-4-(methoxymethyl)phenyl]-2-methoxypyrazolo[1,5-a]pyridin-3-yl-N-tetrahydro-3-furanylmethylamine

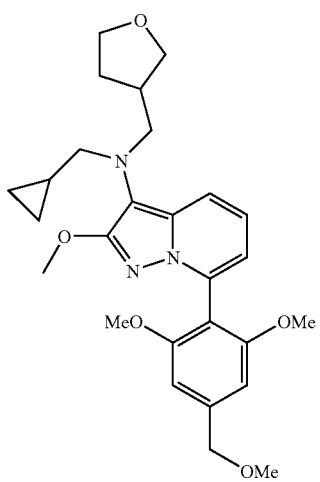

Light yellow crystals $^1$H NMR (400 MHz, CDCl$_3$) δ −0.02-0.04 (m, 2H), 0.28-0.34 (m, 2H), 0.78-0.86 (m, 1H), 1.60-1.68 (m, 1H), 1.84-1.94 (m, 1H), 2.20-2.30 (m, 1H), 2.83 (d, J=6.8 Hz, 2H), 2.92-3.00 (m, 1H), 3.10-3.14 (m, 1H), 3.48 (s, 3H), 3.52-3.68 (m, 2H), 3.73 (s, 6H), 3.74-3.82 (m, 2H), 3.84 (s, 3H), 4.52 (s, 2H), 6.48 (dd, J=1.2, 7.2 Hz, 1H), 6.65 (s, 2H), 7.02 (dd, J=7.2, 8.8 Hz, 1H), 7.29 (dd, J=1.2, 8.8 Hz, 1H)

Example 52 tert-Butyl N-7-[2,6-dimethoxy-4-(methoxymethyl)phenyl]-2-methoxypyrazolo[1,5-a]pyridin-3-ylcarbamate

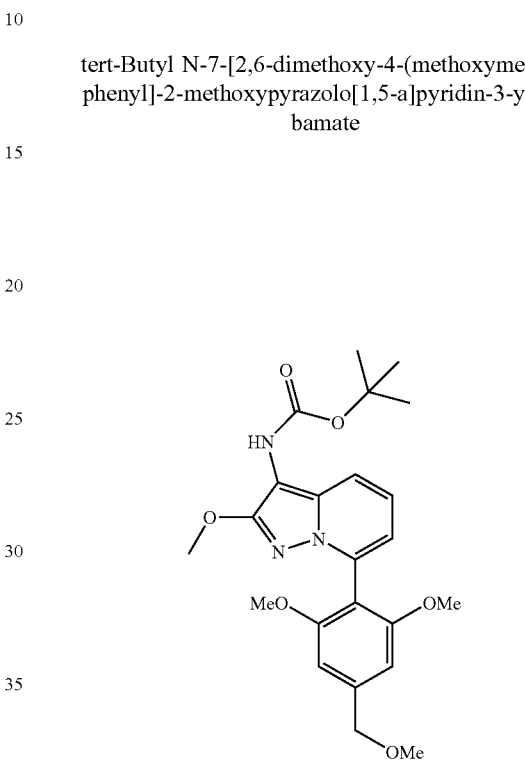

To a solution of tert-butyl N-(7-bromo-2-methoxypyrazolo[1,5-a]pyridin-3-yl)carbamate (200 mg) dissolved in 1,2-dimethoxyethane (12 mL) and water (6 mL) was added 2,6-dimethoxy-4-(methoxymethyl)phenylboric acid (197 mg), tetrakis(triphenylphosphine)palladium(0) (101 mg) and barium hydroxide octahydrate (274 mg), and the reaction mixture was heated and stirred for 4 hours at 80° C. under a nitrogen stream. Ethyl acetate was added to the obtained reaction mixture, and after filtering out the insoluble residue, the reaction mixture was extracted with ethyl acetate, the organic extract was washed with brine, dried over anhydrous magnesium sulfate and filtered, and the solvent was evaporated under reduced pressure. The residue was purified by silica gel column chromatography and the title compound (150 mg) was obtained as a light yellow oil from the n-hexane:ethyl acetate (1:1) fraction.

$^1$H NMR (400 MHz, CDCl$_3$) δ 1.52 (br s, 9H), 3.48 (s, 3H), 3.70 (s, 6H), 3.87 (s, 3H), 4.51 (s, 2H), 5.82 (br s, 1H), 6.53 (d, J=6.8 Hz, 1H), 6.64 (s, 2H), 7.10 (dd, J=6.8, 8.8 Hz, 1H), 7.27 (d, J=8.8 Hz, 1H).

Example 53

N-Cyclobutylmethyl-N-7-[2,6-dimethoxy-4-(methoxymethyl)phenyl]-2-methoxypyrazolo[1,5-a]pyridin-3-yl-N-tetrahydro-2H-4-pyranylmethylamine

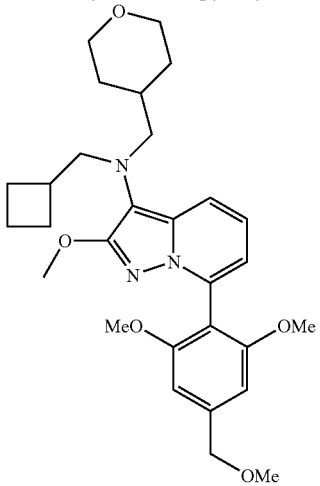

To a solution of tert-butyl N-7-[2,6-dimethoxy-4-(methoxymethyl)phenyl]-2-methoxypyrazolo[1,5-a]pyridin-3-yl-carbamate (75 mg) dissolved in N,N-dimethylformamide (0.6 mL) was added sodium hydride (60% in oil; 10 mg) and (bromomethyl)cyclobutane (0.022 mL), and the reaction mixture was stirred for 1 hour at room temperature. Water was added to the obtained reaction mixture, extraction was performed with ethyl acetate and the organic extract was washed with brine. The organic extract was dried over anhydrous magnesium sulfate and filtered, and the solvent was evaporated under reduced pressure to afford a crude product of tert-butyl N-cyclobutylmethyl-N-7-[2,6-dimethoxy-4-(methoxymethyl)phenyl]-2-methoxypyrazolo[1,5-a]pyridin-3-ylcarbamate.

To the obtained crude product of tert-butyl N-cyclobutyl-methyl-N-7-[2,6-dimethoxy-4-(methoxymethyl)phenyl]-2-methoxypyrazolo[1,5-a]pyridin-3-ylcarbamate without further purification was added 4N hydrochloric acid (ethyl acetate solution; 1 mL), and the reaction mixture was stirred for 1 hour at 40° C. The obtained reaction mixture was neutralized with a 2N aqueous sodium hydroxide solution while cooling with ice, and then extraction was performed with ethyl acetate and the organic extract was washed with brine. The organic extract was dried over anhydrous magnesium sulfate and filtered, the residue was purified by silica gel column chromatography, and N-cyclobutylmethyl-N-7-[2,6-dimethoxy-4-(methoxymethyl)phenyl]-2-methoxypyrazolo[1,5-a]pyridin-3-ylamine (51 mg) was obtained as a yellow oil from the n-hexane:ethyl acetate (1:1) fraction.

To a solution of the obtained N-cyclobutylmethyl-N-7-[2,6-dimethoxy-4-(methoxymethyl)phenyl]-2-methoxypyrazolo[1,5-a]pyridin-3-ylamine dissolved in tetrahydrofuran (0.6 mL) was added tetrahydropyran-4-carbaldehyde (34 mg) and sodium triacetoxyborohydride (38 mg), and the reaction mixture was stirred for 2 hours at room temperature. Saturated aqueous sodium bicarbonate was added to the obtained reaction mixture, extraction was performed with ethyl acetate and the organic extract was washed with brine. The organic extract was dried over anhydrous magnesium sulfate and filtered, the solvent was evaporated under reduced pressure, the residue was purified by silica gel column chromatography and the title compound (52 mg) was obtained as a yellow oil from the n-hexane:ethyl acetate (3:2) fraction.

$^1$H NMR (400 MHz, CDCl$_3$) δ 1.17-1.30 (m, 2H), 1.48-1.63 (m, 3H), 1.69-1.89 (m, 6H), 2.26-2.39 (m, 1H), 2.82-2.87 (m, 2H), 2.93-2.98 (m, 2H), 3.24-3.34 (m, 2H), 3.49 (s, 3H), 3.73 (s, 6H), 3.85 (s, 3H), 3.88-3.96 (m, 2H), 4.53 (s, 2H), 6.48 (dd, J=1.3, 6.8 Hz, 1H), 6.66 (s, 2H), 7.02 (dd, J=6.8, 8.8 Hz, 1H), 7.24 (dd, J=1.3, 8.8 Hz, 1H).

Similarly to Example 53, the compounds of Example 54 to 56 were synthesized.

Example 54

N-Butyl-N-7-[2,6-dimethoxy-4-(methoxymethyl)phenyl]-2-methoxypyrazolo[1,5-a]pyridin-3-yl-N-tetrahydro-2H-4-pyranylmethylamine

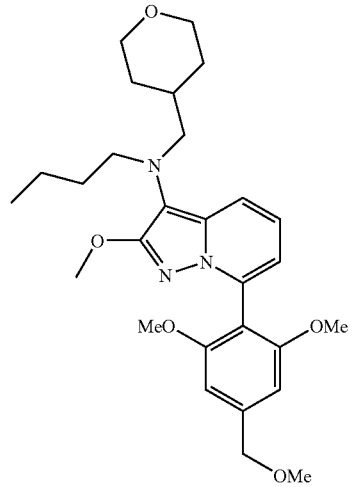

Yellow oil $^1$H NMR (400 MHz, CDCl$_3$) δ 0.81-0.89 (m, 3H), 1.18-1.40 (m, 6H), 1.48-1.60 (m, 1H), 1.70-1.78 (m, 2H), 2.83-2.98 (m, 4H), 3.24-3.34 (m, 2H), 3.49 (s, 3H), 3.74 (s, 6H), 3.85 (s, 3H), 3.88-3.97 (m, 2H), 4.53 (s, 2H), 6.49 (dd, J=1.3, 6.8 Hz, 1H), 6.67 (s, 2H), 7.02 (dd, J=6.8, 8.8 Hz, 1H), 7.26 (dd, J=1.3, 8.8 Hz, 1H).

Example 55

N-7-[2,6-Dimethoxy-4-(methoxymethyl)phenyl]-2-methoxypyrazolo[1,5-a]pyridin-3-yl-N-propyl-N-tetrahydro-2H-4-pyranylmethylamine

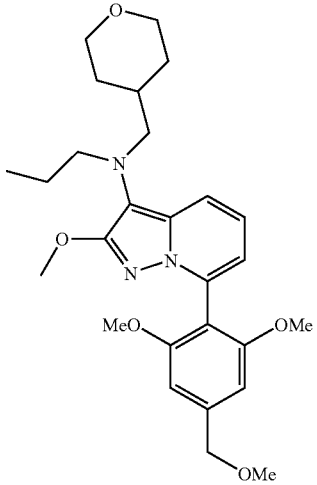

Light yellow amorphous solid $^1$H NMR (400 MHz, CDCl$_3$) δ 0.87 (t, J=7.6 Hz, 3H), 1.20-1.31 (m, 2H), 1.33-1.42 (m, 2H), 1.48-1.62 (m, 1H), 1.71-1.78 (m, 2H), 2.87 (d, J=7.2 Hz, 2H), 2.90 (d, J=7.2 Hz, 2H), 3.25-3.34 (m, 2H), 3.48 (s, 3H), 3.73 (s, 6H), 3.84 (s, 3H), 3.88-3.95 (m, 2H), 4.52 (s, 2H), 6.47 (dd, J=1.2, 6.8 Hz, 1H), 6.66 (s, 2H), 7.00 (dd, J=6.8, 8.8 Hz, 1H), 7.25 (dd, J=1.2, 8.8 Hz, 1H).

Example 56

N-7-[2,6-Dimethoxy-4-(methoxymethyl)phenyl]-2-methoxypyrazolo[1,5-a]pyridin-3-yl-N-isobutyl-N-tetrahydro-2H-4-pyranylmethylamine

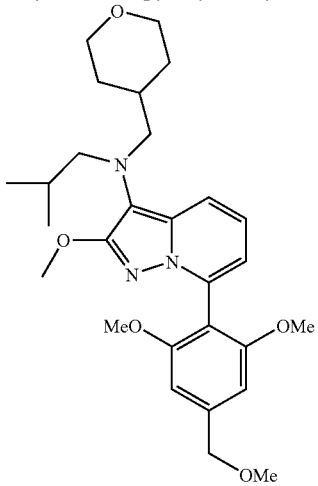

Light yellow amorphous solid $^1$H NMR (400 MHz, CDCl$_3$) δ 0.90 (d, J=6.4 Hz, 6H), 1.19-1.30 (m, 2H), 1.48-1.60 (m, 2H), 1.74-1.81 (m, 2H), 2.72 (d, J=7.2 Hz, 2H), 2.82 (d, J=7.2 Hz, 2H), 3.26-3.34 (m, 2H), 3.48 (s, 3H), 3.73 (s, 6H), 3.84 (s, 3H), 3.89-3.95 (m, 2H), 4.52 (s, 2H), 6.47 (dd, J=1.2, 6.8 Hz, 1H), 6.66 (s, 2H), 7.00 (dd, J=6.8, 8.8 Hz, 1H), 7.26 (dd, J=1.2, 8.8 Hz, 1H).

Similarly to Example 18, the compound of Example 57 was synthesized.

Example 57

1-(4-3-[(Cyclopropylmethyl)(tetrahydro-2H-4-pyranylmethyl)amino]-2-methoxypyrazolo[1,5-a]pyridin-7-yl-3,5-dimethoxyphenyl)-1-ethanol

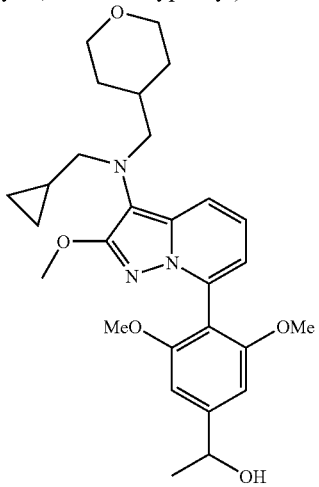

Light yellow amorphous solid $^1$H NMR (400 MHz, CDCl$_3$) δ −0.06-0.01 (m, 2H), 0.27-0.34 (m, 2H), 0.78-0.89 (m, 1H), 1.20-1.34 (m, 2H), 1.49-1.63 (m, 4H), 1.71-1.80 (m, 2H), 2.78-2.84 (m, 2H), 2.91-2.99 (m, 2H), 3.24-3.35 (m, 2H), 3.74 (s, 3H), 3.75 (s, 3H), 3.86 (s, 3H), 3.88-3.97 (m, 2H), 4.93-5.01 (m, 1H), 6.49 (dd, J=1.3, 6.8 Hz, 1H), 6.68 (s, 1H), 6.74 (s, 1H), 7.02 (dd, J=6.8, 8.8 Hz, 1H), 7.31 (dd, J=1.3, 8.8 Hz, 1H).

Similarly to Example 47, the compound of Example 58 was synthesized.

Example 58

N-Cyclopropylmethyl-N-7-[2,6-dimethoxy-4-(methoxymethyl)phenyl]-2-ethoxypyrazolo[1,5-a]pyridin-3-yl-N-tetrahydro-2H-4-pyranylmethylamine

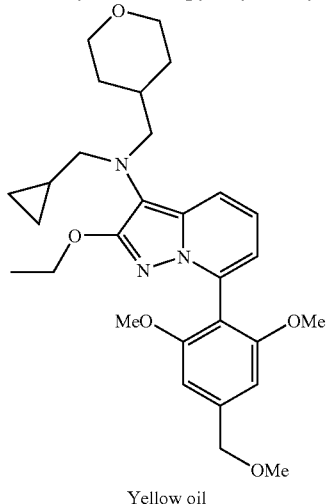

Yellow oil $^1$H NMR (400 MHz, CDCl$_3$) δ −0.04-0.02 (m, 2H), 0.28-0.31 (m, 2H), 0.78-0.88 (m, 1H), 1.20-1.32 (m, 5H), 1.50-1.60 (m, 1H), 1.70-1.78 (m, 2H), 2.81 (d, J=6.4 Hz, 2H), 2.95 (d, J=6.8 Hz, 2H), 3.29 (dt, J=2.0, 11.6 Hz, 2H), 3.48 (s, 3H), 3.72 (s, 6H), 3.89-3.93 (m, 2H), 4.21 (q, J=7.2 Hz, 2H), 4.52 (s, 2H), 6.47 (dd, J=1.2, 6.8 Hz, 1H), 6.66 (s, 2H), 7.00 (dd, J=7.2, 8.8 Hz, 1H), 7.30 (dd, J=1.2, 8.8 Hz, 1H).

Example 59

N-Cyclopropylmethyl-N-[7-[2,6-dimethoxy-4-(methoxymethyl)phenyl]-2-(methylsulfanyl)pyrazolo[1,5-a]pyridin-3-yl]-N-tetrahydro-2H-4-pyranylmethylamine

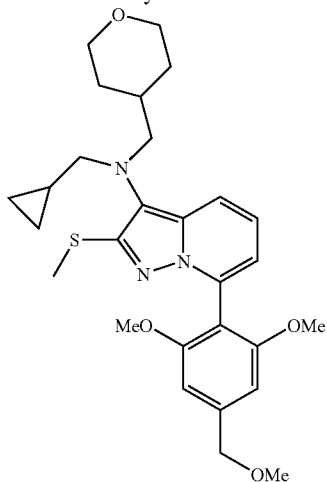

To a solution of N-cyclopropylmethyl-N-[7-iodo-2-(methylsulfanyl)pyrazolo[1,5-a]pyridin-3-yl]-N-tetrahydro-2H-4-pyranylmethylamine (50 mg) dissolved in a mixture of 1,2-dimethoxyethane (2 mL) and water (1 mL) was added 2,6-dimethoxy-4-(methoxymethyl)phenylboric acid (50 mg), tetrakis(triphenylphosphine)palladium(0) (40 mg) and barium hydroxide octahydrate (56 mg), and the reaction mixture was heated and stirred for 3 hours at 80° C. Water and ethyl acetate were added to the obtained reaction mixture, insoluble residue was filtered out with celite, and the filtrate was extracted with ethyl acetate. The organic extracts were combined and washed with brine, dried over anhydrous magnesium sulfate and filtered, and the solvent was evaporated under reduced pressure. The obtained residue was purified by silica gel column chromatography and then by column chromatography using NH Silica (Fuji Silysia) to afford the title compound (36 mg) as a yellow oil.

$^1$H NMR (400 MHz, CDCl$_3$) δ −0.02-0.04 (m, 2H), 0.30-0.38 (m, 2H), 0.82-0.92 (m, 1H), 1.22-1.34 (m, 2H), 1.52-1.64 (m, 1H), 1.76-1.82 (m, 2H), 2.44 (s, 3H), 2.90 (d, J=6.8 Hz, 2H), 3.06 (d, J=7.2 Hz, 2H), 3.32 (td, J=2.0, 12.0 Hz, 2H), 3.50 (s, 3H), 3.74 (s, 6H), 3.90-3.98 (m, 2H), 4.54 (s, 2H), 6.59 (dd, J=1.6, 7.2 Hz, 1H), 6.67 (s, 2H), 7.05 (dd, J=7.2, 8.8 Hz, 1H), 7.41 (dd, J=1.6, 8.8 Hz, 1H).

Similarly to Example 59, the compound of Example 60 was synthesized.

Example 60

N-Cyclopropylmethyl-N-[7-[2,6-dimethoxy-4-(methoxymethyl)phenyl]-2-(methylsulfanyl)pyrazolo[1,5-a]pyridin-3-yl]-N-tetrahydro-3-furanylmethylamine

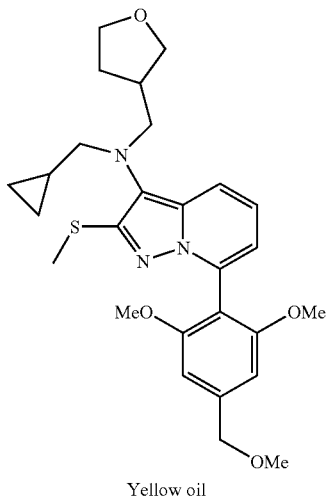

Yellow oil $^1$H NMR (400 MHz, CDCl$_3$) δ −0.02-0.04 (m, 2H), 0.28-0.38 (m, 2H), 0.80-0.90 (m, 1H), 1.58-1.68 (m, 1H), 1.88-1.96 (m, 1H), 2.20-2.30 (m, 1H), 2.42 (s, 3H), 2.88-2.92 (m, 2H), 3.02-3.10 (m, 1H), 3.20-3.24 (m, 1H), 3.47 (s, 3H), 3.58-3.82 (m, 4H), 3.71 (s, 6H), 4.52 (s, 2H), 6.57 (dd, J=1.6, 7.2 Hz, 1H), 6.64 (s, 2H), 7.03 (dd, J=6.8, 8.8 Hz, 1H), 7.38 (dd, J=1.6, 8.8 Hz, 1H).

Production Example 1X

2-Ethyl-3-iodopyrazolo[1,5-a]pyridine

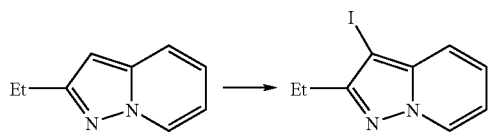

N-Chlorosuccinimide (411 g, 3.08 mol) was gradually added to a mixture of 2-ethylpyrazolo[1,5-a]pyridine (360 g, 2.46 mol), ethyl acetate (3600 mL), water (1800 mL) and sodium iodide (480 g, 3.20 mol, 1.3 equivalents) over a period of 30 minutes while cooling with ice, and then the reaction mixture was stirred for 2 hours and 20 minutes at room temperature. After the reaction, water and ethyl acetate were added to the reaction mixture and extraction was performed with ethyl acetate. The organic extract was washed twice with 10% aqueous sodium thiosulfate, and then concentrated. Hexane was added to the residue, the mixture was heated to dissolution and the resulting solution was filtered to remove insoluble residue. After then washing the hexane solution with water, the hexane layer was concentrated, the residue was dissolved in ethyl acetate and the solvent was evaporated to afford 663 g of the title compound (98.9% yield).

$^1$H NMR (400 MHz, CDCl$_3$) δ 1.35 (t, J=7.7 Hz, 3H), 2.84 (q, J=7.7 Hz, 2H), 6.72 (ddd, J=6.8, 6.8, 1.3 Hz, 1H), 7.15 (ddd, J=9.0, 6.8, 1.1 Hz, 1H), 7.37 (ddd, J=9.0, 1.3 Hz, 1.3, 1H), 8.36 (ddd, J=6.8, 1.1, 1.1 Hz, 1H).

Production Example 2X

Tetrahydro-2H-4-pyrancarboxamide

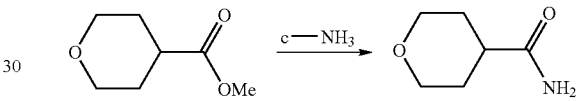

Concentrated aqueous ammonia (50 mL) was added to methyl tetrahydro-2H-pyran-4-carboxylate (50 g, 347 mmol) and the reaction mixture was stirred for 43.5 hours at room temperature. The reaction mixture was then cooled in an ice water bath, after which the precipitate was filtered out and dried under reduced pressure at 40° C. to afford 33.4 g of the title compound (74.6% yield).

$^1$H NMR (400 MHz, DMSO-d$_6$) δ 1.45-1.62 (m, 4H), 2.28 (tt, J=11.1, 4.4 Hz, 1H), 3.26 (ddd, J=11.4, 11.4, 2.7 Hz, 2H), 3.82 (br d, J=11.4 Hz, 2H), 6.74 (br s, 1H), 7.21 (br s, 1H).

Production Example 3X

N4-(2-Ethylpyrazolo[1,5-a]pyridin-3-yl)tetrahydro-2H-4-pyrancarboxamide

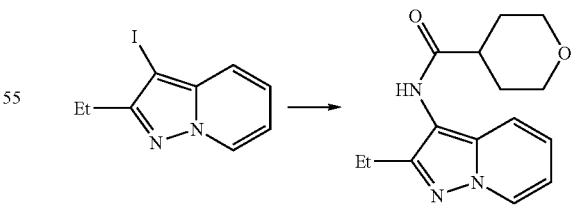

A mixture of 2-ethyl-3-iodopyrazolo[1,5-a]pyridine (350 g, 1.29 mol), tetrahydro-2H-4-pyrancarboxamide (249 g, 1.93 mol), copper iodide (49.0 g, 258 mmol), tripotassium phosphate (hydrate) (546 g, 2.57 mol), 1,2-cyclohexanediamine (mixture of cis and trans) (58.7 g, 514 mmol) and xylene (3500 mL) was stirred while heating at an external temperature of 120° C. (oil bath). The reaction mixture was heated and stirred for 6 hours, and then heating was terminated and upon reaching an internal temperature of 61.5° C., hot water (58° C., 3500 mL) was added to the reaction mixture and stirring was continued overnight. After adding 28% aqueous ammonia (1050 mL) to the reaction mixture and stirring for 1 hour, the precipitate was filtered out and washed with water (1750 mL) and ethyl acetate (1050 mL) and then dried under aeration at 60° C. overnight to afford 280 g of the title compound (major conformer:minor conformer=6:1) (79.6% yield)

Major Conformer $^1$H NMR (400 MHz, CDCl$_3$) δ 1.33 (t, J=7.7 Hz, 3H), 1.88-2.05 (m, 4H), 2.57-2.67 (m, 1H), 2.75 (q, J=7.7 Hz, 2H), 3.50 (ddd, J=11.4, 11.4, 2.9 Hz, 2H), 4.09 (ddd, J=11.4, 4.0, 2.6 Hz, 2H), 6.68 (ddd, J=6.8, 6.8, 1.3 Hz, 1H), 6.82 (br s, 1H), 7.07 (ddd, J=9.0, 6.8, 1.3 Hz, 1H), 7.29 (br d, J=9.0 Hz, 1H), 8.30 (d, J=6.8 Hz, 1H)

Minor Conformer $^1$H NMR (400 MHz, CDCl$_3$) δ 1.34 (t, J=7.7 Hz, 3H), 1.40-1.50 (m, 2H), 1.88-2.05 (m, 2H), 2.37-2.48 (m, 1H), 2.78 (q, J=7.7 Hz, 2H), 3.14 (ddd, J=11.9, 11.9, 1.8 Hz, 2H), 3.84-3.92 (m, 2H), 6.56 (br s, 1H), 6.80 (ddd, J=6.8, 6.8, 1.3 Hz, 1H), 7.20 (br dd, J=9.0, 6.8 Hz, 1H), 7.34 (br d, J=9.0 Hz, 1H), 8.39 (d, J=6.8 Hz, 1H)

Production Example 4X

N4-Cyclopropylmethyl-N4-(2-ethylpyrazolo[1,5-a]pyridin-3-yl)tetrahydro-2H-4-pyrancarboxamide

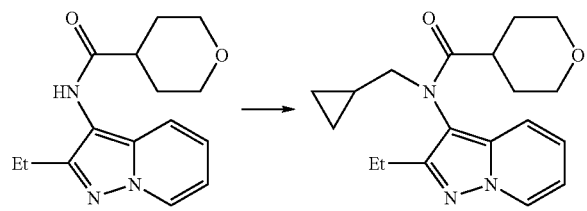

A mixture of N4-(2-ethylpyrazolo[1,5-a]pyridin-3-yl)tetrahydro-2H-4-pyrancarboxamide (272 g, 915 mmol), potassium tert-butoxide (144 g, 1.28 mol) and 1,2-dimethoxyethane (1750 mL) was heated and stirred at an external temperature of 40° C. (Bromomethyl)cyclopropane (161 g, 1.19 mol) was then added dropwise to the reaction mixture keeping the internal temperature below 50° C. After heating and stirring for 4 hours, water (1250 mL) and toluene (3750 mL) were added to the reaction mixture. The aqueous layer was removed, and then the organic extract was washed with 10% brine (1250 mL) and water (1250 mL×2 times) in that order, and concentrated under reduced pressure to afford 277 g of the title compound as a brown oil (92.6% yield).

$^1$H NMR (400 MHz, CDCl$_3$) δ 0.03-0.11 (m, 1H), 0.14-0.22 (m, 1H), 0.32-0.46 (m, 2H), 0.85-0.98 (m, 1H), 1.36 (t, J=7.6 Hz, 3H), 1.29-1.40 (m, 1H), 1.40-1.50 (m, 1H), 1.85 (ddd, J=16.3, 11.9, 4.4 Hz, 1H), 1.97 (ddd, J=16.5, 11.9, 4.6 Hz, 1H), 2.41 (tt, J=11.5, 3.8 Hz, 1H), 2.66-2.84 (m, 2H), 3.03 (ddd, J=11.9, 11.9, 2.2 Hz, 1H), 3.15 (ddd, J=11.9, 11.9, 2.2 Hz, 1H), 3.31 (dd, J=13.7, 7.3 Hz, 1H), 3.79 (dd, J=13.7, 7.3 Hz, 1H), 3.76-3.86 (m, 1H), 3.91 (ddd, J=11.9, 4.4, 2.0 Hz, 1H), 6.79 (ddd, J=6.8, 6.8, 1.4 Hz, 1H), 7.17 (br dd, J=8.8, 6.8 Hz, 1H), 7.33 (br d, J=8.8 Hz, 1H), 8.40 (d, J=6.8 Hz, 1H).

Production Example 5X

N-Cyclopropylmethyl-N-(2-ethylpyrazolo[1,5-a]pyridin-3-yl)-N-tetrahydro-2H-4-pyranylmethylamine

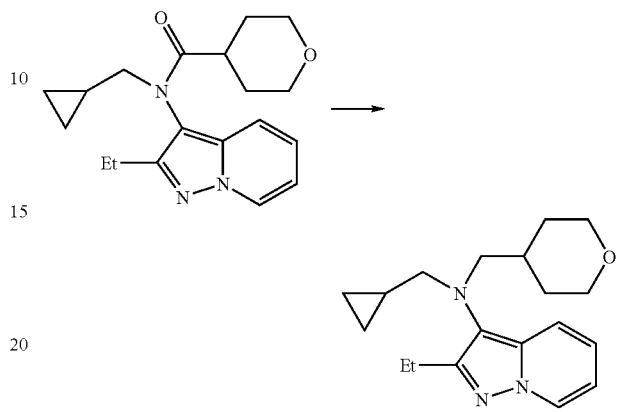

A solution of N4-cyclopropylmethyl-N4-(2-ethylpyrazolo[1,5-a]pyridin-3-yl)tetrahydro-2H-4-pyrancarboxamide (220 g, 672 mmol) in tetrahydrofuran (1100 mL) was stirred at an external temperature of 55° C. (hot water bath). A borane-tetrahydrofuran complex (1M solution, 1748 mL) was added dropwise to the reaction mixture, and after heating and stirring for 2 hours, the reaction mixture was cooled in an ice bath and 2N hydrochloric acid (437 mL) was added. The reaction mixture was then stirred for 1 hour at an external temperature of 50° C. (hot water bath). After the reaction terminated, a 5N aqueous sodium hydroxide solution (299 mL) was added dropwise to the reaction mixture to adjust it to pH 8, and the aqueous layer was removed. Toluene (2200 mL) was then added to the organic extract, and after washing the organic extract twice with water, it was concentrated under reduced pressure to afford 209 g of the title compound (99.2% yield).

$^1$H NMR (400 MHz, CDCl$_3$) δ −0.04-0.06 (m, 2H), 0.30-0.40 (m, 2H), 0.73-0.86 (m, 1H), 1.18-1.36 (m, 2H), 1.33 (t, J=7.6 Hz, 3H), 1.46-1.60 (m, 1H), 1.72 (br d, J=12.8 Hz, 2H), 2.82 (q, J=7.6 Hz, 2H), 2.84 (d, J=7.2 Hz, 2H), 3.01 (d, J=7.2 Hz, 2H), 3.28 (ddd, J=12.0, 12.0, 2.0 Hz, 2H), 3.92 (br dd, J=12.0, 4.4 Hz, 2H), 6.59 (ddd, J=6.8, 6.8, 1.2 Hz, 1H), 6.95 (ddd, J=8.8, 6.8, 1.2 Hz, 1H), 7.44 (ddd, J=8.8, 1.2, 1.2 Hz, 1H), 8.29 (ddd, J6.8, 1.2, 1.2 Hz, 1H).

Production Example 6X

N-Cyclopropylmethyl-N-(2-ethyl-7-iodopyrazolo[1,5-a]pyridin-3-yl)-N-tetrahydro-2H-4-pyranylmethylamine

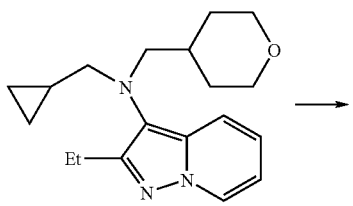

-continued

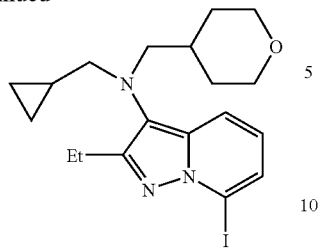

A solution of N-cyclopropylmethyl-N-(2-ethylpyrazolo[1,5-a]pyridin-3-yl)-N-tetrahydro-2H-4-pyranylmethylamine (180 g, 574 mmol) in tetrahydrofuran (1620 mL) was cooled with dry ice-ethanol bath. A 1.6M n-butyllithium-hexane solution (538 mL, 854 mmol) was added dropwise to the solution at an internal temperature of from −73° C. to −64.5° C. After stirring the reaction mixture for 1 hour at the same temperature, pentafluoroiodobenzene (115 mL, 861 mmol) was added dropwise. The reaction mixture was additionally stirred for 1 hour and 20 minutes, and then water/THF (1/1, v/v, 360 mL) was added thereto. Cooling was terminated, and then water (3600 mL) and heptane (3600 mL) were added to the reaction mixture, the aqueous layer was removed and the organic extract was washed with water (3600 mL). A 5N aqueous hydrochloric acid solution (1800 mL) was then added to the organic layer and the aqueous layer was separated off. After cooling the aqueous layer in an ice bath and adding a 5N aqueous sodium hydroxide solution (1620 mL), toluene (3600 mL) was further added to the reaction mixture and the organic layer was separated off. The aqueous layer was extracted with toluene (3600 mL), and both organic extracts were combined and concentrated to afford 220 g of the title compound as a dark green oil (87.3% yield)

$^1$H NMR (400 MHz, CDCl$_3$) δ −0.02-0.05 (m, 2H), 0.33-0.40 (m, 2H), 0.74-0.86 (m, 1H), 1.19-1.32 (m, 2H), 1.36 (t, J=7.6 Hz, 3H), 1.46-1.60 (m, 1H), 1.71 (br d, J=13.2 Hz, 2H), 2.86 (d, J=6.8 Hz, 2H), 2.88 (q, J=7.6 Hz, 2H), 3.02 (d, J=6.8 Hz, 2H), 3.28 (ddd, J=11.6, 11.6 2.0 Hz, 2H), 3.92 (br dd, J=11.6, 2.6 Hz, 2H), 6.71 (dd, J=8.8, 6.8Hz, 1H), 7.20 (dd, J=6.8, 1.2 Hz, 1H), 7.47 (dd, J=8.8, 1.2 Hz, 1H).

Production Example 7X

N-Cyclopropylmethyl-N-(2-ethyl-7-iodopyrazolo[1,5-a]pyridin-3-yl)-N-tetrahydro-2H-4-pyranylmethylamine hydrochloride

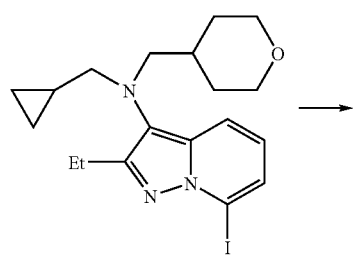

A solution of concentrated hydrochloric acid (48.5 mL, 575 mmol) in isopropanol (270 mL) was added dropwise to a solution of N-cyclopropylmethyl-N-(2-ethyl-7-iodopyrazolo[1,5-a]pyridin-3-yl)-N-tetrahydro-2H-4-pyranylmethylamine (220 g, 501 mmol) in dimethyl carbonate (3600 mL) over a period of 20 minutes at room temperature, and the reaction mixture was stirred for 15 hours at room temperature. The reaction mixture was then cooled in an ice water bath, and dimethyl carbonate (900 mL) was added thereto. After stirring the reaction mixture for about 5 hours, the precipitated solid was collected by filtration and washed with dimethyl carbonate (900 mL). It was then dried under reduced pressure at 50° C. to afford 250 g of the title compound (93.7% yield) as a solvate with dimethyl carbonate and isopropanol.

$^1$H NMR (400 MHz, CD$_3$OD) δ 0.08-0.40 (m, 2H), 0.42-0.56 (m, 2H), 0.81-0.94 (m, 1H), 1.30-1.60 (m, 4H), 1.50 (t, J=7.5 Hz, 3H), 1.67-1.81 (m, 1H), 3.06 (q, J=7.5 Hz, 2H), 3.24 (ddd, J=11.7, 11.7 2.4 Hz, 2H), 3.56-3.76 (m, 4H), 3.82-3.90 (m, 2H), 7.20 (dd, J=8.8, 7.1 Hz, 1H), 7.66 (d, J=7.1 Hz, 1H), 7.98 (d, J=8.8 Hz, 1H).

Production Example 8X

2-Bromo-1,3-dimethoxy-5-(methoxymethyl)benzene

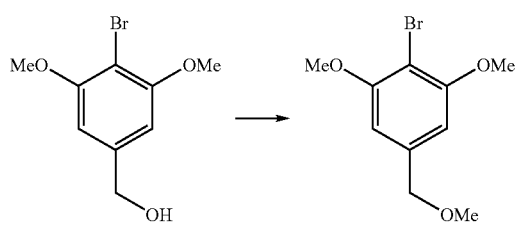

Mesyl chloride (34.5 mL, 446 mmol) was added to a solution of (4-bromo-3,5-dimethoxyphenyl)methanol (100 g, 405 mmol) and triethylamine (67.5 mL, 484 mmol) in 1,2-dimethoxyethane (1000 mL) while cooling with ice, and the reaction mixture was stirred for 30 minutes. After adding a 28% sodium methoxide in methanol (350 mL, 1.72 mol) to the reaction mixture, it was further stirred for 3 hours at room temperature. Upon completion of the reaction, toluene (1000 mL) and water (1000 mL) were added to the reaction mixture, the aqueous layer was removed, and the organic extract was washed with water (1000 mL), 1N hydrochloric acid (500 mL) and water (500 mL) in that order and concentrated under reduced pressure to afford 105 g of the title compound as a colorless oil (99.5% yield).

Production Example 9X 2,6-Dimethoxy-4-(methoxymethyl)phenylboric acid

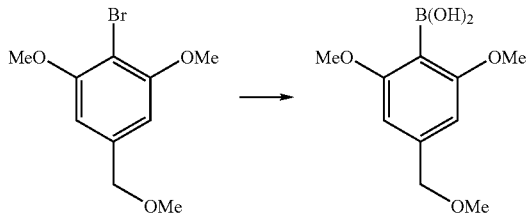

To a solution of 2-bromo-1,3-dimethoxy-5-(methoxymethyl)benzene (20.0 g, 76.6 mmol) in tetrahydrofuran (200 mL) which had been cooled in a dry ice-acetone bath was added 1.58M n-butyllithium in hexane (50.9 mL, 80.4 mmol) under a nitrogen stream, and the reaction mixture was stirred for 30 minutes. A solution of trimethoxyborane (8.75 g, 84.2 mmol) in tetrahydrofuran (20 mL) was then added to the reaction mixture, and the reaction temperature was increased to 0° C. while stirring. After adding 1N hydrochloric acid (200 mL) to the reaction mixture, it was stirred for 30 minutes at room temperature. After the reaction terminated, toluene (200 mL) was added to the reaction mixture and the organic layer was separated off, after which the aqueous layer was extracted with toluene (100 mL). The combined organic extracts were washed with water (100 mL) and then concentrated under reduced pressure. The residue was dissolved in tert-butyl methyl ether (75 mL) and the reaction mixture was stirred for 30 minutes, after which heptane (223 mL) was added thereto and the reaction mixture was further stirred for 2 hours. The precipitate was filtered out and washed with a mixed solution of tert-butyl methyl ether and heptane (1:3, 3.75 mL), and then dried at 40° C. for 24 hours to afford 12.4 g of the title compound (71.8% yield).

Production Example 10X

Methyl 4-bromo-3,5-dimethoxybenzoate

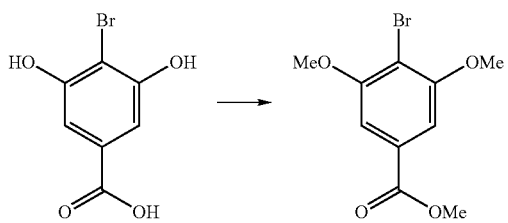

Potassium carbonate (359 g) was added to a solution of 4-bromo-3,5-dihydroxybenzoic acid (127.5 g) in N,N-dimethylformamide (1020 mL) while cooling with ice bath, and then iodomethane (143 mL) was further added. After removing the ice bath and stirring at room temperature for 17 hours, the reaction mixture was poured into ice water. The precipitated solid was collected by filtration and washed with water, and then the residue was dissolved in ethyl acetate and dried over anhydrous magnesium sulfate, and the solvent was evaporated under reduced pressure to afford the title compound (133.2 g) as a white solid.

Production Example 11X (4-Bromo-3,5-dimethoxyphenyl)methanol

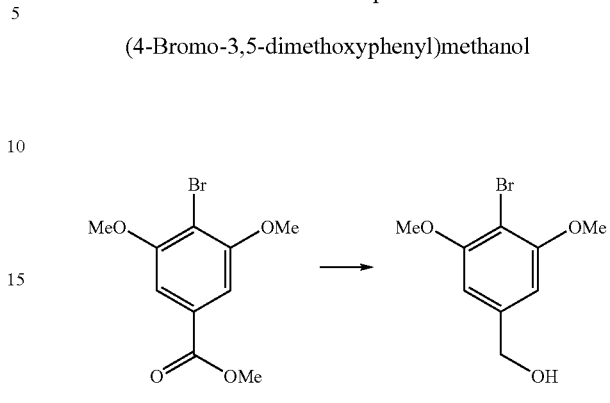

Lithium borohydride (20.8 g) was slowly added to a solution of methyl 4-bromo-3,5-dimethoxybenzoate (133.2 g) in tetrahydrofuran (500 mL) at room temperature, and the mixture was stirred for 3 hours while heating to reflux. The reaction mixture was cooled to room temperature, ice water (1.5 L) was added, and then ethyl acetate (1.2 L) was further added for extraction. The obtained organic extract was washed with brine and dried over anhydrous magnesium sulfate, and the solvent was evaporated under reduced pressure to afford the title compound (118.8 g) as a white solid.

Production Example 12X

2-Bromo-1,3-dimethoxy-5-(methoxymethyl)benzene

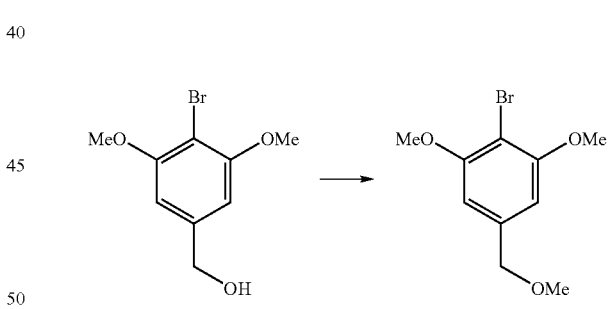

Sodium hydride (60% in oil; 24.7 g) was added to a solution of (4-bromo-3,5-dimethoxyphenyl)methanol (118.8 g) in N,N-dimethylformamide (960 mL) while cooling with ice, and after stirring for 10 minutes, iodomethane (41.7 mL) was added dropwise, the temperature was increased to room temperature and stirring was continued for 1 hour. The obtained reaction mixture was poured into ice water (2.5 L), extraction was performed with ethyl acetate, the extract was washed with brine and dried over anhydrous magnesium sulfate, and the solvent was evaporated under reduced pressure. The residue was purified by silica gel column chromatography and the title compound (121.3 g) was obtained as a colorless oil from the n-hexane:ethyl acetate (4:1) fraction.

Production Example 13X 2,6-Dimethoxy-4-(methoxymethyl)phenylboric acid

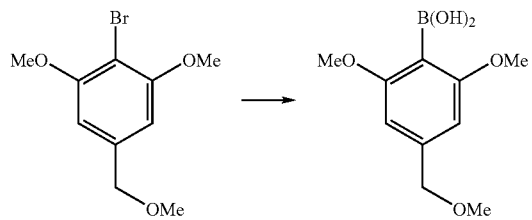

n-Butyllithium (2.64M hexane solution; 182 mL) was added dropwise to a solution of 2-bromo-1,3-dimethoxy-5-(methoxymethyl)benzene (121.3 g) in tetrahydrofuran (730 mL) at −78° C., and the mixture was stirred for 20 minutes. A solution of trimethoxyborane (61.7 mL) in tetrahydrofuran (20 mL) was then added to the reaction mixture at −78° C. When internal temperature was raised to −10° C., to the reaction mixture was added saturated aqueous ammonium chloride (730 mL), and stirring was continued for 15 minutes. The obtained reaction mixture was extracted with ethyl acetate, the extract was washed with brine and dried over anhydrous magnesium sulfate, and the solvent was evaporated under reduced pressure. The residue was purified by silica gel column chromatography and the title compound (90.4 g) was obtained as a white solid from the n-hexane: ethyl acetate (2:3) fraction.

$^1$H NMR (400 MHz, CDCl$_3$) δ 3.44 (s, 3H), 3.93 (s, 6H), 4.47 (s, 2H), 6.62 (s, 2H), 7.19 (s, 2H).

Production Example 14X 2,6-Dimethoxy-4-(methoxymethyl)phenylboric acid

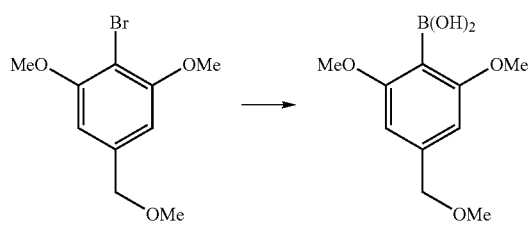

To a suspension of magnesium turnings (97.5 mg, 4.01 mmol) in tetrahydrofuran (0.5 mL) containing a small amount of added iodine, was added approximately a tenth part of a solution of 2-bromo-1,3-dimethoxy-5-(methoxymethyl)benzene (1.0 g, 3.82 mmol) in tetrahydrofuran (1 mL) under a nitrogen atmosphere, and the mixture was heated in an oil bath at 70° C. The heating was terminated upon gentle reflux of the reaction mixture and fading of the iodine color. To continue the reflux, the remaining solution of 2-bromo-1,3-dimethoxy-5-(methoxymethyl)benzene in tetrahydrofuran was added dropwise to the reaction mixture. Upon completion of the dropwise addition, the reaction mixture was further heated to reflux for 1 hour and then cooled to room temperature. The reaction mixture was then added dropwise to an ice-cooled solution of trimethyl borate (0.57 mL, 4.97 mmol) in tetrahydrofuran (0.5 mL). Upon completion of the dropwise addition and stirring for 40 minutes while cooling with ice, the mixture was stirred overnight at room temperature. An aqueous ammonium chloride solution and methanol were then added to the reaction mixture. Quantitation by liquid chromatography confirmed that the title compound had been obtained at an 89% yield.

Production Example 1Y tert-Butyl N-(2-ethylpyrazolo[1,5-a]pyridin-3-yl)carbamate

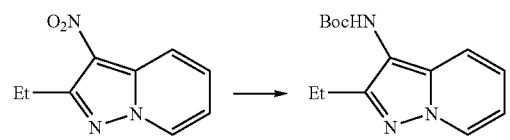

To a solution of 2-ethyl-3-nitropyrazolo[1,5-a]pyridine (7.65 g, 40 mmol) dissolved in a mixture of isopropyl alcohol (153 mL) and acetic acid (11.5 mL) was added di-tert-butyl dicarbonate (14 g, 64 mmol) and 5% palladium-carbon (1.53 g, 50% wet), and reaction was conducted for 3 hours at room temperature under a hydrogen atmosphere (0.3 MPa). After the reaction, the reaction mixture was filtered and the obtained filtrate was evaporated. The residue was dissolved in ethyl acetate, and the ethyl acetate solution was washed with aqueous sodium bicarbonate and brine. The organic extract was dried over magnesium sulfate and evaporated to dryness. Isopropyl alcohol (7.7 mL) and heptane (38.3 mL) were added thereto and the mixture was heated to 60° C. for dissolution. Slow cooling produced a precipitate, and then heptane (15.3 mL) was added thereto. After allowing the mixture to stand overnight and then stirring for 30 minutes with ice bath, the precipitate was collected by filtration and washed with heptane. The precipitate was dried under reduced pressure to afford 7.58 g of the title compound (71% yield).

Production Example 2Y tert-Butyl N-(2-ethylpyrazolo[1,5-a]pyridin-3-yl)-N-tetrahydro-2H-4-pyranylmethylcarbamate

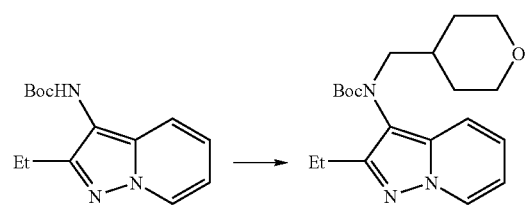

To a solution of tert-butyl N-(2-ethylpyrazolo[1,5-a]pyridin-3-yl)carbamate (12 g, 46 mmol) and potassium tert-butoxide (6.2 g, 55 mmol) dissolved in N,N-dimethylformamide (120 mL) was added tetrahydropyran-4-ylmethyl methanesulfonate (10.7 g, 55 mmol) while cooling with ice, the reaction mixture was stirred for 1 hour, and then tetrahydrofuran (200 mL) was further added and the reaction mixture was additionally stirred for 18 hours. Water (200 mL) and ethyl acetate (500 mL) were then added to the reaction mixture, and the aqueous layer was separated and extracted with ethyl acetate (300 mL). The combined organic extracts were washed with water (300 mL, 3 times) and brine, dried over magnesium sulfate and evaporated under reduced pressure to afford 18 g of the title compound as a yellow oil (≧99% yield).

$^1$H NMR (CDCl$_3$) δ 1.33 (s, 9H), 1.37 (d, J=7.6 Hz, 3H), 1.10-1.80 (m, 5H), 2.73 (q, J=7.6 Hz, 2H), 3.30-3.42 (m, 3H), 3.57-3.84 (m, 1H), 3.90-4.02 (m, 2H), 6.70 (dd, J=6.8, 6.8 Hz, 1H), 7.10 (dd, J=7.1, 6.8 Hz, 1H), 7.23 (d, J=7.1 Hz, 1H), 8.33 (d, J=6.8 Hz, 1H).

Production Example 3Y

N-(2-Ethylpyrazolo[1,5-a]pyridin-3-yl)-N-tetrahydro-2H-4-pyranylmethylamine hydrochloride

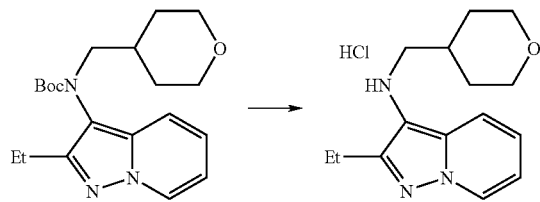

To a solution of tert-butyl N-(2-ethylpyrazolo[1,5-a]pyridin-3-yl)-N-tetrahydro-2H-4-pyranylmethylcarbamate (17.5 g, 50 mmol) dissolved in 1,2-dimethoxyethane (175 mL) was added a 4N hydrochloric acid-ethyl acetate solution (175 mL), and the reaction mixture was stirred for 3 hours at 45° C. The solvent was then evaporated under reduced pressure, 1,2-dimethoxyethane (175 mL) and hexane (175 mL) were added to the residue, the mixture was cooled on ice and the precipitate was collected by filtration to afford 11.8 g of the title compound (87% yield).

$^1$H NMR (CDCl$_3$) δ 1.26-1.35 (m, 2H), 1.40 (t, J=8.0 Hz, 3H), 1.88 (d, J=12.7 Hz, 2H), 2.12-2.20 (m, 1H), 3.03 (q, J=8.0 Hz, 2H), 3.10-3.20 (m, 4H), 3.81 (dd, J=11.5, 2.4 Hz, 2H), 6.80 (dd, J=6.8, 6.8 Hz, 1H), 7.18 (dd, J=9.0, 6.8 Hz, 1H), 8.09 (d, J=9.0 Hz, 1H), 8.32 (d, J=6.8 Hz, 1H), 11.70 (br s, 1H).

Production Example 4Y

N-Cyclopropylmethyl-N-(2-ethylpyrazolo[1,5-a]pyridin-3-yl)-N-tetrahydro-2H-4-pyranylmethylamine

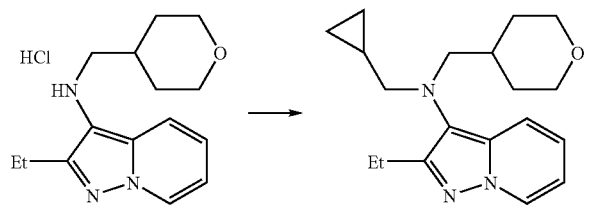

A mixture of N-(2-ethylpyrazolo[1,5-a]pyridin-3-yl)-N-tetrahydro-2H-4-pyranylmethylamine hydrochloride (10.3 g, 35 mmol) and potassium carbonate (5.8 g) in ethyl acetate (150 mL) and water (30 mL) was stirred for 8 minutes at room temperature. The organic extract was separated and then washed with brine, dried over magnesium sulfate and evaporated under reduced pressure to afford N-(2-ethylpyrazolo[1,5-a]pyridin-3-yl)-N-tetrahydro-2H-4-pyranylmethylamine (9.1 g). This compound was dissolved in tetrahydrofuran (180 mL), and then cyclopropanecarbaldehyde (7.4 g, 106 mmol) and sodium triacetoxyborohydride (10.5 g, 49.7 mmol) were added and the reaction mixture was stirred for 10 minutes. After completion of the reaction, ethyl acetate (400 mL) and water (200 mL) were added to the reaction mixture and the organic extract was separated. After extracting the aqueous layer again with ethyl acetate (200 mL), the organic extracts were combined and washed with water (100 mL) and brine (100 mL). The organic extract was dried over magnesium sulfate and evaporated under reduced pressure. The residue was purified by silica gel column chromatography (hexane:ethyl acetate=6:1) to afford 11.9 g of the title compound as a yellow oil (≧99% yield).

Production Example 5Y tert-Butyl N-cyclopropylmethyl-N-(2-ethylpyrazolo[1,5-a]pyridin-3-yl)carbamate

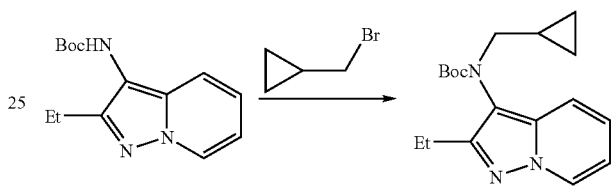

To a solution of tert-butyl N-(2-ethylpyrazolo[1,5-a]pyridin-3-yl) carbamate (4.93 g, 18.0 mmol) and potassium tert-butoxide (2.54 g, 22.6 mmol) dissolved in N,N-dimethylformamide (49 mL) was added (bromomethyl)cyclopropane (2.02 mL, 20.8 mmol) dropwise. The reaction mixture was stirred at room temperature for 15 minutes, and then ethyl acetate (50 mL), heptane (50 mL) and water (50 mL) were added and the organic layer was separated off. The aqueous layer was then again extracted with heptane (30 mL). The combined organic extracts were washed with water (25 mL×2 times) and 10% brine (10 mL). The organic extract was dried over magnesium sulfate and evaporated under reduced pressure to afford 6.5 g of the title compound (≧99% yield).

$^1$H NMR (400 MHz, CDCl$_3$) δ 0.00-0.19 (m, 2H), 0.30-0.50 (m, 2H), 0.95 (br s, 1H), 1.20-1.60 (m, 9H), 1.34 (t, J=7.6 Hz, 3H), 2.75 (q, J=7.6 Hz, 2H), 3.25-3.40 (m, 1H), 3.44-3.62 (m, 1H), 6.67 (t, J=6.8 Hz, 1H), 7.07 (t, J=7.2 Hz, 1H), 7.32 (d, J=8.8 Hz, 1H), 8.31 (d, J=7.2 Hz, 1H)

Production Example 6Y tert-Butyl N-(7-bromo-2-ethylpyrazolo[1,5-a]pyridin-3-yl)-N-cyclopropylmethylcarbamate

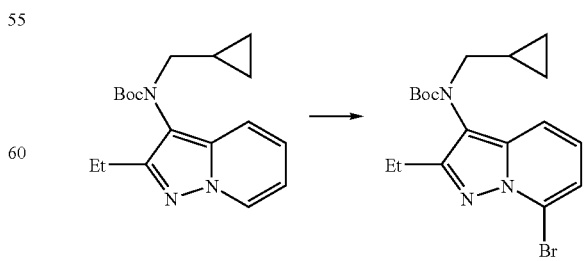

A solution of n-butyllithium in hexane (1.6M, 3.88 mL, 6.18 mmol) was added dropwise to a solution of tert-butyl N-cyclopropylmethyl-N-(2-ethylpyrazolo[1,5-a]pyridin-3-yl)carbamate (1.5 g, 4.76 mmol) in tetrahydrofuran (15 mL) at −70° C. After stirring the reaction mixture for 50 minutes at the same temperature, 1,2-dibromotetrafluoroethane (1.0 mL, 8.33 mmol) was added dropwise to the reaction mixture. The temperature of the reaction mixture was slowly increased and aqueous sodium bicarbonate was added at 0° C. The reaction mixture was extracted with ethyl acetate, and the organic extract was washed with brine, dried over magnesium sulfate and evaporated. The residue was purified by silica gel column chromatography (hexane:ethyl acetate=8:1) to afford 1.65 g of the title compound as a yellow oil (87.8% yield).

$^1$H NMR (400 MHz, CDCl$_3$) δ 0.00-0.20 (m, 2H), 0.39 (m, 2H), 0.95 (m, 1H), 1.25-1.60 (m, 9H), 1.35 (t, J=8.0 Hz, 3H), 2.56 (q, J=8.0 Hz, 2H), 3.20-3.35 (m, 1H), 3.50-3.65 (m, 1H), 6.93-7.04 (m, 2H), 7.35 (dd, J=1.6, 8.4 Hz, 1H).

Production Example 7Y tert-Butyl N-cyclopropylmethyl-N-7-(2,6-dimethoxy-4-(methoxymethyl)phenyl)-2-ethylpyrazolo[1,5-a]pyridin-3-ylcarbamate

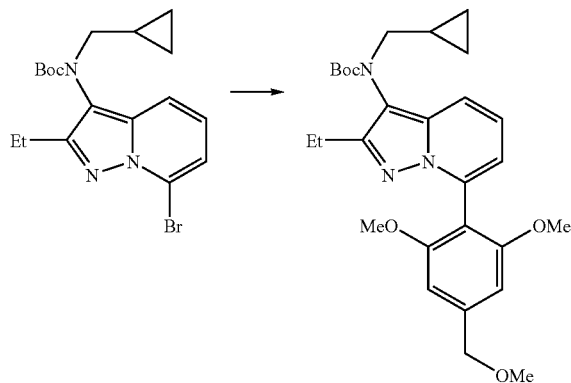

After adding 1,2-dimethoxyethane (26.7 mL) and water (13.4 mL) to a mixture of tert-butyl N-(7-bromo-2-ethylpyrazolo[1,5-a]pyridin-3-yl)-N-cyclopropylmethylcarbamate (422 mg, 1.34 mmol), 2,6-dimethoxy-4-(methoxymethyl)phenylboric acid (399 mg, 1.74 mmol), tetrakis(triphenylphosphine)palladium(0) (231 mg, 0.20 mmol) and barium hydroxide octahydrate (634 mg, 2.0 mmol), the mixture was degassed under reduced pressure at 0° C. while stirring. The reaction mixture was heated to 90° C. and then stirred for 90 minutes. After the reaction, water was added to the reaction mixture and extracted with ethyl acetate. The organic extract was washed with brine, dried over magnesium sulfate and evaporated. The residue was purified by silica gel column chromatography (n-hexane:ethyl acetate =4:1-2:1) and then suspended and purified with heptane to afford 487 mg of the title compound (73% yield).

$^1$H NMR (400 MHz, CDCl$_3$) δ 0.10-0.22 (m, 2H), 0.35-0.50 (m, 2H), 1.15 (m, 1H), 1.24 (t, J=7.6 Hz, 3H), 1.20-1.68 (m, 9H), 1.62 (s, 2H), 2.70 (q, J=7.6 Hz, 2H), 3.49 (s, 3H), 3.68-3.78 (m, 6H), 4.53 (s, 2H), 6.64-6.73 (m, 3H), 7.11 (t, J=8.0 Hz, 1H), 7.31 (d, J=8.8 Hz, 1H)

Production Example 8Y

N-Cyclopropylmethyl-N-7-[2,6-dimethoxy-4-(methoxymethyl)phenyl]-2-ethylpyrazolo[1,5-a]pyridin-3-ylamine

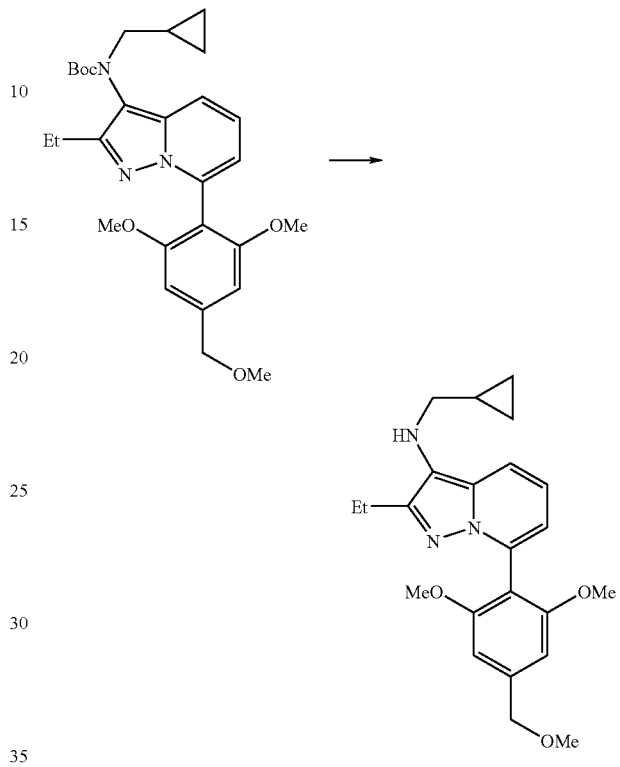

A mixture of tert-butyl N-cyclopropylmethyl-N-7-(2,6-dimethoxy-4-(methoxymethyl)phenyl)-2-ethylpyrazolo[1,5-a]pyridin-3-ylcarbamate (20 mg, 0.04 mmol) in trifluoroacetic acid (1.0 mL) was stirred for 30 minutes at room temperature. A 5N aqueous sodium hydroxide was added to the reaction mixture for neutralization, and then extracted with ethyl acetate. The organic extract was washed with aqueous sodium bicarbonate and brine in that order and dried over magnesium sulfate. This was evaporated under reduced pressure to afford 13 mg of the title compound (81% yield).

$^1$H NMR (400 MHz, CDCl$_3$) δ 0.18 (q, J=4.4 Hz, 2H), 0.45-0.55 (m, 2H), 1.10-1.30 (m, 1H), 1.23 (t, J=7.2 Hz, 3H), 2.10 (br s, 1H), 2.75 (q, J=7.2 Hz, 2H), 2.89 (d, J=6.8 Hz, 2H), 3.47 (s, 3H), 3.70 (s, 6H), 4.51 (s, 2H), 6.54 (dd, J=0.8, 6.8 Hz, 1H), 6.66 (s, 2H), 7.00 (dd, J=6.8, 9.2 Hz, 1H), 7.40 (dd, J=0.8, 8.4 Hz, 1H)

Production Example 9Y

7-Bromo-2-ethylpyrazolo[1,5-a]pyridine

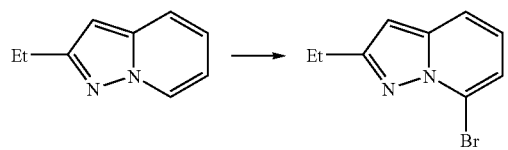

A solution of 2-ethylpyrazolo[1,5-a]pyridine (5.0 g, 34.2 mmol) in tetrahydrofuran (50 mL) was cooled to below −70° C. under a nitrogen stream, and then a solution of n-butyllithium in hexane (32.5 mL, 1.58M solution, 51.4 mmol)

was added dropwise at below −60° C. After stirring for 1 hour, bromopentafluorobenzene (9.3 g, 37.7 mmol) was added dropwise to the reaction mixture at below −60° C. The reaction mixture was stirred for 2 hours at below −70° C., and then water (50 mL) was added to the reaction mixture and the temperature was raised to room temperature. Ethyl acetate (50 mL) and water (50 mL) were added thereto, and extraction was performed with ethyl acetate. The organic extract was washed twice with 5% brine (50 mL) and dried over anhydrous magnesium sulfate, and then the solvent was evaporated under reduced pressure to afford 6.9 g of the title compound.

Production Example 10Y

7-Bromo-2-ethyl-3-nitropyrazolo[1,5-a]pyridine

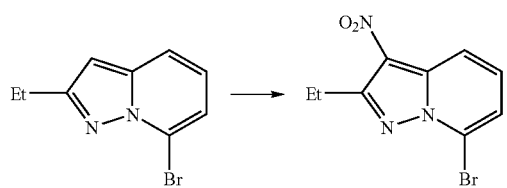

Fuming nitric acid (1.7 mL) was added dropwise to a solution of 7-bromo-2-ethylpyrazolo[1,5-a]pyridine (6.9 g, 34.2 mmol) in concentrated sulfuric acid (13.8 mL) at an internal temperature of below 30° C. while cooling with ice. After stirring the reaction mixture for 30 minutes, it was added to ice water (138 mL) and the precipitate was filtered out. The obtained precipitate was added ethyl acetate (226 mL) and methanol (38 mL), and the mixture was heated to 70° C., and then the precipitate was collected by filtration while cooling with ice. The solvent of the obtained filtrate was evaporated under reduced pressure, and the concentrated residue was recrystallized from heptane-ethyl acetate (1:1) to afford 2.4 g of the title compound as light brown crystals (31% yield).

Production Example 11Y

7-[2,6-Dimethoxy-4-(methoxymethyl)phenyl]-2-ethyl-3-nitropyrazolo[1,5-a]pyridine

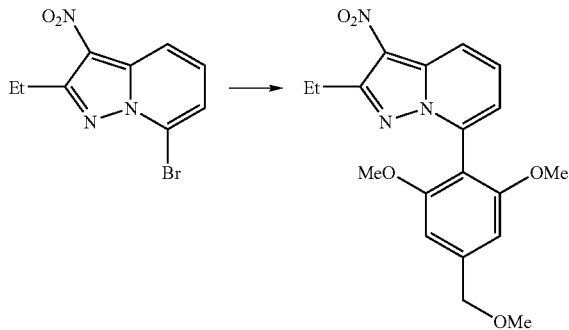

A mixture of 7-bromo-2-ethyl-3-nitropyrazolo[1,5-a]pyridine (3.0 g, 11.1 mmol), 2,6-dimethoxy-4-(methoxymethyl)phenylboric acid (5.0 g, 22.2 mmol), palladium acetate (125 mg, 0.55 mmol), triphenylphosphine (578 mg, 2.22 mmol), tripotassium phosphate hydrate (5.3 g, 22.2 mmol) and 1,2-dimethoxyethane (30 mL) was heated to reflux for 14 hours under a nitrogen atmosphere. The reaction mixture was cooled to room temperature, ethyl acetate (100 mL) and water (50 mL) were added and the organic layer was separated off. The organic extract was then washed with 10% brine (50 mL), 1N hydrochloric acid (50 mL) and 10% aqueous ammonia (50 mL) in that order. The organic extract was dried over anhydrous magnesium sulfate and the solvent was evaporated under reduced pressure. The obtained concentrated residue was purified by silica gel column chromatography to afford 3.45 g of the title compound (84% yield).

$^1$H NMR (400 MHz, CDCl$_3$) δ 1.25 (t, J=7.4 Hz, 3H), 3.15 (q, J=7.4 Hz, 2H), 3.50 (s, 3H), 3.78 (s, 6H), 4.57 (s, 2H), 6.65 (s, 2H), 7.05 (dd, J=7.0, 1.0 Hz, 1H), 7.66 (dd, J=9.0, 7.0 Hz, 1H), 8.36 (dd, J=9.0, 1.0 Hz, 1H).

Production Example 12Y

7-[2,6-Dimethoxy-4-(methoxymethyl)phenyl]-2-ethylpyrazolo[1,5-a]pyridine-3-amine

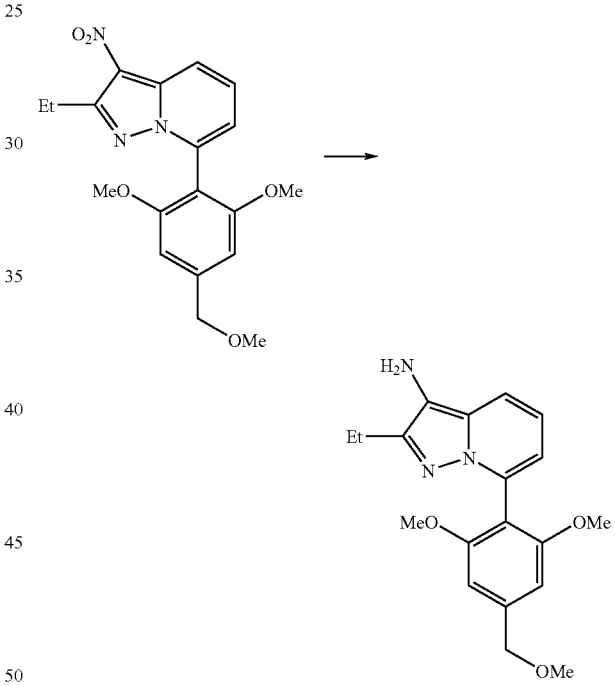

A mixture of 7-[2,6-dimethoxy-4-(methoxymethyl)phenyl]-2-ethyl-3-nitropyrazolo[1,5-a]pyridine (850 mg, 2.3 mmol), 10% palladium-carbon (50% wet, 330 mg) and methanol (19 mL) was stirred for 13 hours at 50° C. under a hydrogen atmosphere at atmospheric pressure. After cooling the reaction mixture to room temperature, the reaction mixture was filtered through celite to remove the catalyst. The solvent of the obtained filtrate was evaporated under reduced pressure to afford 3.45 g of the title compound (84% yield).

$^1$H NMR (400 MHz, CDCl$_3$) δ 1.24 (t, J=7.4 Hz, 3H), 1.46-1.96 (br s, 2H), 2.76 (q, J=7.4 Hz, 2H), 3.48 (s, 3H), 3.70 (s, 6H), 4.52 (s, 2H), 6.52 (d, J=6.3 Hz, 1H), 6.66 (s, 2H), 6.99 (dd, J=8.6, 6.3 Hz, 1H), 7.32 (d, J=8.6 Hz, 1H).

Production Example 13Y

N-Cyclopropylmethyl-N-7-[2,6-dimethoxy-4-(methoxymethyl)phenyl]-2-ethylpyrazolo[1,5-a]pyridin-3-ylamine

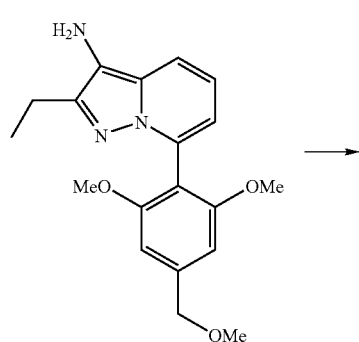

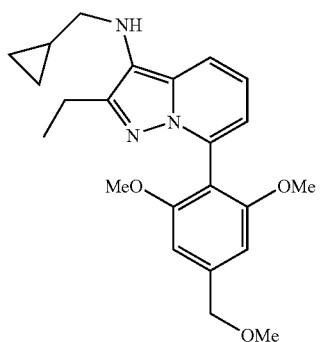

A mixture of 7-[2,6-dimethoxy-4-(methoxymethyl)phenyl]-2-ethylpyrazolo[1,5-a]pyridine-3-amine (400 mg, 1.17 mmol), cyclopropanecarbaldehyde (0.122 mL, 1.64 mmol) and tetrahydrofuran (2 mL) was heated for 1 hour at 50° C. The reaction mixture was then added dropwise to ice-cooled diisobutylaluminum hydride (1M toluene solution, 3.51 mL, 3.51 mmol). The reaction mixture was stirred for 20 minutes, and then 1N hydrochloric acid (2 mL) and ethyl acetate (20 mL) were added to the reaction mixture and extraction was performed with ethyl acetate. The organic extract was washed twice with water (10 mL) and dried over anhydrous magnesium sulfate, and then the solvent was evaporated under reduced pressure. The obtained concentrated residue was recrystallized from heptane:ethyl acetate (10:1) to afford 290 mg of the title compound as white crystals (63% yield).

$^1$H NMR (400 MHz, CDCl$_3$) (0.18 (q, J=4.4 Hz, 2H), 0.45-0.55 (m, 2H), 1.10-1.30 (m, 1H), 1.23 (t, J=7.2 Hz, 3H), 2.10 (br s, 1H), 2.75 (q, J=7.2 Hz, 2H), 2.89 (d, J=6.8 Hz, 2H), 3.47 (s, 3H), 3.70 (s, 6H), 4.51 (s, 2H), 6.54 (dd, J=6.8, 0.8 Hz, 1H), 6.66 (s, 2H), 7.00 (dd, J=9.2, 6.8 Hz, 1H), 7.40 (dd, J=8.4, 0.8 Hz, 1H).

Example 1X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine tosylate

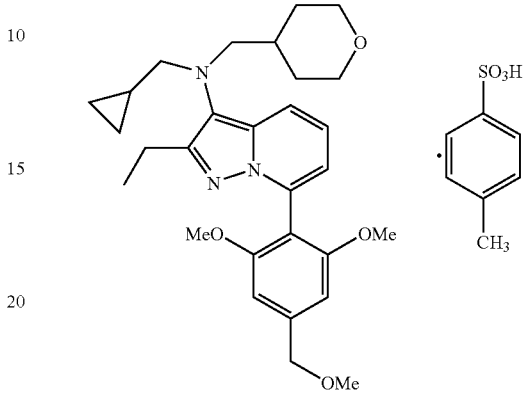

A mixture of N-cyclopropylmethyl-N-(2-ethyl-7-iodopyrazolo[1,5-a]pyridin-3-yl)-N-(tetrahydro-2H-4-pyranylmethyl)amine hydrochloride (193 g, 405 mmol), 2,6-dimethoxy-4-(methoxymethyl)phenylboric acid (143 g, 105 mmol, 1.56 equivalents), palladium acetate (4.7 g, 21 mmol, 5 mol %), triphenylphosphine (27.6 g, 105 mmol, 26 mol %), potassium carbonate (203 g, 1.47 mmol, 3.63 equivalents), 1,2-dimethoxyethane (6667 mL) and water (3333 mL) in a flask was heated in a 100° C. oil bath, the reaction system was purged with nitrogen gas. After about 6 hours from the start of reflux, the reaction mixture was cooled to room temperature.

Next, toluene (2000 mL) was added to the reaction mixture and the separated aqueous layer was removed. The toluene layer was extracted twice with 5N hydrochloric acid (first time: 3000 mL, second time: 1000 mL). Isopropyl acetate (2000 mL) was added to the aqueous layer, and while cooling in an ice water bath, a 5N aqueous sodium hydroxide solution (4200 mL) was added for adjustment to pH 14, and the isopropyl acetate layer was separated off. The isopropyl acetate layer was then washed with a 10% aqueous ethylenediamine solution (2000 mL, 3 times) and water (2000 mL, 2 times), and after concentration, ethanol (400 mL) was added for azeotropic distillation and the reaction mixture was concentrated to afford 207 g of a green solid.

The residue was dissolved in ethanol (1720 mL) while heating, and a solution of p-toluenesulfonic acid monohydrate (65.5 g, 344 mmol) in ethanol (170 mL) was added dropwise over a period of 3 minutes at an internal temperature of 60° C. After allowing the mixture to cool while stirring, seed crystals (100 mg) were added when the internal temperature reached 35° C. After 30 minutes, the mixture was cooled in a thermostat bath at 7° C. and stirred for 15 hours and 45 minutes. The precipitated crystals were then filtered out and washed with isopropanol (400 mL). The crystals were dried under reduced pressure at 60° C. for 3.5 hours to afford 214 g of the title compound as white crystals (79.5% yield).

Example 2X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine

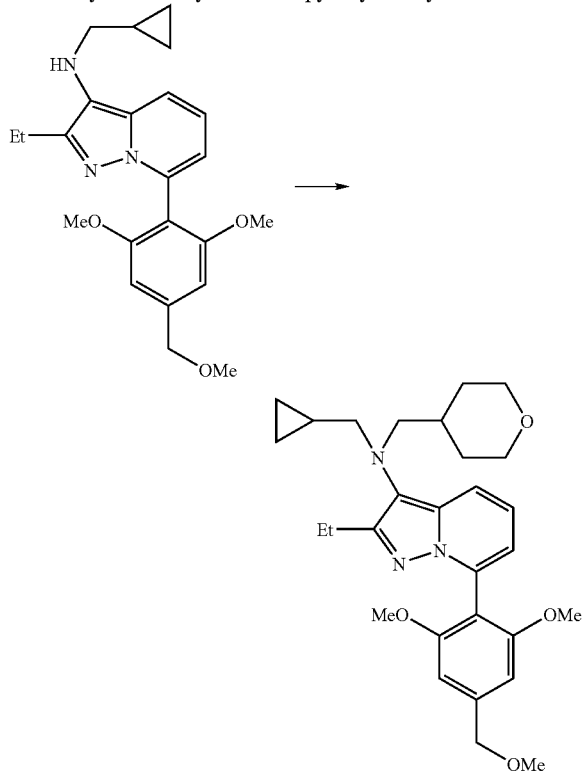

A mixture of N-cyclopropylmethyl-4-(methoxymethyl)phenyl]-2-ethylpyrazolo[1,5-a]pyridin-3-ylamine (20 mg, 0.05 mmol), sodium iodide (75 mg, 0.50 mmol), tetrahydro-2H-4-pyranylmethyl methanesulfonate (49 mg, 0.25 mmol) and sodium carbonate (10 mg) dissolved in dimethylformamide (0.5 mL) was stirred for 90 minutes at room temperature. Water and ethyl acetate were then added to the reaction mixture and extraction was performed with ethyl acetate. The organic extract was dried over magnesium sulfate and then evaporated. The residue was purified by silica gel column chromatography to afford 21 mg of the title compound (84% yield).

Example 3X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine hydrochloride

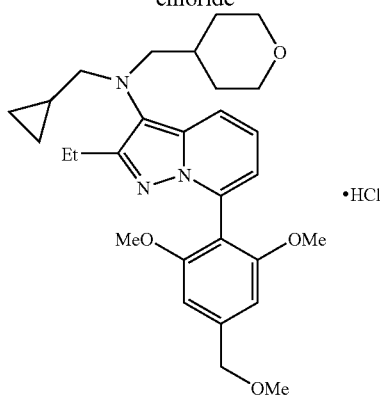

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (2.2 g) dissolved in ethyl acetate (30 mL) was added 4N hydrochloric acid-ethyl acetate (1.17 mL) at room temperature, the reaction mixture was stirred while cooling with ice, and the precipitate was collected by filtration to afford a crude product of the title compound (2.2 g) as a white powder.

The obtained crude product (2.2 g) was recrystallized from a mixed solvent of t-butyl methyl ether (500 mL) and ethyl acetate (700 mL) to afford the title compound (1.5 g).

$^1$H NMR (400 MHz, DMSO-$d_6$, at 100° C.) δ −0.04-0.10 (m, 2H), 0.30-0.38 (m, 2H), 0.77-0.87 (m, 1H), 1.14-1.25 (m, 5H), 1.55-1.70 (m, 3H), 2.73 (q, J=8 Hz, 2H), 2.99 (br s, 2H), 3.14 (br s, 2H), 3.21 (br ddd, J=11, 11, 1 Hz, 2H), 3.41 (s, 3H), 3.64 (s, 6H), 3.80 (ddd, J=11, 6, 4 Hz, 2H), 4.50 (s, 2H), 6.59 (br d, J=7 Hz, 1H), 6.74 (s, 2H), 7.11 (br t, J=7 Hz, 1H), 7.59 (br s, 1H).

Example 4X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine sulfate

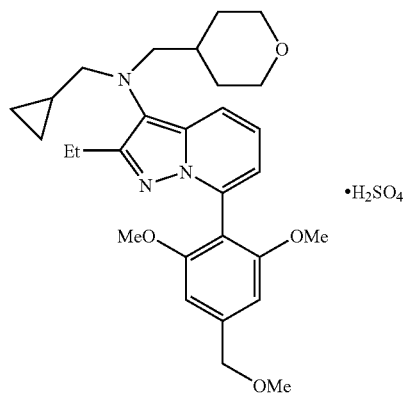

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (2.01 g) dissolved in 2-propanol (50 mL) was added 3M sulfuric acid (0.68 mL) while cooling with ice and the reaction mixture was stirred. The reaction mixture was then evaporated under reduced pressure to afford a crude product of the title compound.

The obtained crude product was recrystallized from a mixed solvent of 2-propanol (40 mL) and ethanol (20 mL) to afford the title compound (1.04 g).

$^1$H NMR (400 MHz, DMSO-$d_6$, at 100° C.) δ −0.02-0.07 (m, 2H), 0.32-0.38 (m, 2H), 0.75-0.87 (m, 1H), 1.14-1.25 (m, 5H), 1.55-1.70 (m, 3H), 2.70 (q, J=8 Hz, 2H), 2.97 (br s, 2H), 3.12 (br s, 2H), 3.22 (br ddd, J=11, 11, 2 Hz, 2H), 3.41 (s, 3H), 3.64 (s, 6H), 3.80 (br d, J=11 Hz, 2H), 4.50 (s, 2H), 6.58 (br d, J=7 Hz, 1H), 6.74 (s, 2H), 7.10 (br dd, J=8, 7 Hz, 1H), 7.54 (br d, J=8 Hz, 1H).

Example 5X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine methanesulfonate

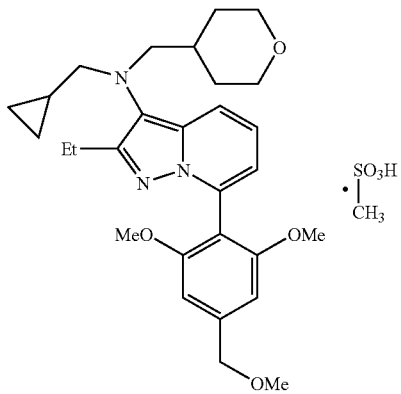

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (1.78 g) dissolved in ethyl acetate (40 mL) was added methanesulfonic acid (234 μL), and the reaction mixture was stirred at room temperature and evaporated under reduced pressure. The obtained residue was washed with a mixed solvent of n-hexane:ethyl acetate (10:1) to afford a crude product of the title compound (2.1 g).

The obtained crude product (2.1 g) was recrystallized from a mixed solvent of t-butyl methyl ether (400 mL) and ethyl acetate (150 mL) to afford the title compound (1.6 g).

$^1$H NMR (400 MHz, DMSO-$d_6$, at 100° C.) δ −0.03-0.07 (m, 2H), 0.32-0.40 (m, 2H), 0.75-0.87 (m, 1H), 1.12-1.25 (m, 5H), 1.53-1.70 (m, 3H), 2.41 (s, 3H), 2.70 (q, J=8 Hz, 2H), 2.97 (br s, 2H), 3.11 (br s, 2H), 3.22 (br ddd, J=11, 11, 1 Hz, 2H), 3.41 (s, 3H), 3.64 (s, 6H), 3.80 (br d, J=11 Hz, 2H), 4.50 (s, 2H), 6.57 (br d, J=6 Hz, 1H), 6.74 (s, 2H), 7.09 (br dd, J=7, 6 Hz, 1H), 7.53 (br d, J=7 Hz, 1H).

Example 6X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine tosylate

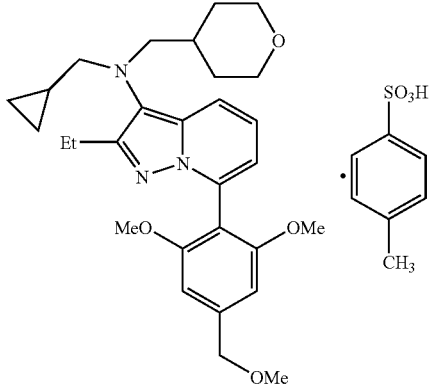

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (1.6 g) dissolved in ethyl acetate (25 mL) was added p-toluenesulfonic acid monohydrate (617 mg), and the reaction mixture was stirred at room temperature. The precipitate was filtered out to afford a crude product of the title compound (2.18 g).

The obtained crude product (2.18 g) was recrystallized from a mixed solvent of t-butyl methyl ether (640 mL) and ethyl acetate (770 mL) to afford the title compound (1.9 g).

$^1$H NMR (400 MHz, DMSO-$d_6$, at 100° C.) δ −0.03-0.07 (m, 2H), 0.30-0.40 (m, 2H), 0.75-0.87 (m, 1H), 1.14-1.25 (m, 5H), 1.53-1.70 (m, 3H), 2.29 (s, 3H), 2.70 (q, J=8 Hz, 2H), 2.97 (br s, 2H), 3.11 (br s, 2H), 3.22 (br dd, J=11, 11 Hz, 2H), 3.41 (s, 3H), 3.64 (s, 6H), 3.80 (br d, J=11 Hz, 2H), 4.50 (s, 2H), 6.58 (br d, J=6 Hz, 1H), 6.74 (s, 2H), 7.06-7.14 (m, 3H), 7.49-7.58 (m, 3H).

Example 7X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine tosylate

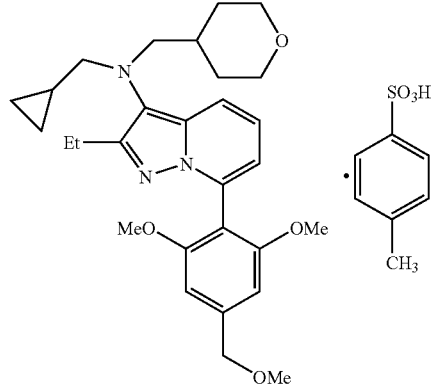

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (500 mg) dissolved in ethanol (5 mL) was added a solution of p-toluenesulfonic acid monohydrate (172 mg) in ethanol (1 mL) while heating to reflux, and the reaction mixture was stirred while allowing it to cool to room temperature. After further cooling the reaction mixture to an internal temperature of −20° C., the precipitated crystals were filtered out to afford the title compound (629 mg).

Example 8X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine hydrobromide

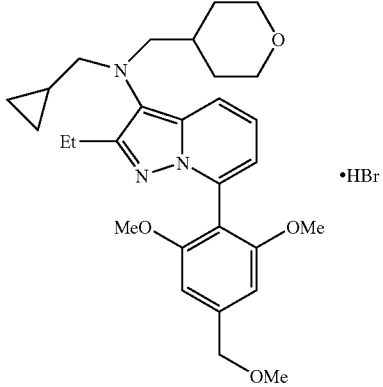

After adding a 48% aqueous hydrobromic acid solution (0.69 mL) to a solution of N-cyclopropylmethyl-N-7-[2,6-dimethoxy-4-(methoxymethyl)phenyl]-2-ethylpyrazolo[1, 5-a]pyridin-3-yl-N-tetrahydro-2H-4-pyranylmethylamine (2.0 g) in ethyl acetate (20 mL), the reaction mixture was vigorously stirred at room temperature. The obtained precipitate was filtered out to afford a crude product of the title compound (2.34 g).

The obtained crude product (2.34 g) was recrystallized from ethanol (60 mL) to afford the title compound (2.14 g).

$^1$H NMR (400 MHz, DMSO-$d_6$, at 100° C.) δ −0.03-0.07 (m, 2H), 0.30-0.40 (m, 2H), 0.75-0.87 (m, 1H), 1.14-1.24 (m, 5H), 1.55-1.70 (m, 3H), 2.71 (q, J=8 Hz, 2H), 2.98 (br s, 2H), 3.13 (br s, 2H), 3.21 (br ddd, J=11, 11, 1 Hz, 2H), 3.41 (s, 3H), 3.64 (s, 6H), 3.80 (br d, J=11 Hz, 2H), 4.50 (s, 2H), 6.59 (br d, J=6 Hz, 1H), 6.74 (s, 2H), 7.10 (br s, 1H), 7.56 (br s, 1H).

Example 9X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine benzenesulfonate

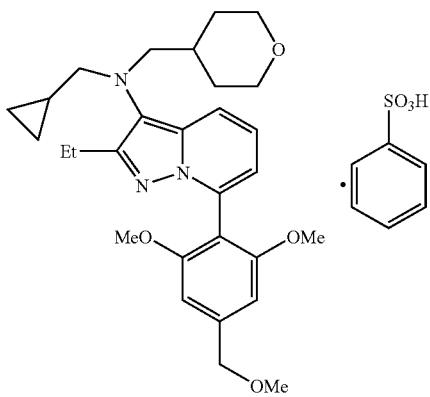

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (320 mg) dissolved in ethyl acetate (10 mL) was added benzenesulfonic acid monohydrate (108 mg), and the reaction mixture was stirred at room temperature. The obtained precipitate was filtered out to afford a crude product of the title compound (330 mg).

The obtained crude product (330 mg) was recrystallized from a mixed solvent of t-butyl methyl ether (70 mL) and ethyl acetate (80 mL) to afford the title compound (106 mg).

$^1$H NMR (400 MHz, DMSO-$d_6$, at 100° C.) δ −0.03-0.07 (m, 2H), 0.30-0.40 (m, 2H), 0.75-0.87 (m, 1H), 1.14-1.25 (m, 5H), 1.55-1.70 (m, 3H), 2.70 (q, J=8 Hz, 2H), 2.97 (br s, 2H), 3.12 (br s, 2H), 3.22 (br dd, J=11, 11 Hz, 2H), 3.41 (s, 3H), 3.64 (s, 6H), 3.80 (br d, J=11 Hz, 2H), 4.50 (s, 2H), 6.57 (br d, J=8 Hz, 1H), 6.74 (s, 2H), 7.10 (br dd, J=8, 8 Hz, 1H), 7.23-7.32 (m, 3H), 7.54 (br d, J=8 Hz, 1H), 7.64 (dd, J=8, 2 Hz, 2H).

Example 10X

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine ethanesulfonate

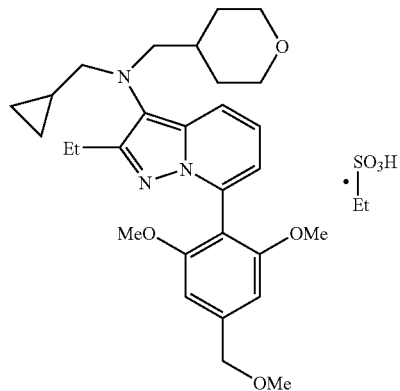

To a solution of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine (350 mg) dissolved in a mixture of ethyl acetate (5 mL) and tert-butyl methyl ether (5 mL) was added ethanesulfonic acid (83 mg), and the reaction mixture was stirred at room temperature. The obtained precipitate was filtered out to afford a crude product of the title compound (355 mg).

The obtained crude product (355 mg) was recrystallized from a mixed solvent of t-butyl methyl ether (40 mL) and ethyl acetate (40 mL) to afford the title compound (250 mg).

$^1$H NMR (400 MHz, DMSO-$d_6$, at 100° C.) δ −0.03-0.07 (m, 2H), 0.30-0.40 (m, 2H), 0.75-0.87 (m, 1H), 1.10-1.25 (m, 8H), 1.55-1.70 (m, 3H), 2.52 (q, J=7 Hz, 2H), 2.70 (q, J=8 Hz, 2H), 2.95 (br s, 2H), 3.11 (br s, 2H), 3.22 (br dd, J 12, 12 Hz, 2H), 3.41 (s, 3H), 3.64 (s, 6H), 3.80 (br d, J=12 Hz, 2H), 4.50 (s, 2H), 6.57 (br d, J=7 Hz, 1H), 6.74 (s, 2H), 7.09 (br dd, J=8, 7 Hz, 1H), 7.53 (br d, J=8 Hz, 1H).

Preparation Examples

The following are examples of formulating preparations of pharmaceutical compositions comprising compounds of the present invention.

Preparation Method

After mixing a compound of the invention (N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine tosylate), mannitol, crospovidone and hydroxypropylcellulose, an appropriate amount of purified water was used for wet granulation. The granulated product was dried and then size-controlled. Crospovidone and magnesium stearate were placed with the granules prior to mixing and tableting. The obtained tablets were film coated with an aqueous solution of a coating agent (a mixture of hydroxypropylmethylcellulose, talc, Macrogol 6000, titanium oxide and iron sesquioxide). The amounts of materials used per tablet are shown in Table 1.

TABLE 1

Preparation Examples: Amounts of materials used per tablets (mg)

| Material | Purpose | 0.5 mg tablet | 5 mg tablet | 25 mg tablet |
|---|---|---|---|---|
| The compound of the present invention *1 | major ingredient | 0.675 | 6.75 | 33.75 |
| Mannitol | excipient | 170.925 | 164.85 | 137.85 |
| Crospovidone | disintegrator | 10 | 10 | 10 |
| Hydroxypropyl cellulose | binder | 6 | 6 | 6 |
| Purified water | solvent | q.s. | q.s. | q.s. |
| Subtotal | — | 187.6 | 187.6 | 187.6 |
| Crospovidone | disintegrator | 10 | 10 | 10 |
| Magnesium stearate | lubricant | 2.4 | 2.4 | 2.4 |
| Subtotal | — | 200 | 200 | 200 |
| Coating agent *2 | coating agent | 8 | 8 | 8 |
| Purified water | solvent | q.s. | q.s. | q.s. |
| Total | — | 208 | 208 | 208 |

*1: N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine tosylate
*2: Mixture of hydroxypropylmethylcellulose, talc, Macrogol 6000, titanium oxide and iron sesquioxide Test Examples The corticotropin releasing hormone receptor (CRFR) binding affinities, cAMP production inhibitions, antianxiety effects and drug metabolizing enzyme inducibilities of the compounds of the invention were evaluated. The test methods and results were as follows.

Test Example 1

<CRFR Binding Experiment>

(1) Preparation of CRFR1-Expressing Cells:

The membrane fraction of human CRFR1 high-expressing cells was used as the material for a CRFR binding experiment. The CRFR-expressing cells were prepared in the following manner. The full-length CRFR1 gene was obtained by PCR using human brain cDNA library (Quick-Clone™ Clontech). The obtained DNA fragment was inserted into a cloning vector and the nucleotide sequence was ligated. cDNA having the proper nucleotide sequence was relinked to an expression vector (pcDNA3.1™, Invitrogen). The CRFR1 expression vector was introduced into HEK293 cell, and the resistant cells which proliferated in culture medium containing G418 (1 mg/ml) were cloned by the limiting dilution method. Out of the cloned cells, cells having high binding affinity between the membrane fraction per unit of protein and sauvagine was selected according to the following binding experiment. And the selected cells were used for the experiments.

(2) Preparation of Membrane Fraction

The cloned cells obtained in (1) were collected and suspended in chilled membrane buffer (50 mM Tris-HCl, 5 mM $MgCl_2$, 2 mM EGTA, 1 mM DTT, protease inhibitor cocktail (COMPLETE™, Roche Diagnostics), pH 7.4), and after disrupting the cells with a Polytron (KINEMATICA) (level 5, 10 seconds, 4 times, ice cooling), they were centrifuged (13,000 rpm (18,000×g), 30 minutes, 4° C.) to precipitate the cell membranes. The precipitated cell membranes were suspended in membrane buffer, and were disrupted with the Polytron (level 4, 20-30 seconds, ice cooling) to prepare a dispersed suspension. The protein contents of the dispersed suspension were quantitated and this was diluted with membrane buffer containing 0.1% BSA to a protein concentration of 200 μg/ml, for use as the cell membrane fraction.

(3) Binding Experiment

A CRF binding experiment was conducted by SPA™ (Amersham Pharmacia) method using a 96-well plate. The experiment was conducted according to the instructions for SPA beads. After allowing 5 μg of the cell membrane fraction protein, 1 mg of SPA beads and 100 pM of $^{125}$I-CRF (Perkin Elmer) to stand at room temperature for 2 hours or longer in the presence of a test compound and then centrifuging (1,200 rpm (260×g), 5 minutes, room temperature), the radioactivity of each well was measured with Top-Count™ (Packard).

(4) Calculation of Binding Affinity

The radioactivity with addition of 2,000-fold excess of nonradioactive sauvagine as non-specific binding was subtracted from each value, and each value was represented as a percentage (% of control), where 100% was defined as the radioactivity with no addition of test compounds (control). The concentration exhibiting 50% (% of control) was determined from a graph plotted with the test compound concentration on the horizontal axis and the percentage (% of control) on the vertical axis, as the $IC_{50}$ value.

Test Example 2

<cAMP Production Inhibition Experiment Using AtT-20 Cells>

(1) Test Procedure:

AtT-20 cell is a cell-line derived from mouse pituitary gland tumor, which is known to respond to corticotropin releasing hormone (CRF), to produce cAMP by activation of the intracellular adenylate cyclase system, and to release adrenocorticotropic hormone (ACTH) (Biochem. Biophys. Res. Com., 106, 1364-1371, 1982). In this experiment, AtT-20 cells ($1 \times 10^5$) were suspended in D-MEM (0.1% FBS) and seeded in a 96-well plate, and then 1 mM (final concentration) phosphodiesterase inhibitor (IBMX, Calbiochem) was added prior to incubation for 30 minutes at 37° C. The diluted test compound solution was then added prior to incubation for 30 minutes at 37° C., and CRF (final concentration: 30 nM) was added prior to further incubation for 30 minutes at 37° C. The cells were collected by centrifugation (1,800 rpm (630×g), 5 minutes), and then lysed with lysis buffer (0.2% dodecyltrimethylammmonium bromide), and the intracellular cAMP production was assayed by HTRF method. cAMP kit HTRF (Nihon Schering) was used for the cAMP assay.

(2) Calculation of cAMP Production Inhibitory Activity

The obtained data were processed in the following manner. The cAMP production of each sample was represented as a percentage (% of control), with the CRF (final concentration: 30 nM)-added cells defined as 100% (control). The concentration exhibiting 50% (% of control) was determined from a graph plotted with the test compound concentration on the horizontal axis and the percentage (% of control) on the vertical axis, as the $IC_{50}$ value.

<Test Results>

In Test Example 1, all of the compounds of the present invention (Examples 1-9, 11-14, 18, 20-27, 29, 31-34, 37, 38, 40, 43, 44, 46-51, 53-60) exhibited excellent binding affinity for CRFR1. In Test Example 2, all of the compounds of the present invention (Examples 1-9, 11-14, 18, 20-24, 26, 27, 29, 32-34, 37, 38, 40, 43, 44, 46-51, 53-60) exhibited excellent inhibitory effects on CRF-induced cAMP production. Some of the results are shown in Table 2.

TABLE 2

| Compound No. (Example No.) | CRF1 receptor binding affinity $IC_{50}$ (nM) | cAMP production activity $IC_{50}$ (nM) |
|---|---|---|
| Example 1 | 71 | 4 |
| Example 3 | 49 | 5.1 |
| Example 13 | 90 | 11 |
| Example 23 | 50 | 6 |
| Example 47 | 50 | 50 |
| Example 59 | 52 | 3.5 |
| Example 60 | 30 | 3.5 |

Test Example 3

Evaluation of Antianxiety Effect by Mice in Light/Dark Chamber (1) Test Procedure:

The test of mice in light-dark chamber was carried out according to a modified method of Belzung C., Misslin R., Vogel E. et al. (Reference; Behavioural effects of the benzodiazepine receptor partial agonist RO16-6028 in mice, *Psychopharmacology*, 97, 388-391, 1989). The test apparatus used was a light/dark chamber comprising a covered black acrylic chamber (dark chamber; 15×10×20 cm), an uncovered white acrylic chamber (light chamber; 15×20×20 cm) and a black acrylic tunnel (10×7×4.5 cm) which connects dark chamber and light chamber and enables a mouse to freely move back and forth between the dark chamber and light chamber. In this test apparatus, however, a transparent acrylic polymer was used for the front side (20×20 cm) and back side (20×20 cm) of the light box to allow observation of the behavior. After setting illumination on the floor of the light box to an illuminance of 150 Lux, 5-week-old male Balb/c mice (purchased from Nihon Charles River) were introduced into the dark box at the beginning of the test. For the test, the tested compound was suspended in a 0.5% aqueous methylcellulose solution and orally administered to the test animals one hour prior to the start of the test.

(2) Calculation of Antianxiety Effect

The behavior of the mice was observed for 5 minutes after the start of the test. The light residence time was measured as an indicator of the antianxiety effect, with "light residence" defined as the state in which the limbs of the mice were on the floor of the light box. The minimum dose which significantly lengthened the light residence time with respect to the vehicle-administered group was determined as the minimum effective dose (MED). The statistical significance between the vehicle-administered group and the test compound-administered groups was analyzed by a Dunnett-type multiple comparison after one-way analysis of variance when multiple doses were set for the same test, and by the Mann-Whitney U test when only one dose was set.

<Test Results>

N-Cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine exhibited an excellent effect based on evaluation of the antianxiety effect in the test of mice in light/dark chamber, with an MED value of 10 mg/kg.

Test Example 4

Evaluation of Drug Metabolizing Enzyme (CYP3A4) Inducibility Using Cryopreserved Human Hepatocyte (1) Test Procedure:

Cryopreserved hepatocytes (In Vitro Technology) were rapidly thawed while stirring at 37° C., and then ice-cooled William's Medium E (10% FBS, +PSG) was slowly added to the cells prior to centrifugation at 500 rpm for 5 minutes. After removing the supernatant, the obtained hepatocytes were diluted with ice-cooled William's Medium E to a concentration of $5\times10^5$ cells/mL, seeded on a 48-well collagen coated plate (BD Biosciences) at $1\times10^5$ cells/cm$^2$ and incubated for about 24 hours at 37° C., 5% $CO_2$, after which the medium was changed with Hepato-STIM™ (BD Biosciences) (+EGF, PSG, −FBS) and culture was maintained for another 24 hours under conditions of 37° C., 5% $CO_2$. At approximately 48 hours after the cell seeding, the test compound or rifampicin (SIGMA, positive control) in the form of a diluted solution (using Hepato-STIM™ (+EGF, PSG, −FBS)) was added, hepatocyte were incubated for about 24 hours under conditions of 37° C., 5% $CO_2$, and the culture medium was changed with medium containing a freshly prepared dilution of the test compound or rifampicin prior to further incubation for 24 hours under the same conditions. After incubation, the cells were washed once with PBS, and the total RNA was extracted using a Qiagen RNeasy Mini kit (Qiagen). The cDNA was synthesized by reverse-transcription of extracted using TaqMan Reverse Transcription Reagents (Applied Biosystems). The reverse transcription reaction was carried out using oligo dT as primer, with treatment at 25° C. for 10 minutes followed by treatment at 48° C. for 60 minutes, after which the reverse transcriptase was inactivated by treatment at 95° C. for 10 minutes. The obtained cDNA was supplied to a PCR using a Gene Amp PCR system 9700. The obtained cDNA was quantitated using an SYBR Green PCR Core Reagents kit (Applied Biosystems), and the human CYP3A4 and GAPDH mRNA was quantitated using an ABI7700 (Applied Biosystems). The primer sequences and conditions used in the PCR are shown in Tables 3 and 4. The abbreviations used in the test example are explained below.

FBS: Fetal Bovine Serum

PSG: Penicillin (100 U/ml), Streptomycin (100 μg/ml), Glutamine (2 mM)

EGF: Epidermal Growth Factor

GAPDH: Glyceraldehyde-3-Phosphate Dehydrogenase

TABLE 3

Primer Sequences (SEQ ID NOS: 1-4)

| Isozyme | GenBank# | Primer | Name | Sequence |
|---|---|---|---|---|
| CYP3A4 | NM017460 | F | HCYP3A4_F3 | TAGCTGAGGATGAAGAATGG |
|  |  | R | HCYP3A4_R3 | GTGGATTGTTGAGAGAGTCG |
| GAPDH | M_33197 | F | hGAPDH_F | GAAGGTGAAGGTCGGAGTC |
|  |  | R | hGAPDH_R | GAAGATGGTGATGGGATTTC |

TABLE 4

PCR Conditions

| Temperature | Time | |
|---|---|---|
| 95 | 10 min | |
| 94 | 15 s | denature |
| 56 | 15 s | annealing |
| 72 | 30 s | extension |
| 40 cycles | | |

(2) Calculation of CYP3A4 Inducibility

The obtained data were processed in the following manner. The value of the amount of CYP3A4 mRNA obtained by PCR divided by the amount of GAPDH mRNA was calculated, and the ratio ("fold") of the value obtained by addition of the test compound with respect to the value of the negative control (0.1% DMSO), and the ratio of the positive control value (10 μM rifampicin) with respect to the negative control value, were both calculated. Next, for comparison of each test run, the differences between the value of the CYP3A4 mRNA amount divided by the GAPDH mRNA amount with addition of the test compound at various concentrations and with addition of the negative control were calculated as percentages, with 100% being defined as the difference between the values of the CYP3A4 mRNA amount divided by the GAPDH mRNA amount for the positive control and negative control, to determine the inducibility of each test compound.

<Test Results>

In Test Example 4, the compounds of the invention (Examples 1, 3, 59) were evaluated the induction of drug metabolizing enzyme with cryopreserved human hepatocytes in order to estimate the CYP induction in liver, to predict drug interactions as side effects of concern for administration as treatment for humans. The test results for test compound concentrations of 1 μM indicated weak inducibility of no greater than 40%, where the "fold" value for the positive control was defined as 100%. Some of the test results obtained using the test compounds are shown in Table 5.

TABLE 5

| Test concentration | % of Positive Control | | | | | |
|---|---|---|---|---|---|---|
| Examples | 0.03 μM | 0.1 μM | 0.3 μM | 1 μM | 3 μM | 10 μM |
| Example 59 | 2 | 3 | 11 | 25 | 49 | 59 |
| Example 1 | 6 | 7 | 12 | 20 | 36 | 65 |
| Example 3 | 3 | 3 | 7 | 25 | 23 | 34 |
| Rifampicine (positive control) | — | — | — | — | — | 100 |

Various other assays were also employed in addition to Test Example 4 above in order to evaluate the drug metabolizing enzyme inducibilities, and the compounds of the present invention were confirmed to have low inducibilities for those various drug metabolizing enzymes as well.

INDUSTRIAL APPLICABILITY

The present invention can provide a novel pharmaceutical composition comprising a novel pyrazolo[1,5-a]pyridine compound having CRF receptor antagonism, a salt thereof or a hydrate of the foregoing. A compound of the present invention, a salt thereof or a hydrate of the foregoing has excellent antagonism against CRF receptor, especially against CRF1 receptor, and their toxicity is low and their safety is high, therefore, their usefulness as medicine is high. A compound of the present invention or the like and a pharmaceutical composition comprising them are useful for the therapy or prevention for a disease associated with CRF and/or CRF receptor, especially for depression, depressive symptoms (major depression, single-episode depression, recurrent depression, depression-induced child abuse, postpartum depression, etc.), mania, anxiety, generalized anxiety disorder, panic disorder, phobias, obsessive-compulsive disorder, posttraumatic stress disorder, Tourette's syndrome, autism, affective disorder, dysthymia, bipolar disorder, cyclothymic personality, schizophrenia, peptic ulcer, irritable bowel syndrome, ulcerative colitis, Crohn's disease, diarrhea, constipation, postoperative ileus, stress-associated gastrointestinal disorders, nervous vomiting or the like.

The invention claimed is:

1. An inorganic acid salt of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine.

2. The inorganic acid salt according to claim 1, wherein the inorganic acid is hydrochloric acid, hydrobromic acid or sulfuric acid.

3. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine hydrochloride.

4. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine hydrobromide.

5. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine sulfate.

6. An organic acid salt of N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine.

7. The organic acid salt according to claim 6, wherein the organic acid is sulfonic acid.

8. The organic acid salt according to claim 6, wherein the organic acid is benzenesulfonic acid, ethanesulfonic acid, methane sulfonic acid or p-toluenesulfonic acid.

9. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine benzenesulfonate.

10. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine ethanesulfonate.

11. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine methanesulfonate.

12. N-cyclopropylmethyl-N-7-[2,6-dimethoxy-4-(methoxymethyl)phenyl]-2-ethylpyrazolo[1,5-a]pyridin-3-yl-N-tetrahydro-2H-4-pyranylmethylamine toluenesulfonate.

* * * * *